(12) United States Patent
Kurek et al.

(10) Patent No.: US 12,343,429 B2
(45) Date of Patent: Jul. 1, 2025

(54) METHOD OF DELIVERY OF DNA OR RNA CARGO UNSHIELDED LIPID NANOPARTICLES AND COMPOSITIONS THEREOF

(71) Applicant: NanoVation Therapeutics Inc., Vancouver (CA)

(72) Inventors: Daniel Kurek, Vancouver (CA); Dominik Witzigmann, Vancouver (CA); Jayesh Kulkarni, Vancouver (CA)

(73) Assignee: NanoVation Therapeutics Inc., Vancouver (CA)

( * ) Notice: Subject to any disclaimer, the term of this patent is extended or adjusted under 35 U.S.C. 154(b) by 0 days.

(21) Appl. No.: 18/906,740

(22) Filed: Oct. 4, 2024

(65) Prior Publication Data

US 2025/0114306 A1    Apr. 10, 2025

Related U.S. Application Data

(60) Provisional application No. 63/673,355, filed on Jul. 19, 2024, provisional application No. 63/556,432, filed on Feb. 22, 2024, provisional application No. 63/588,167, filed on Oct. 5, 2023.

(51) Int. Cl.
| | | |
|---|---|---|
| *A61K 9/1272* | (2025.01) | |
| *A61K 9/51* | (2006.01) | |
| *A61K 31/7105* | (2006.01) | |
| *A61K 45/06* | (2006.01) | |
| *C12N 15/113* | (2010.01) | |
| *C12N 15/88* | (2006.01) | |

(52) U.S. Cl.
CPC .......... *A61K 9/1272* (2013.01); *A61K 9/5123* (2013.01); *A61K 9/5192* (2013.01); *A61K 31/7105* (2013.01); *A61K 45/06* (2013.01); *C12N 15/113* (2013.01); *C12N 15/88* (2013.01); *C12N 2310/14* (2013.01)

(58) Field of Classification Search
None
See application file for complete search history.

(56) References Cited

U.S. PATENT DOCUMENTS

| 11,285,222 B2 | 3/2022 | Besin et al. |
| 12,011,507 B2 | 6/2024 | Kurek et al. |
| 2021/0046192 A1 | 2/2021 | Karve et al. |
| 2022/0296517 A1* | 9/2022 | Benenato ........... A61K 31/7105 |

FOREIGN PATENT DOCUMENTS

| WO | 2018089540 A1 | 5/2018 |
| WO | 2020051223 A1 | 3/2020 |
| WO | 2022132926 | 6/2022 |
| WO | 2022246571 | 12/2022 |
| WO | 2022251959 | 12/2022 |
| WO | 2023092218 | 6/2023 |
| WO | 2023172547 | 9/2023 |
| WO | 2023227682 A1 | 11/2023 |
| WO | 2023233042 A1 | 12/2023 |
| WO | 2024006863 A1 | 1/2024 |
| WO | 2024086929 A1 | 5/2024 |
| WO | WO 2025005990 | 1/2025 |
| WO | WO 2025005991 | 1/2025 |

OTHER PUBLICATIONS

Besin et al., 2019, "Accelerated Blood Clearance of Lipid Nanoparticles Entails a Biphasic Humoral Response of B-1 Followed by B-2 Lymphocytes to Distinct Antigenic Moieties", Immunohorizons 3(7): 282-293.
Bleher et al., 2019, "Poly(Sarcosine) Surface Modification Imparts Stealth-Like Properties to Liposomes", Small, 15:1904716 (1 to 10).
Cornebise et al., 2022, "Discovery of a Novel Amino Lipid That Improves Lipid Nanoparticle Performance through Specific Interactions with mRNA", Advanced Functional Materials, 32:2106727 (1 of 12).
Cullis et al., 2017, "Lipid Nanoparticle Systems for Enabling Gene Therapies", Molecular Therapy, 25(7):1467-1475.
Erdmann et al., Mar. 18, 2024, "A HIV-1 Gp41 Peptide-Liposome Vaccine Elicits Neutralizing Epitope-Targeted Antibody Responses in Healthy Individuals", medRxiv The Preprint Server for Health Sciences, Cold Spring Harbor Laboratory, preprint. https://doi.org/10.1101/2024.03.15.24304305.
Evers et al., 2018, "State-of-the-Art Design and Rapid-Mixing Production Techniques of Lipid Nanoparticles for Nucleic Acid Delivery", Small Methods, 2:1700375 (1-20).
Khare et al., 2022, "Development of Lipidoid Nanoparticles for siRNA Delivery to Neural Cells", The AAPS Journal, 24:8 (1 to 17).
Kulkarni et al., 2019, "On the role of helper lipids in lipid nanoparticle formulations of siRNA", Nanoscale, 11:21733-21739.
Kulkarni et al., 2020, "Spontaneous, solvent-free entrapment of siRNA within lipid nanoparticles", Nanoscale, 12:23959-23966.
Lee et al., 2021, "Understanding and overcoming adverse consequences of genome editing on hematopoietic stem and progenitor cells", Molecular Therapy, 29(11):3205-3218.

(Continued)

*Primary Examiner* — Celeste A Roney
(74) *Attorney, Agent, or Firm* — Knobbe Martens Olson & Bear LLP

(57) ABSTRACT

The present disclosure provides unshielded lipid nanoparticles and a process that enables the production of such unshielded lipid nanoparticles, thereby overcoming previous challenges of making particles without causing aggregation thereof. The lipid nanoparticles comprise a nucleic acid cargo molecule; a sterol or a derivative thereof present at a content of at least 12 mol %; a neutral lipid, such as a phospholipid having a choline head group present at a content of between 22 mol % and 65 mol %; and an ionizable cationic amino lipid present at a content of between 15 mol % and 45 mol %; wherein the lipid nanoparticle is non-sterically stabilized with a hydrophilic polymer-lipid conjugate, or otherwise unshielded and wherein each mol % content is relative to total lipid present in the lipid nanoparticle.

14 Claims, 44 Drawing Sheets

(56) References Cited

OTHER PUBLICATIONS

Lokugamage et al., 2021, "Optimization of lipid nanoparticles for the delivery of nebulized therapeutic mRNA to the lungs", Nature Biomedical Engineering, 5:1059-1068.

Musakhanian et al., 2022, "Oxidative Stability in Lipid Formulations: a Review of the Mechanisms, Drivers, and Inhibitors of Oxidation", AAPS PharmSciTech, 23:151 (1 to 30).

Ryals et al., 2020, "The effects of PEGylation on LNP based mRNA delivery to the eye", Plos One, 15(10:e0241006.

Semple et al., 1996, "Influence of Cholesterol on the Association of Plasma Proteins with Liposomes", Biochemistry, 35:2521-2525.

Suk et al., 2016, "PEGylation as a strategy for improving nanoparticle-based drug and gene delivery", Adv Drug Deliv Rev, 99(Pt A): 28-51.

Tam et al., 2013, "Advances in Lipid Nanoparticles for siRNA Delivery", Pharmaceutics, 5:498-507.

Van Der Meel et al., Oct. 27, 2023, "A nature-inspired nanodelivery platform for gene silencing in hematopoietic stem and progenitor cells", Research Square, preprint., pp. 1-15.

Van Der Meel et al., Oct. 27, 2023, "A nature-inspired nanodelivery platform for gene silencing in hematopoietic stem and progenitor cells", Research Square, preprint., Supplementary Information, pp. 1-16.

Wang et al., 2023, "Hot and cold tumors: Immunological features and the therapeutic strategies", MedComm, 4:e343 (1-21).

Zhigaltsev et al., 2023, "Morphological Behavior of Liposomes and Lipid Nanoparticles", Langmuir, 39:3185-3193.

Kulkarni et al., 2018, "On the Formation and Morphology of Lipid Nanoparticles Containing Ionizable Cationic Lipids and siRNA", ACS Nano, 12(5):4787-4795.

Ordobadi, Mina, "Lipid Nanoparticles for Delivery of Bioactive Molecules", 2019, A thesis submitted in partial fulfillment of the requirements for the degree of doctor of philosophy in The Faculty of Graduate and Postdoctoral Studies, University of British Columbia.

PCT International Search Report and the Written Opinion of the International Searching Authority, PCT/CA2024/051319, Jan. 30, 2025.

PCT International Search Report and the Written Opinion of the International Searching Authority, PCT/CA2024/051320, Jan. 6, 2025.

PCT International Search Report and the Written Opinion of the International Searching Authority, PCT/CA2024/051321, Dec. 20, 2024.

Prakash et al., "Microfluidic Fabrication of Lipid Nanoparticles for the Delivery of Nucleic Acids", Adv Drug Deliv Rev., 2022, 184: 114197.

* cited by examiner

SKIN

SMALL INTESTINE

FIGURE 30A
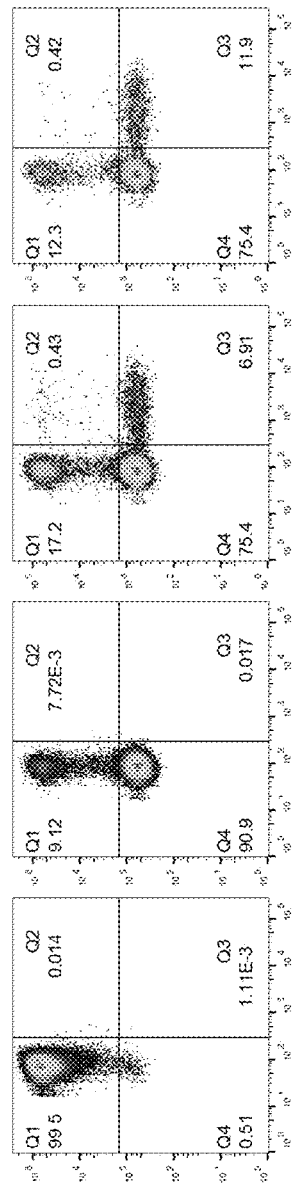
FIGURE 30B
FIGURE 30C
FIGURE 30D
FIGURE 30E

METHOD OF DELIVERY OF DNA OR RNA CARGO UNSHIELDED LIPID NANOPARTICLES AND COMPOSITIONS THEREOF

TECHNICAL FIELD

The present disclosure relates to the delivery of cargo such as nucleic acid using lipid nanoparticles.

BACKGROUND

Lipid nanoparticle (LNP) formulations represent a revolution in the field of nucleic acid delivery. An early example of a lipid nanoparticle product approved for clinical use is Onpattro™. Onpattro™ is a lipid nanoparticle-based short interfering RNA (siRNA) drug for the treatment of polyneuropathies induced by hereditary transthyretin amyloidosis. The success of this LNP delivery system paved the way for the clinical development of the leading LNP-based COVID-19 mRNA vaccines.

The Onpattro™ LNP formulation consists of four main lipid components, namely: ionizable amino lipid, distearoylphosphatidylcholine (DSPC), cholesterol, and polyethylene glycol conjugated lipids (PEG-lipids) at respective molar amounts of 50/10/38.5/1.5. Onpattro™ is still considered the gold standard for comparison in studies of LNP-mediated efficacy and current approaches to LNP design make few deviations from the four-component system.

Of these four components, the ionizable cationic lipid is considered important for the in vivo activity of the LNP system. Accordingly, significant work in the field has focused on improving this lipid component. The ionizable cationic lipid is typically positively charged at low pH, which facilitates association with the negatively charged nucleic acid but is neutral at physiological pH, making it more biocompatible in biological systems. Further, it has been suggested that after the lipid nanoparticles are taken up by a cell by endocytosis, the ability of these lipids to ionize at low pH enables endosomal escape. This in turn allows the nucleic acid to be released into the intracellular compartment.

The PEG-lipid is also considered an essential component of LNP formulations. While serum stable, large unilamellar vesicles (LUV) (termed "liposomes") used for small molecule delivery have been prepared without PEG (Semple et al., 1996, Biochemistry, 35, 2521-2525), its inclusion in solid-core type LNPs containing nucleic acid cargo is considered essential as it is thought to prevent aggregation of the particles during the formulation process (Kulkarni et al., 2020, Nanoscale, 12:23959-23966). LNPs for nucleic acid delivery are formed by a rapid mixing technique during which an organic solvent (e.g., ethanolic) lipid phase is combined with an acidic aqueous phase containing the nucleic acid. The resulting LNP preparation produced during or after mixing is buffer exchanged to neutral pH and the resulting particles contain an electron dense core (referred to often as "solid core"). As the pH of the formulation is raised, the ionizable lipid becomes uncharged and without any electrostatic repulsion, the particles fuse. In the absence of PEG, the particles fuse to produce large polydisperse particles (e.g., around 1000 nm), which lack clinical utility. Indeed, numerous studies have shown that, without PEG, Onpattro™-type siRNA-containing LNPs (N/P of 3) formed aggregates and heterogeneous suspensions (high polydispersity), while the same particles spiked with PEG-lipid had a particle size of around 40-60 nm and a polydispersity in the range of 0.1. It is thought that the inclusion of PEG during neutralization of the formulation provides a steric barrier against further fusion and is essential for the creation of particles of a size range (e.g., between 40 and 120 nm) that are suitable for systemic administration. By contrast, liposomes for small molecule drug delivery, such as large unilamellar vesicles (LUVs) lacking PEG (e.g., DSPC/chol or SM/chol) are prepared by a thin film/hydration method that is not reliant on such fusion events during particle formation.

Thus, while the inclusion of PEG-lipid during liposome (LUV) formation is not required, the prevailing view is that PEG-lipid is critical for producing the type of solid core-type lipid nanoparticles used for nucleic acid delivery. While some investigators have reported the preparation of PEGless LNPs similar to the Onpattro™-type formulation (containing about 10 mol % DSPC) described above (U.S. Pat. No. 11,285,222), the examined LNPs lacking DMG-PEG or having low levels thereof (0 to 0.25 mol %) were found to exhibit low B cell uptake and activation relative to the conventional LNPs having 1.5 mol % DMG-PEG.

Furthermore, hydrophilic polymer-lipid conjugates, such as PEG-lipids are thought to play a key role in extending the storage stability of solid core-type LNPs by reducing aggregation of the particles over time. It has been shown that LNPs having an Onpattro™-type composition of C12-200 ionizable lipid/DSPC/cholesterol/$PEG_{2000}$-DMG at 50/10/38.5/1.5 (mol/mol) required the presence of both siRNA and PEG-lipid for storage stability. (Khare et al., 2022, The AAPS Journal, 24:8). Particle diameters and polydispersity indices for LNPs with and without PEG differed significantly for blank and siRNA loaded LNPs. In particular, the investigators found that siRNA-LNPs with $PEG_{2000}$-DMG maintained low particle diameters and uniform dispersity indices over a period of 7 days post-formulation.

Equally important, the inclusion of PEG-lipid improves the circulation lifetime of lipid nanoparticles. Researchers are now focusing on delivering nucleic acid cargo beyond the liver to expand the repertoire of diseases that are treatable by LNP-mediated nucleic acid delivery and improving blood stability is crucial to bypassing hepatic tissue. PEG-lipids are known to shield the lipid nanoparticle surface, which protects the particles from opsonins and uptake by the mononuclear phagocyte system, as well as preventing their aggregation after administration (Evers et al., 2018, Small Methods, 2, 1700375). It has been shown that siRNA-LNPs containing PEG-DSG accumulate in distal tumours (Lee et al., 2016, Molecular Therapy-Nucleic Acids, 5, e348). Nevertheless, PEG-lipids have certain drawbacks as they can prevent the delivery of nucleic acid into cells by decreasing fusogenicity with target cells. The hydrophilic coating, or steric barrier, provided by the PEG-lipid has been reported to inhibit interactions with the endosomal membrane, thereby preventing endosomal escape, which is required for cytosolic delivery. The presence of a long-lived PEG coating dramatically reduces gene-silencing potency (Cullis and Hope, 2017, Molecular Therapy, 25 (7): 1467-1475). To address this problem, short PEGs (e.g., PEG-DMG) have been examined that diffuse out of the LNP post-administration. The design of such particles involves finding a balance between stabilization in storage or particle formation and shedding of the PEG-lipid post administration. Despite these advances, there are reports of undesirable immune responses being mounted in vivo against PEG molecules.

Accordingly, studies are ongoing to find safe and potent PEG alternatives for mRNA LNPs. To this end, lipid nanoparticles have been prepared with an apolipoprotein surface stabilizer rather than PEG with the aim of avoiding the immunogenicity of PEG, while improving the shelf-life and structural stability of the particles, as well as achieving targeting to myeloid cells (WO 2023/233042 and Hofstraat et al., 2023, preprint, Oct. 27, 2023, A nature-inspired nanodelivery platform for gene silencing in hematopoietic stem and progenitor cells. Research Square). The latter study examined apolipoprotein coated lipid nanoparticles for gene silencing in hematopoietic stem and progenitor cells. However, the studies concluded that low phase transition temperature phosphocholine lipids, such as POPC and DMPC (e.g., 25° C. or less), exhibited high transfection efficiency of siRNA, while lipid nanoparticles with a higher phase transition temperature lipid, namely DPPC (41° C.), were found to be less potent (suppl. FIG. 4).

Other groups have examined alternative hydrophilic polymers, such as polysarcosine (Bleher et al., 2019, Nano Micro Small, 15:1904716). In addition, block copolymers containing PEG and a hydrophobic block, namely poloxamers, have also been investigated to replace PEG-lipid in LNPs and were found to exhibit resistance to cycles of freeze and thaw (US2021/0046192). Regardless of the hydrophilic polymer utilized, however, there remains the potential challenge of overcoming reductions in LNP fusogenicity induced by the steric barrier.

Accordingly, there is a continuing need in the art for nucleic acid-LNP formulations having desirable properties, such as shelf stability, favourable physiochemical properties and/or extrahepatic delivery but that do not suffer from immunogenicity and/or reductions in fusogenicity often associated with the use of PEG-lipid or other surface stabilizers.

SUMMARY

The present disclosure addresses one or more problems in the art and/or provides useful alternatives thereof.

The present disclosure is based in part on the finding that uncoated LNPs (referred to herein as "unshielded") encapsulating nucleic acid with elevated neutral lipid content (e.g., phospholipid at greater than 20 mol %, greater than 22 mol %, more typically greater than 30 mol %), with substantially no hydrophilic polymer-lipid conjugate (e.g., no or substantially no PEG-lipid) or other surface stabilizer possess unexpected improvements in stability after being subjected to shearing and/or oxidative conditions relative to an otherwise substantially identical PEG-surface stabilized control LNP. Yet further, it has been unexpectedly found that such unshielded LNPs exhibit similar or even improved in vivo extra-hepatic nucleic acid delivery relative to otherwise identical LNPs coated with PEG. Due to the lack of a surface stabilizer, such as hydrophilic polymer lipid conjugate (e.g., PEG-lipid), or small amounts thereof, such unshielded particles with elevated non-cationic lipid content (e.g., phospholipid) may also exhibit reduced immunogenicity after administration and/or improved nucleic acid delivery to a cell due to improved fusogenicity. Lipid nanoparticles with elevated neutral lipid as defined herein have a distinct morphology that has an electron dense region and an aqueous portion as visualized by Cryo-EM (e.g., see FIG. 19).

As noted, the preparation of nucleic acid-LNPs without a surfactant, such as PEG, can be challenging. To this end, further provided herein is an inventive process of making unshielded LNPs (e.g., unshielded, PEG-less LNPs) that allows for the formulation of a wider range of ionizable cationic lipids than previously achieved.

In addition, lipid nanoparticles consisting essentially of non-cationic or neutral lipid, sterol and ionizable lipid at the foregoing mol % exhibit unexpected increases in T cell and stem cell delivery relative to a PEG-containing baseline composition. In addition, such unshielded LNPs encapsulating nucleic acid encoding antigen exhibit improved immune response relative to PEG-containing LNPs and thus may function as improved vaccines and avoid toxicity concerns attributed to the PEG component. Yet further, unexpected improvements in expression of mRNA after intramuscular injection of unshielded mRNA LNPs were observed. Such results support the use of unshielded mRNA LNPs for improved localized delivery and expression of mRNA after direct injection into an organ and/or tissue.

According to one aspect of the disclosure, there is provided a lipid nanoparticle comprising: a nucleic acid cargo molecule; a sterol (encompassing a sterol derivative thereof) present at a content of at least 12 mol %; a neutral lipid present at a content of between 20 mol % and 65 mol % or 22 mol % and 65 mol %; and an ionizable cationic amino lipid present at a content of between 15 mol % and 45 mol %, wherein the lipid nanoparticle is unshielded or is non-sterically stabilized with a hydrophilic polymer-lipid conjugate, and wherein each content in mol % is relative to a total lipid content present in the lipid nanoparticle.

In one embodiment, the content of the sterol is between 15 mol % and 45 mol %. In one embodiment, the content of the sterol is between 15 mol % and 40 mol %. In another embodiment the content of the sterol is between 16 mol % and 35 mol %. In a further embodiment, the content of the sterol is between 18 mol % and 30 mol %.

In another embodiment, the ionizable cationic amino lipid content is less than 30 mol %. In yet a further embodiment, the ionizable cationic amino lipid content is less than 28 mol %.

In another embodiment, the neutral lipids is a phospholipid having a choline head group. In a further embodiment, the content of the phospholipid having a choline head group is between 25 mol % and 60 mol %. In a further embodiment, the content of the phospholipid having a choline head group is between 30 mol % and 55 mol %. In another embodiment, the content of the phospholipid having a choline head group is between 35 mol % and 55 mol %. In yet another embodiment, the content of the phospholipid having a choline head group is between 38 mol % and 55 mol %.

In another embodiment, the content of the hydrophilic-polymer lipid conjugate is less than 0.50 mol %. In a further embodiment, the content of the hydrophilic-polymer lipid conjugate is less than 0.45 mol %. In a further embodiment, the content of the hydrophilic-polymer lipid conjugate is less than 0.40 mol %.

In one embodiment, the phospholipid having the choline head group is a phosphatidylcholine or a sphingolipid and wherein the phosphatidylcholine:sterol or sphingolipid:sterol molar ratio is between 0.5:1 and 4:1 (mol:mol). In another embodiment, the phosphatidylcholine:sterol or sphingolipid:sterol molar ratio is between 0.6:1 and 3.5:1 (mol:mol). In another embodiment, the phosphatidylcholine:sterol or sphingolipid:sterol molar ratio is between 0.7:1 and 3.2:1 (mol:mol). In a further embodiment, the phosphatidylcholine:sterol or sphingolipid:sterol molar ratio is between 0.8:1 and 3:1 (mol:mol). In a further embodiment, the phosphatidylcholine:sterol or sphingolipid:sterol molar ratio is between 0.7:1 and 1.5:1 (mol:mol).

In a further embodiment, the nucleic acid cargo molecule is siRNA, mRNA, vector nucleic acid, an antisense oligonucleotide or is a nucleic acid-protein or peptide complex. In another embodiment, the cargo molecule is mRNA, siRNA, vector nucleic acid or an antisense oligonucleotide.

In a further embodiment the ionizable lipid is a sulfur-containing amino lipid. In one embodiment, at least one sulfur atom is present in at least one of the lipophilic chains of the ionizable lipid. In another embodiment, the ionizable lipid is a "non-furan ring-containing ionizable lipid" as defined herein. In another embodiment, the ionizable lipid is a non-MC3 type lipid as defined herein. In another embodiment, the ionizable lipid is a non-cyclopentane ring-containing ionizable lipid. In another embodiment, the ionizable lipid has one or more lipophilic chains with one or more biodegradable groups in at least one lipophilic chain.

In a further embodiment, the sterol is cholesterol.

In another embodiment, the phospholipid having a choline head group is a phosphatidylcholine selected from DOPC, DPPC and DSPC.

According to a further embodiment, the content of the phosphatidylcholine comprises at least DSPC.

In a further embodiment, the phospholipid having a choline head group is a sphingolipid, such as sphingomyelin.

According to another aspect of the disclosure, there is provided a method for delivery of mRNA or vector DNA for in vivo production of protein or peptide in an extrahepatic tissue or organ, the method comprising administering to a subject a lipid nanoparticle having at least 12 mol % of a sterol, a neutral lipid at 20 to 65 mol % or at 22 to 65 mol % and an ionizable cationic amino lipid at 15 to 35 mol %, wherein each mol % is relative to a total lipid content present in the lipid nanoparticle and the lipid nanoparticle being unshielded or having substantially no hydrophilic polymer-lipid conjugate, wherein the mRNA or vector DNA is encapsulated within the lipid nanoparticle and wherein the administering of the lipid nanoparticle results in extrahepatic expression of the protein or peptide encoded by the mRNA or vector DNA.

In a further embodiment, the lipid nanoparticle has equal to or greater expression of the mRNA or vector DNA in the spleen, heart, skin and/or small intestine relative to a lipid nanoparticle that contains 1.5 mol % $PEG_{2000}$-DMG in place of 1.5 mol % of the sterol and that is an otherwise identical formulation.

According to a further aspect of the disclosure, there is provided a method for delivery of siRNA or antisense oligonucleotide for in vivo extrahepatic silencing of a gene, the method comprising administering to a subject a lipid nanoparticle having at least 12 mol % of a sterol, a neutral lipid at 20 to 60 mol %, 22 to 60 mol % or 35 to 60 mol % and an ionizable cationic amino lipid at 15 to 35 mol %, wherein each mol % is relative to a total lipid content present in the lipid nanoparticle and the lipid nanoparticle being unshielded or having substantially no hydrophilic polymer-lipid conjugate, wherein the siRNA or antisense oligonucleotide is encapsulated within the lipid nanoparticle and wherein the administering of the lipid nanoparticle results in extrahepatic gene silencing of an mRNA in an extrahepatic cell targeted by the siRNA or antisense oligonucleotide that is encapsulated by the lipid nanoparticle.

In another embodiment, the administering of the lipid nanoparticle results in an increase in silencing of the nucleic acid in the spleen, heart, skin or small intestine relative to a lipid nanoparticle that contains 1.5 mol % $PEG_{2000}$-DMG in place of 1.5 mol % of the sterol and that is an otherwise identical formulation.

In another embodiment of the foregoing methods, the content of the sterol is between 15 mol % to 40 mol %. In a further embodiment the content of the sterol is between 16 mol % to 35 mol %. In another embodiment, the content of the sterol or the derivative thereof is between 18 mol % to 30 mol %.

In another embodiment of the foregoing methods, the content of the ionizable cationic amino lipid is less than 30 mol %. According to another embodiment of the foregoing methods, the content of the ionizable cationic amino lipid is less than 28 mol %.

In another embodiment of the foregoing methods, the neutral lipid is a phosphatidylcholine and wherein the lipid nanoparticle has a phosphatidylcholine content that is between 20 mol % and 60 mol %. In one embodiment, the phosphatidylcholine content is between 25 mol % and 58 mol %. In a further embodiment, the phosphatidylcholine content is between 30 mol % and 55 mol %.

In another embodiment of the foregoing methods, the phosphatidylcholine content is between 35 mol % and 55 mol %. In a further embodiment, the phosphatidylcholine content is between 38 mol % and 55 mol %.

In another embodiment of the foregoing methods, the hydrophilic-polymer lipid content is less than 0.50 mol %. In a further embodiment, the hydrophilic-polymer lipid content is less than 0.45 mol %. According to a further embodiment, the hydrophilic-polymer lipid content is less than 0.40 mol %.

In another embodiment of the foregoing methods, the neutral lipid is a phosphatidylcholine and the phosphatidylcholine:sterol molar ratio is between 0.5:1 and 4:1 (mol:mol). In another embodiment, the phosphatidylcholine:sterol molar ratio is between 0.6:1 and 3.5:1 (mol:mol). In a further embodiment, the phosphatidylcholine:sterol molar ratio is between 0.7:1 and 3.2:1 (mol:mol). In another embodiment, the phosphatidylcholine:sterol molar ratio is between 0.8:1 and 3:1 (mol:mol) or between 0.7:1 and 1.5:1 (mol:mol).

In another embodiment of the foregoing methods, the ionizable cationic amino lipid is a sulfur-containing lipid and/or comprises a biodegradable functional group (e.g., an ester, comprises an ester or a disulfide). In another embodiment, the ionizable lipid is a "non-furan ring-containing ionizable lipid" as defined herein. In another embodiment, the ionizable lipid is a non-MC3 type lipid as defined herein. In another embodiment, the ionizable lipid is a non-cyclopentane ring-containing ionizable lipid. In another embodiment, the ionizable lipid has one or more lipophilic chains with one or more biodegradable groups in at least one lipophilic chain.

In another embodiment of the foregoing methods, the sterol is cholesterol or the derivative thereof is a cholesterol derivative.

In another embodiment of the foregoing methods, the phosphatidylcholine is selected from DOPC, DPPC and DSPC. In one embodiment, the phosphatidylcholine content comprises at least DSPC.

In a further embodiment, the administration is by local injection to a disease site. In one embodiment, the disease site is a tumour.

In another embodiment of the foregoing methods, the lipid nanoparticle comprises the mRNA, wherein the mRNA encodes an immunostimulatory agent and wherein the administration is by local injection to a tumour. In one embodiment, the immunostimulatory agent encoded by the mRNA is a cytokine.

In another embodiment of the foregoing methods, there is an initial step of pretreatment to the subject that induces leukopenia or comprises injection of an immunosuppressive drug, the pretreatment followed by the administering the lipid nanoparticle at a second time point to the subject.

In another aspect, there is provided a use of a lipid nanoparticle that is unshielded or is non-sterically stabilized with a hydrophilic polymer-lipid conjugate for in vivo expression of protein or peptide from encapsulated mRNA or vector DNA in an extrahepatic tissue or organ. Such unshielded or non-sterically stabilized LNP in some examples include any one of the features of the embodiments described above.

In another aspect, there is provided a use of a lipid nanoparticle that is unshielded or is non-sterically stabilized with a hydrophilic polymer-lipid conjugate for in vivo extrahepatic silencing by encapsulated siRNA or antisense oligonucleotide in an extrahepatic tissue or organ. Such unshielded or non-sterically stabilized LNP in some examples include any one of the features of the embodiments described above.

In one embodiment, the use of the lipid nanoparticle is for local injection to a disease site. In one embodiment, the disease site is a tumour.

According to another aspect of the disclosure, there is provided a process of preparing the lipid nanoparticle that is unshielded or is non-sterically stabilized with a hydrophilic polymer-lipid conjugate, the process comprising: combining a first aqueous stream comprising a buffer and the nucleic acid and a second organic solvent stream comprising the sterol and the neutral lipid in a mixing device to form the lipid nanoparticle, the mixing device comprising a first inlet for introducing the first aqueous stream thereto and a second inlet for introducing the second organic solvent stream thereto, a mixing region in which the first and second streams are combined and an outlet through which the lipid nanoparticle exits the mixing device; and concentrating the lipid nanoparticle so formed to produce a concentrated lipid nanoparticle solution, wherein the process further comprises forming a buffer-diluted lipid nanoparticle solution prior to the concentrating by diluting the lipid nanoparticle with a buffer solution and/or by using a volumetric flow rate of the first aqueous stream in the mixing device that is greater than a flow rate of the second organic solvent stream.

In one embodiment, the process comprises forming the buffer-diluted lipid nanoparticle solution and wherein the buffer-diluted lipid nanoparticle solution is dialyzed prior to the concentrating.

In another embodiment, the second organic solvent stream comprises ethanol.

In a further embodiment, the mixing device is a T-mixer.

In a further embodiment, the buffer in the first stream and the buffer solution for the diluting is the same buffer.

In one embodiment, the buffer solution for diluting is an acetate buffer, phosphate buffered saline, a formate buffer and/or succinic acid buffer.

In a further embodiment, the mixing device is a T-junction mixer, a herringbone micromixer, a toroidal mixer or a multi-inlet vortex mixer.

In yet a further embodiment, the mixing device is a T-junction mixer with respective pumps to control the volumetric flow rates of the first and second streams.

In another aspect of the disclosure, there is provided a lipid nanoparticle that is unshielded and produced by the foregoing process.

Figure 4A:
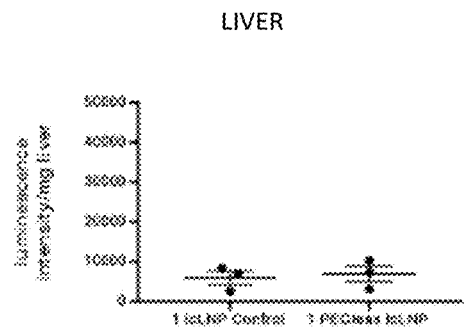
FIG. 4A is a graph showing in vivo luminescence of luciferase mRNA following extraction of the liver of CD-1 mice after treatment with luciferase mRNA-containing LNPs with and without PEG. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.
Figure 4B:
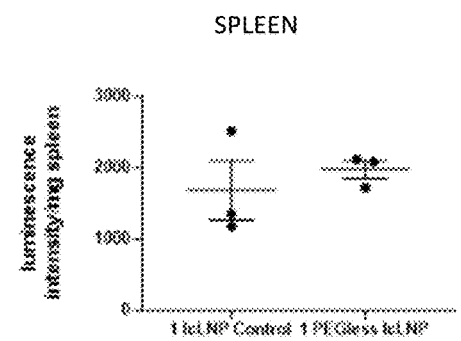

FIG. 4B is a graph showing in vivo luminescence of luciferase mRNA following extraction of the spleen of CD-1 mice after treatment with luciferase mRNA-containing LNPs with and without PEG. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Figure 4C:
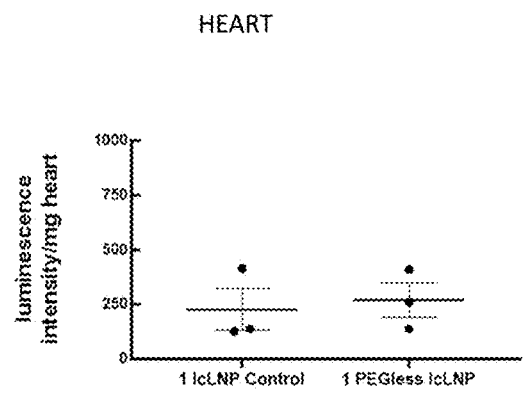

FIG. 4C is a graph showing in vivo luminescence of luciferase mRNA following extraction of the heart of CD-1 mice after treatment with luciferase mRNA-containing LNPs with and without PEG-2000. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Figure 4D:
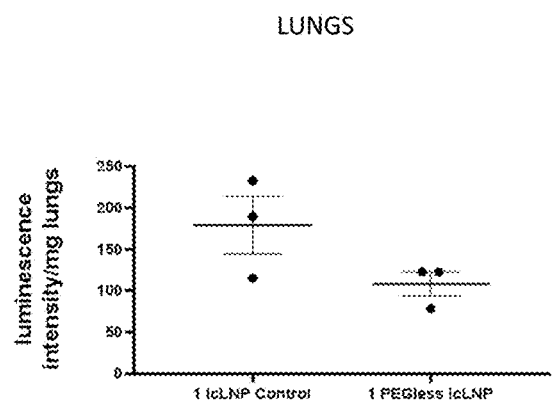

FIG. 4D is a graph showing in vivo luminescence of luciferase mRNA following extraction of the lungs of CD-1 mice after treatment with luciferase mRNA-containing LNPs with and without PEG. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Figure 4E:
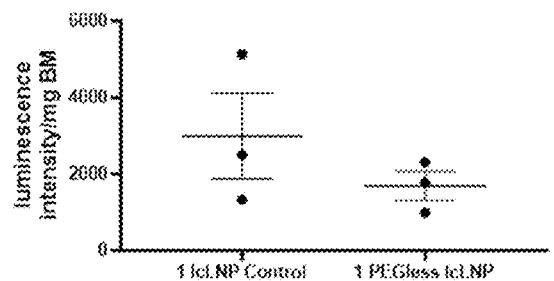

FIG. 4E is a graph showing in vivo luminescence of luciferase mRNA following extraction of the bone marrow of CD-1 mice after treatment with luciferase mRNA-containing LNPs with and without PEG. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Figure 4F:
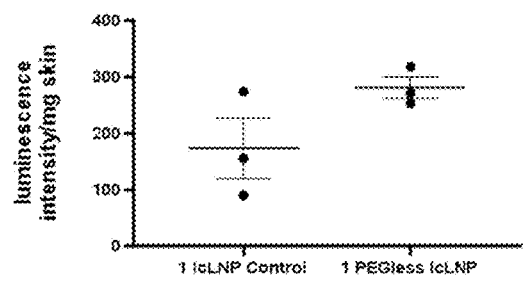

FIG. 4F is a graph showing in vivo luminescence of luciferase mRNA following extraction of the skin of CD-1 mice after treatment with luciferase mRNA-containing LNPs with and without PEG. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Figure 4G:
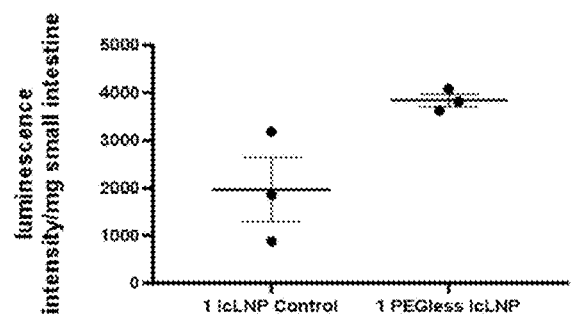

FIG. 4G is a graph showing in vivo luminescence of luciferase mRNA following extraction of the intestine of CD-1 mice after treatment with luciferase mRNA-containing LNPs with and without PEG. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Figure 5A:
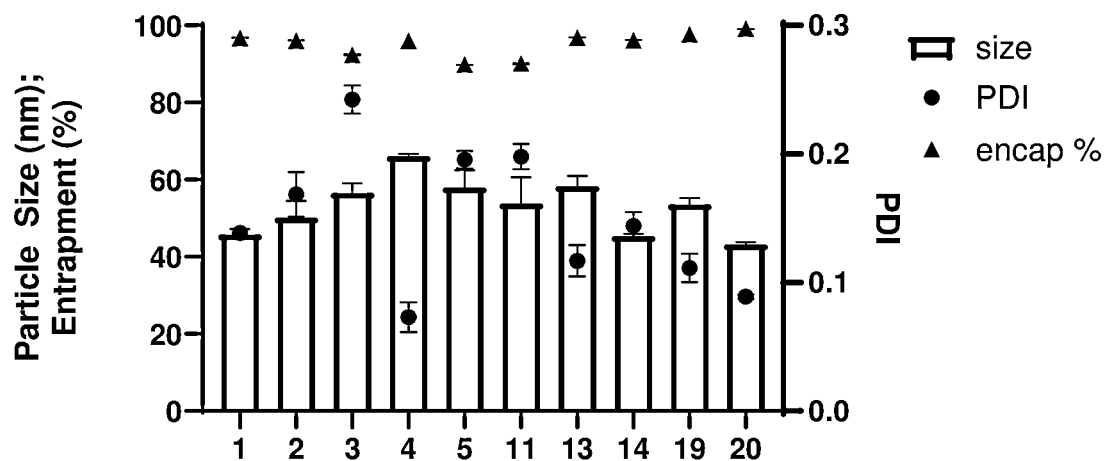

FIG. 5A is a graph showing entrapment (%), particle size (nm) and PDI of pDNA-LNPs containing no PEG and formulated with various ionizable cationic lipids using a standard ethanol mixing method. The formulations contained ionizable cationic lipid/DSPC/cholesterol (27.4/50/22.6 mol/mol). The nitrogen-to-phosphate (N/P) ratio was 9. The ionizable lipids were 1, 2, 3, 4, 5, 11, 13, 14, 19 and 20 (set forth in Example 3).

Figure 5B:
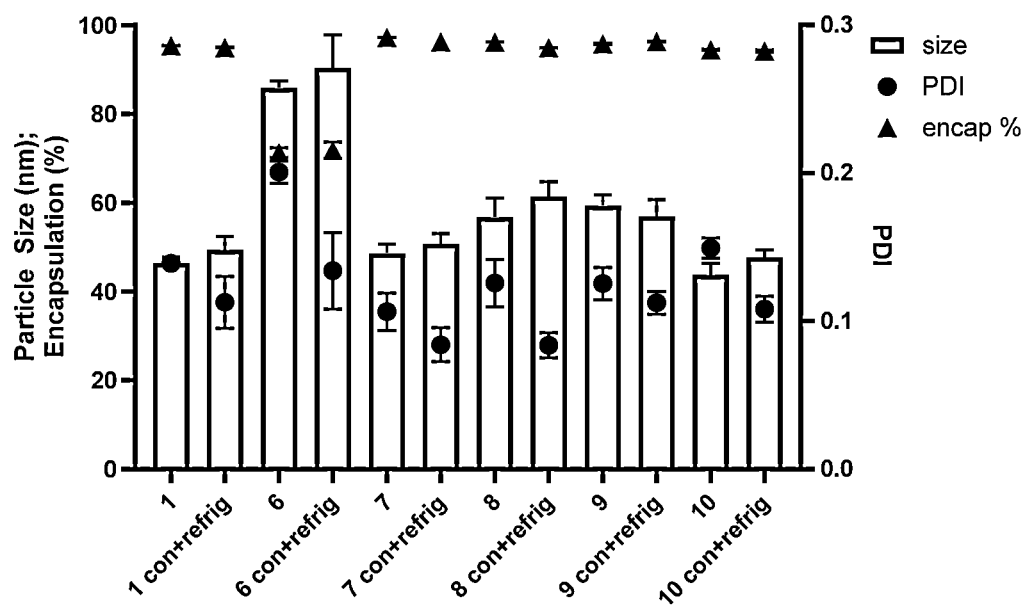

FIG. 5B is a graph showing entrapment (%), particle size (nm) and PDI of pDNA-LNPs containing no PEG and formulated with various ionizable cationic lipids using a standard ethanol mixing method. The formulation was ionizable cationic lipid/DSPC/cholesterol (27.4/50/22.6 mol/mol). The nitrogen-to-phosphate (N/P) ratio was 9. The ionizable lipids were 1, 6, 7, 8, 9 and 10 (set forth in Example 3). The graph shows the biophysical properties before and after concentration and refrigeration.

Figure 6:
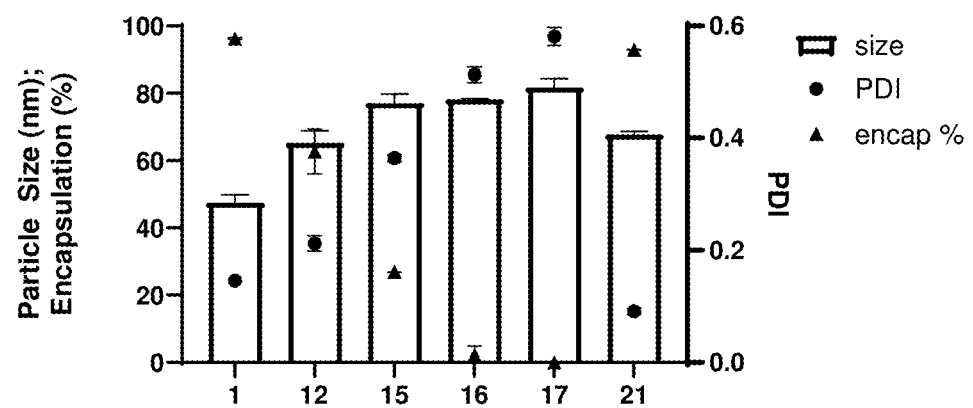

FIG. 6 is a graph showing entrapment (%), particle size (nm) and PDI of mRNA-LNPs containing no PEG and formulated with various ionizable cationic lipids using a standard ethanol mixing method. The formulations were ionizable cationic lipid/DSPC/cholesterol (27.4/50/22.6 mol/mol). The nitrogen-to-phosphate (N/P) ratio was 9. The ionizable lipids were 1, 12, 15, 16, 17 and 21.

Figure 7A:
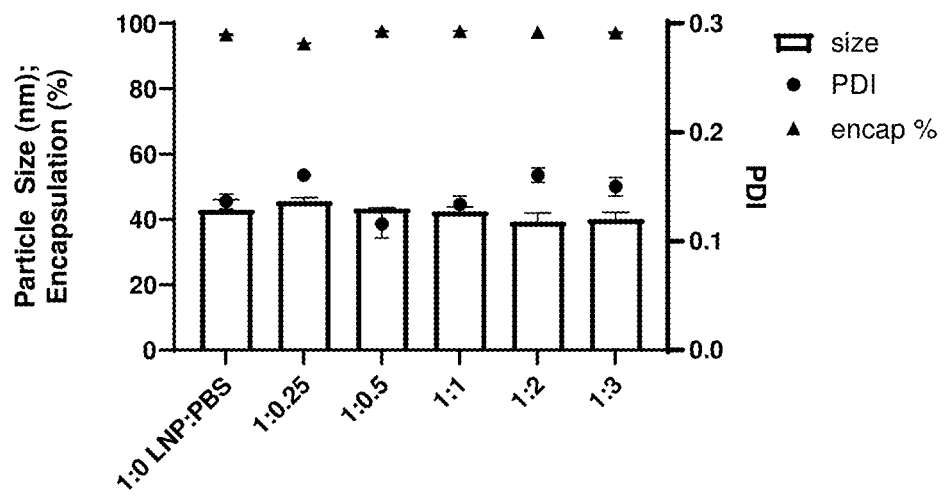

FIG. 7A is a graph showing entrapment (%), particle size (nm) and PDI of mRNA-LNPs containing no PEG and formulated with 1 using a modified ethanol mixing method using phosphate buffer saline (PBS) dilution after T-mixing. The formulations were 1/DSPC/cholesterol (27.4/50/22.6 mol/mol). The nitrogen-to-phosphate (N/P) ratio was 9. The dilutions with PBS after T-mixing are indicated on the x-axis and are depicted as LNP:PBS (v:v). The physiochemical properties were measured after dialysis.

Figure 7B:
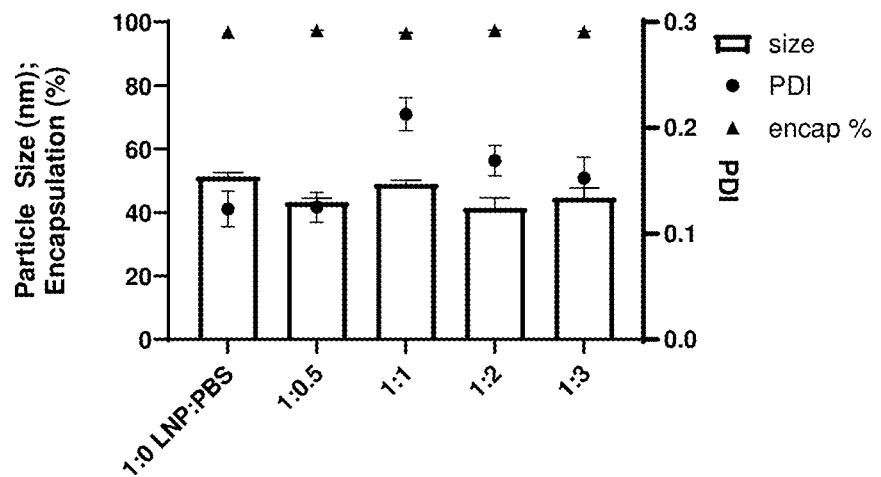

FIG. 7B is a graph showing entrapment (%), particle size (nm) and PDI of mRNA-LNPs containing no PEG and formulated with 1 using a modified ethanol mixing method using PBS dilution after T-mixing. The formulations were 1/DSPC/cholesterol (27.4/50/22.6 mol/mol). The nitrogen-to-phosphate (N/P) ratio was 9. The dilutions with PBS after T-mixing are indicated on the x-axis and are depicted as LNP:PBS (v:v). The physiochemical properties were measured after concentration and overnight storage subsequent to dialysis.

Figure 7C:
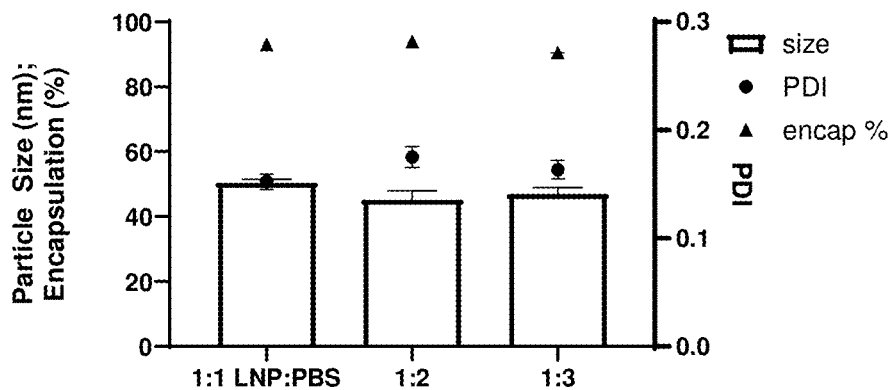

FIG. 7C is a graph showing entrapment (%), particle size (nm) and PDI of mRNA-LNPs containing no PEG and formulated with 12 ionizable lipid using a modified ethanol mixing method using PBS dilution after T-mixing. The formulations were 12/DSPC/cholesterol (27.4/50/22.6 mol/mol). The nitrogen-to-phosphate (N/P) ratio was 9. The dilutions with PBS after T-mixing are indicated on the x-axis and are depicted as LNP:PBS (v:v). The physiochemical properties were measured after dialysis.

Figure 7D:
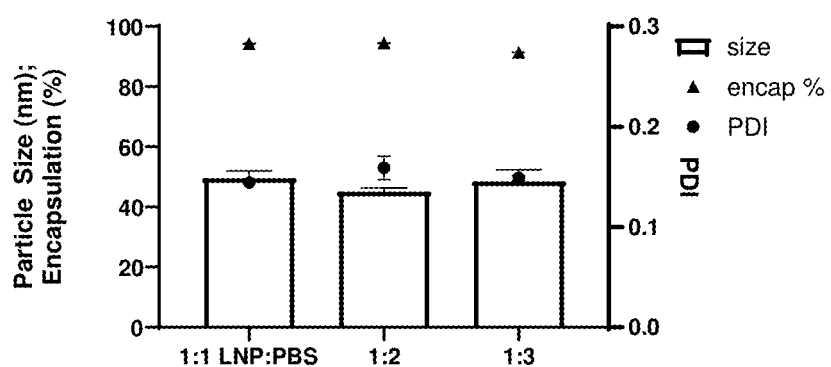

FIG. 7D is a graph showing entrapment (%), particle size (nm) and PDI of mRNA-LNPs containing no PEG and formulated with 12 ionizable lipid using a modified ethanol mixing method using PBS dilution after T-mixing. The formulations were 12/DSPC/cholesterol (27.4/50/22.6 mol/mol). The nitrogen-to-phosphate (N/P) ratio was 9. The dilutions with PBS after T-mixing are indicated on the x-axis and are depicted as LNP:PBS (v:v). The physiochemical properties were measured after concentration and overnight storage subsequent to dialysis.

Figure 7E:
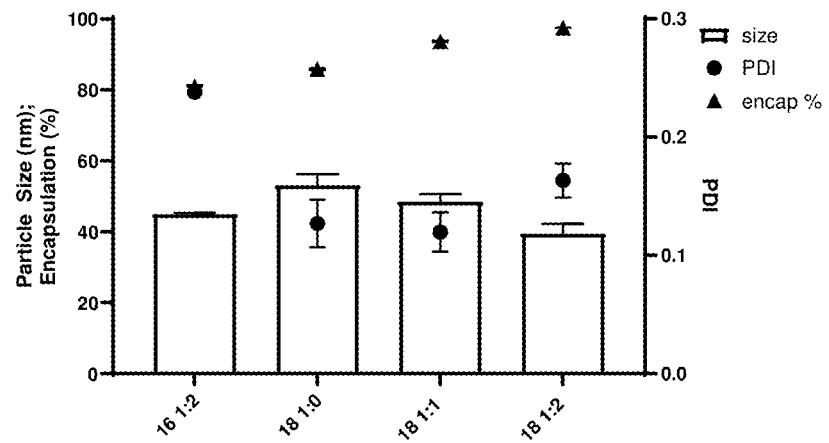

FIG. 7E is a graph showing entrapment (%), particle size (nm) and PDI of mRNA-LNPs containing no PEG and formulated with 16 or 18 ionizable lipids using a modified ethanol mixing method using PBS dilution after T-mixing. The formulations were ionizable lipid/DSPC/cholesterol (27.4/50/22.6 mol/mol). The nitrogen-to-phosphate (N/P) ratio was 9. The dilutions with PBS after T-mixing are indicated on the x-axis and are depicted as LNP:PBS (v:v). The physiochemical properties were measured after dialysis.

Figure 7F:
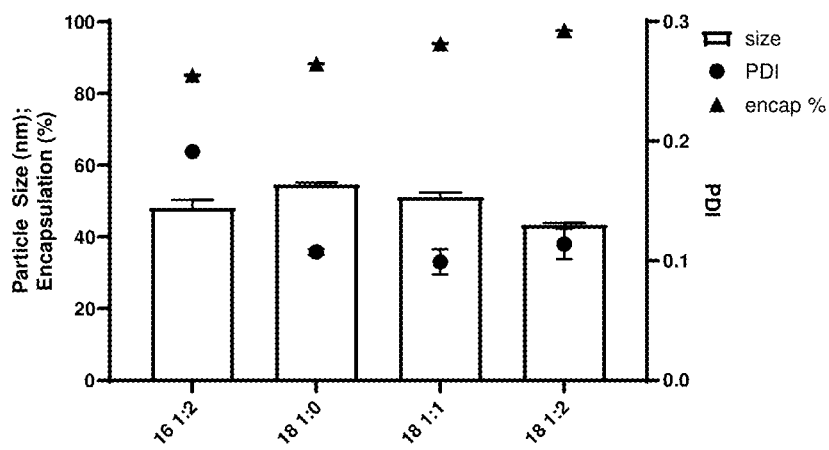

FIG. 7F is a graph showing entrapment (%), particle size (nm) and PDI of mRNA-LNPs containing no PEG and formulated with 16 or 18 ionizable lipid using a modified ethanol mixing method using PBS dilution after T-mixing. The formulations were ionizable lipid/DSPC/cholesterol (27.4/50/22.6 mol/mol). The nitrogen-to-phosphate (N/P) ratio was 9. The dilutions with PBS after T-mixing are indicated on the x-axis and are LNP:PBS (v:v). The physiochemical properties were measured after concentration and overnight storage subsequent to dialysis.

Figure 8A:
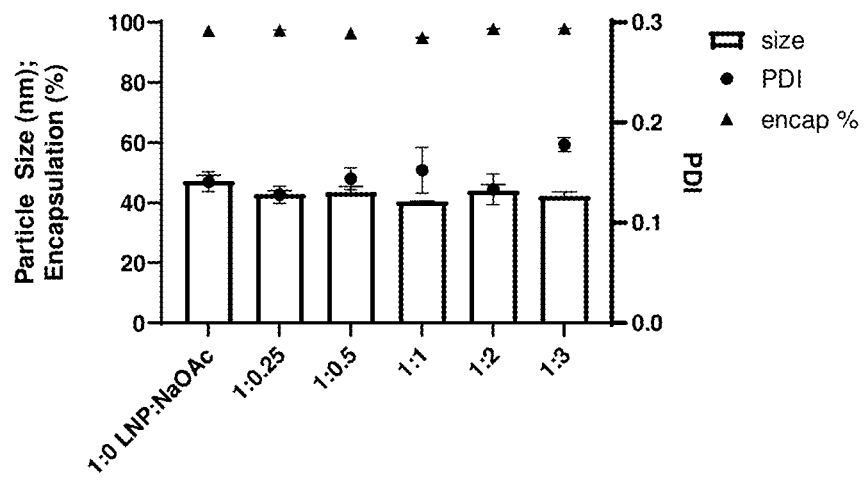

FIG. 8A is a graph showing entrapment (%), particle size (nm) and PDI of mRNA-LNPs containing no PEG and formulated with 1 using a modified ethanol mixing method with 25 mM sodium acetate (NaOAc) dilution after T-mixing. The formulations were 1/DSPC/cholesterol (27.4/50/22.6 mol/mol). The nitrogen-to-phosphate (N/P) ratio was 9. The dilutions with sodium acetate after T-mixing are indicated on the x-axis and are depicted as LNP:NaOAc (v:v). The physiochemical properties were measured after dialysis.

Figure 8B:
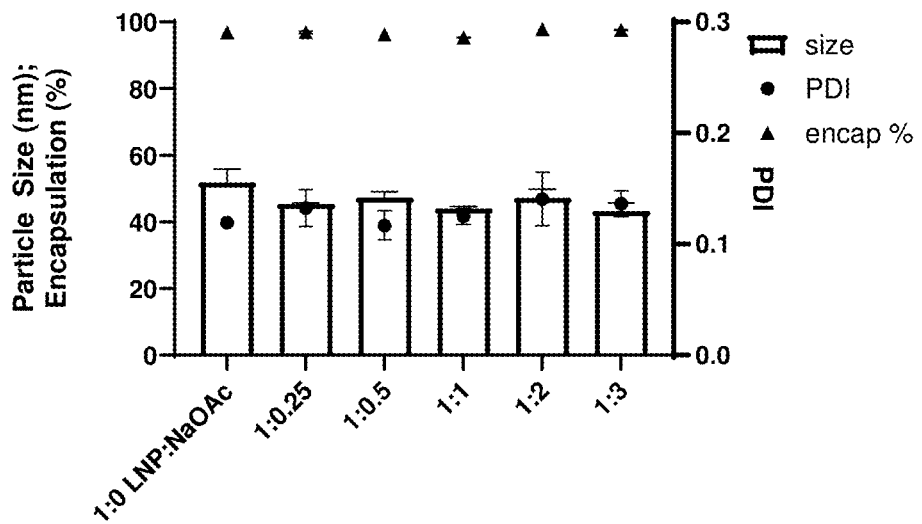

FIG. 8B is a graph showing entrapment (%), particle size (nm) and PDI of mRNA-LNPs containing no PEG and formulated with 1 using a modified ethanol mixing method with sodium acetate (NaOAc) dilution after T-mixing. The formulations were 1/DSPC/cholesterol (27.4/50/22.6 mol/mol). The nitrogen-to-phosphate (N/P) ratio was 9. The dilutions with sodium acetate after T-mixing are indicated on the x-axis and are depicted as LNP:NaOAc (v:v). The physiochemical properties were measured after concentration and overnight storage subsequent to dialysis.

Figure 8C:
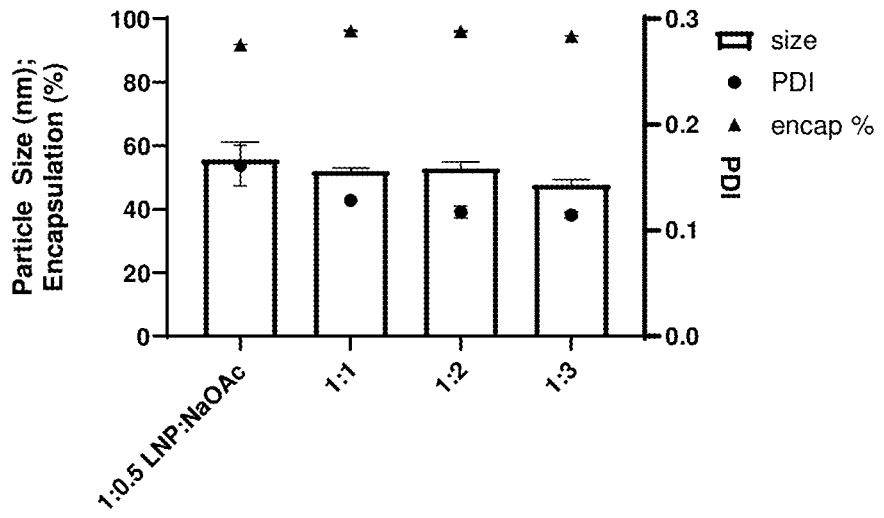

FIG. 8C is a graph showing entrapment (%), particle size (nm) and PDI of mRNA-LNPs containing no PEG and formulated with 12 ionizable lipid using a modified ethanol mixing method with sodium acetate (NaOAc) dilution after T-mixing. The formulations were 12/DSPC/cholesterol (27.4/50/22.6 mol/mol). The nitrogen-to-phosphate (N/P) ratio was 9. The dilutions with sodium acetate after T-mixing are indicated on the x-axis and are depicted as LNP:NaOAc (v:v). The physiochemical properties were measured after dialysis.

Figure 8D:
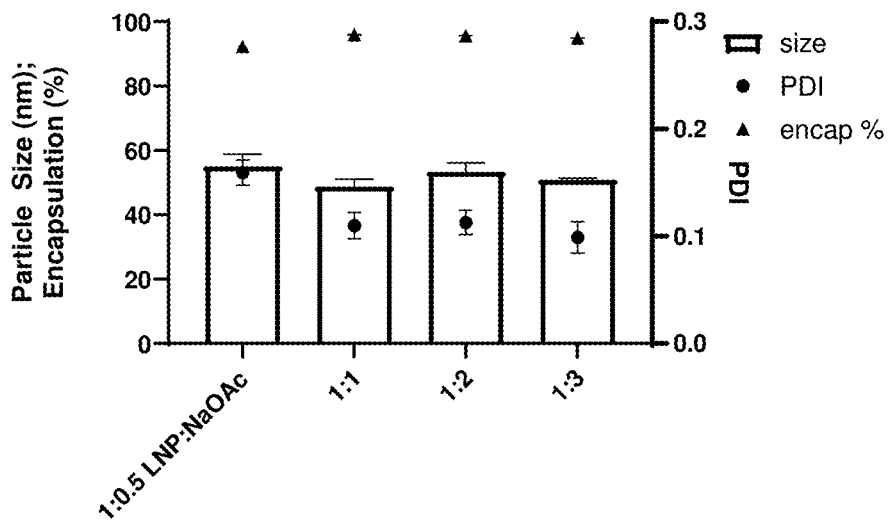

FIG. 8D is a graph showing entrapment (%), particle size (nm) and PDI of mRNA-LNPs containing no PEG and formulated with 12 ionizable lipid using a modified ethanol mixing method with sodium acetate (NaOAc) dilution after T-mixing. The formulations were 12/DSPC/cholesterol (27.4/50/22.6 mol/mol). The nitrogen-to-phosphate (N/P) ratio was 9. The dilutions with sodium acetate after T-mixing are indicated on the x-axis and are depicted as LNP:NaOAc (v:v). The physiochemical properties were measured after concentration and overnight storage subsequent to dialysis.

Figure 8E:
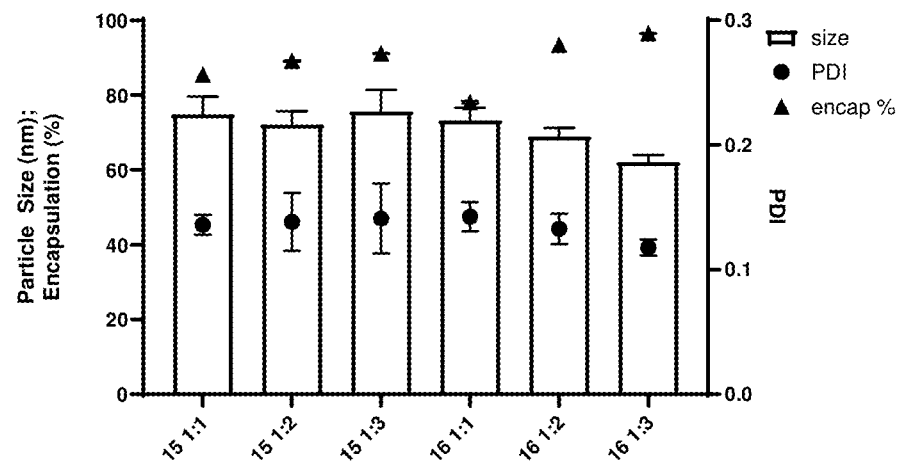

FIG. 8E is a graph showing entrapment (%), particle size (nm) and PDI of mRNA-LNPs containing no PEG and formulated with 15 or 16 ionizable lipid using a modified ethanol mixing method with sodium acetate (NaOAc) dilution after T-mixing. The formulations were ionizable lipid/DSPC/cholesterol (27.4/50/22.6 mol/mol). The nitrogen-to-phosphate (N/P) ratio was 9. The dilutions with sodium acetate after T-mixing are indicated on the x-axis and are depicted as LNP:NaOAc (v:v). The physiochemical properties were measured after dialysis.

Figure 8F:
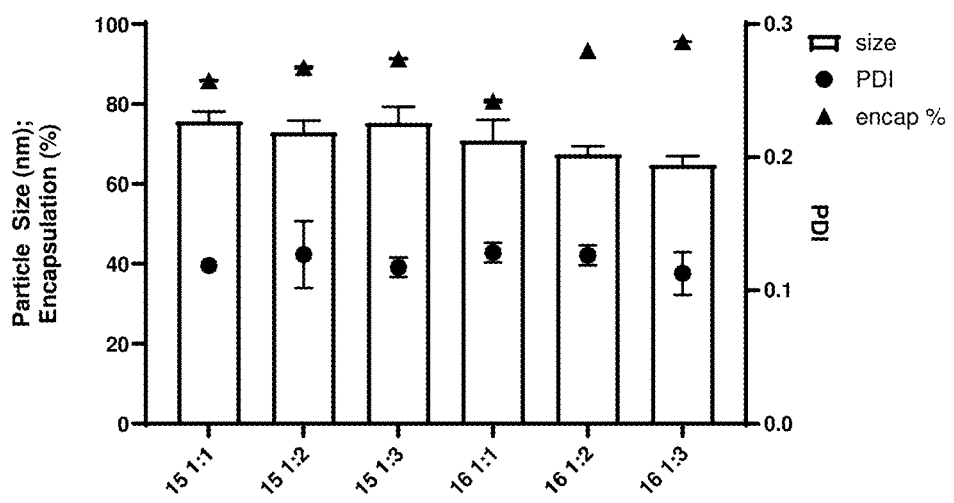

FIG. 8F is a graph showing entrapment (%), particle size (nm) and PDI of mRNA-LNPs containing no PEG and formulated with 15 or 16 ionizable lipid using a modified ethanol mixing method with sodium acetate (NaOAc) dilution after T-mixing. The formulations were ionizable lipid/DSPC/cholesterol (27.4/50/22.6 mol/mol). The nitrogen-to-phosphate (N/P) ratio was 9. The dilutions with sodium acetate after T-mixing are indicated on the x-axis and are depicted as LNP:NaOAc (v:v). The physiochemical properties were measured after concentration and overnight storage subsequent to dialysis.

Figure 9:
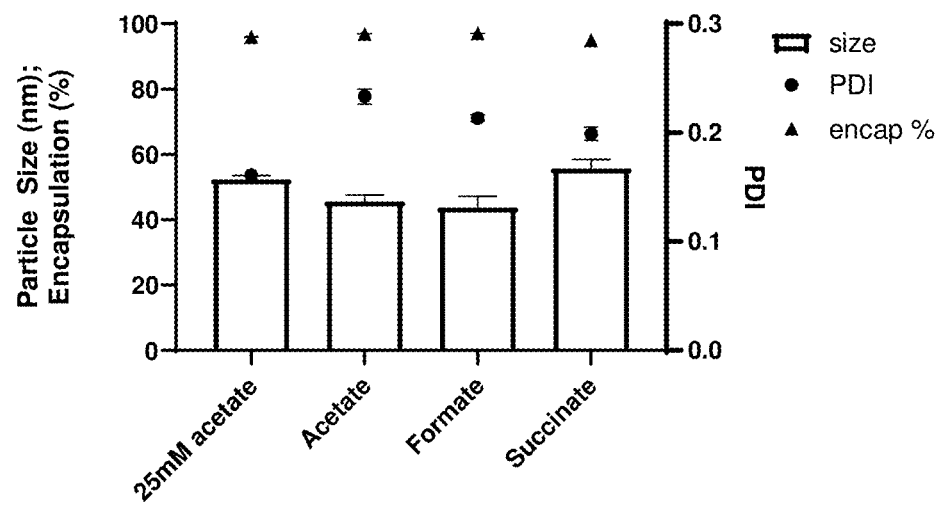

FIG. 9 is a graph showing entrapment (%), particle size (nm) and PDI of pDNA-LNPs containing no PEG and formulated with 1 ionizable lipid using the unmodified ethanol mixing method (no dilution) with 25 mM sodium acetate (NaOAc), 50 mM sodium acetate, 50 mM sodium formate and 50 mM sodium succinate. The formulations were 1/DSPC/cholesterol (27.4/50/22.6 mol/mol). The nitrogen-to-phosphate (N/P) ratio was 9.

Figure 10A:
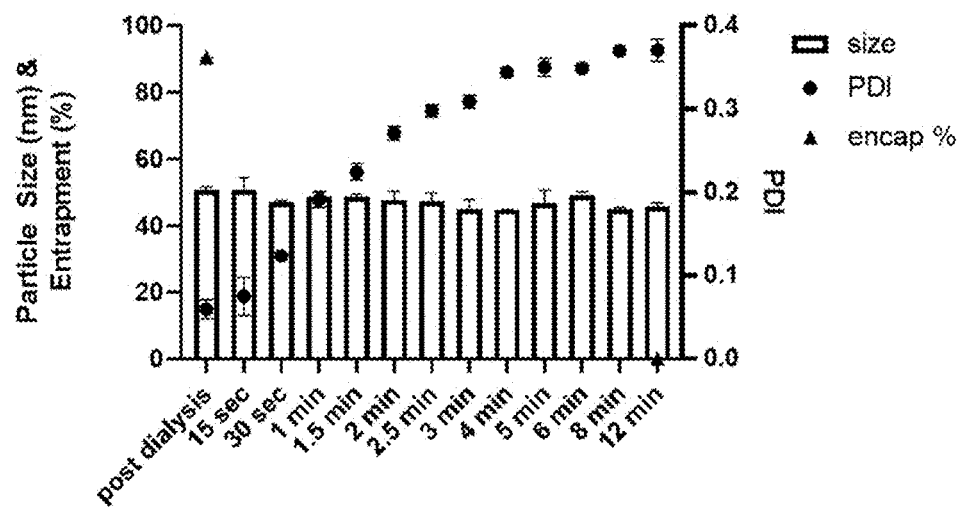

FIG. 10A is a graph showing entrapment (%), particle size (nm) and PDI of mRNA-LNPs containing ionizable lipid 1/DSPC/chol/PEG$_{2000}$-DMG (27.4/50/21.1/1.5) and formulated with 1 ionizable lipid following vortexing. The nitrogen-to-phosphate (N/P) ratio was 9.

Figure 10B:
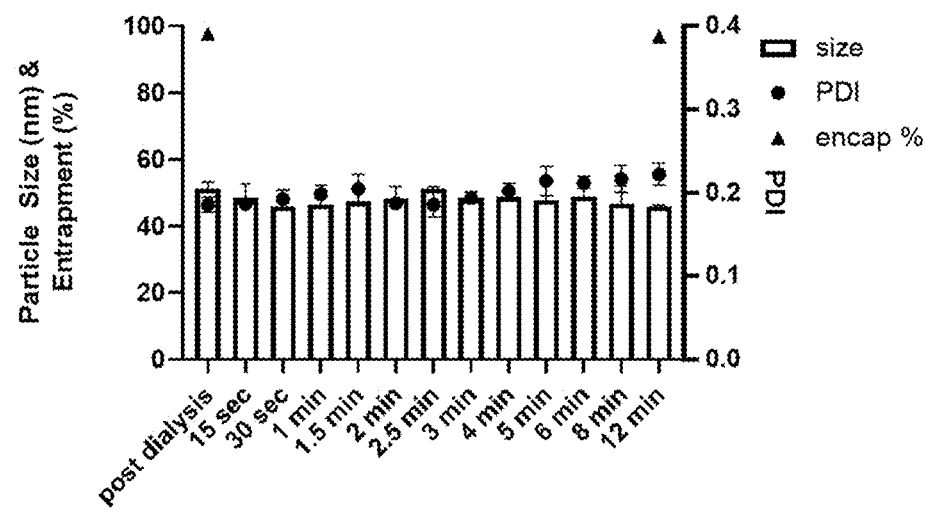

FIG. 10B is graph showing entrapment (%), particle size (nm) and PDI of mRNA-LNPs containing ionizable lipid 1/DSPC/chol (27.4/50/22.6) and formulated with 1 ionizable lipid following vortexing. The nitrogen-to-phosphate (N/P) ratio was 9.

Figure 11A:
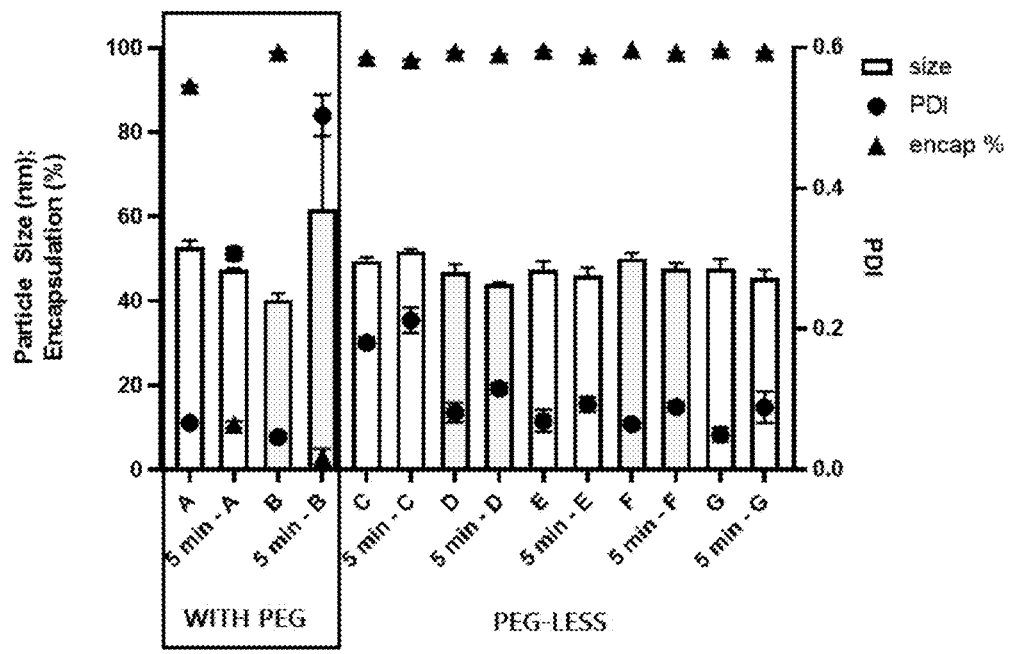

FIG. 11A is a graph showing entrapment (%), particle size (nm) and PDI of PEG-containing mRNA-LNPs composed of 1/DSPC/chol/PEG$_{2000}$-DMG (27.4/50/21.1/1.5) and PEG-less LNPs composed of ionizable lipid 1/DSPC/chol at the various molar ratios set forth in Table 6 before and after vortexing. The nitrogen-to-phosphate (N/P) ratio was 9.

Figure 11B:
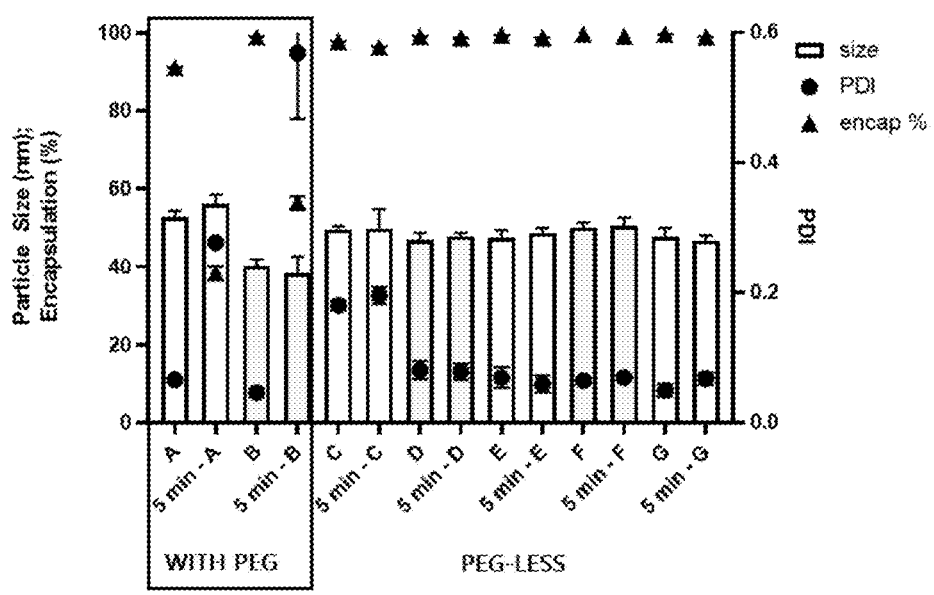

FIG. 11B is a graph showing entrapment (%), particle size (nm) and PDI of PEG-containing mRNA-LNPs composed of 1/DSPC/chol/PEG$_{2000}$-DMG (27.4/50/21.1/1.5) and PEG-less LNPs composed of ionizable lipid 1/DSPC/chol at the various molar ratios set forth in Table 6 before and after introduction of an air stream. The nitrogen-to-phosphate (N/P) ratio was 9.

Figure 12A:
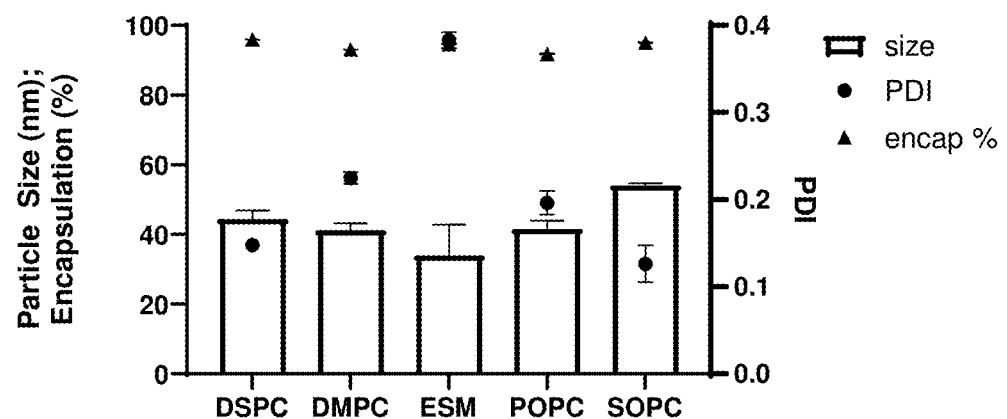

FIG. 12A is a graph showing entrapment (%), particle size (nm) and PDI of mRNA-LNPs containing no PEG and formulated with 1 ionizable lipid using different structural lipids having choline head groups, namely DSPC, dimyristoylphosphatidylcholine (DMPC), egg sphingomyelin (ESM), 1-palmitoyl-2-oleoylphosphatidylcholine (POPC) and 1-stearoyl-2-oleoylphosphatidylcholine (SOPC). The formulations were 1/structural lipid/cholesterol (27.4/50/22.6 mol/mol) and were prepared using an unmodified ethanol mixing method. The nitrogen-to-phosphate (N/P) ratio was 9. The physiochemical properties were measured after dialysis.

Figure 12B:
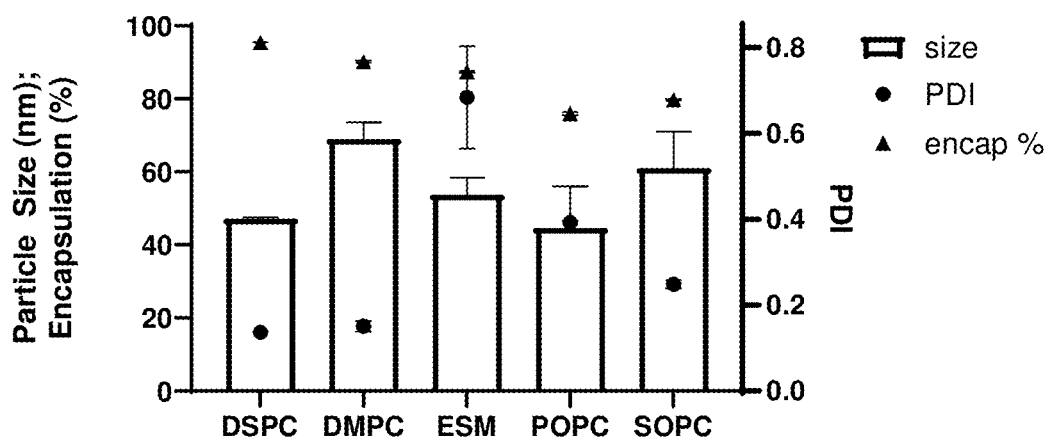

FIG. 12B is a graph showing entrapment (%), particle size (nm) and PDI of mRNA-LNPs containing no PEG and formulated with 1 ionizable lipid using different structural lipids having choline head groups, namely DSPC, DMPC, ESM, POPC and SOPC. The formulations were 1/structural lipid/cholesterol (27.4/50/22.6 mol/mol) and were prepared using an unmodified ethanol mixing method. The nitrogen-to-phosphate (N/P) ratio was 9. The physiochemical properties were measured after concentration and overnight storage subsequent to dialysis.

Figure 13:
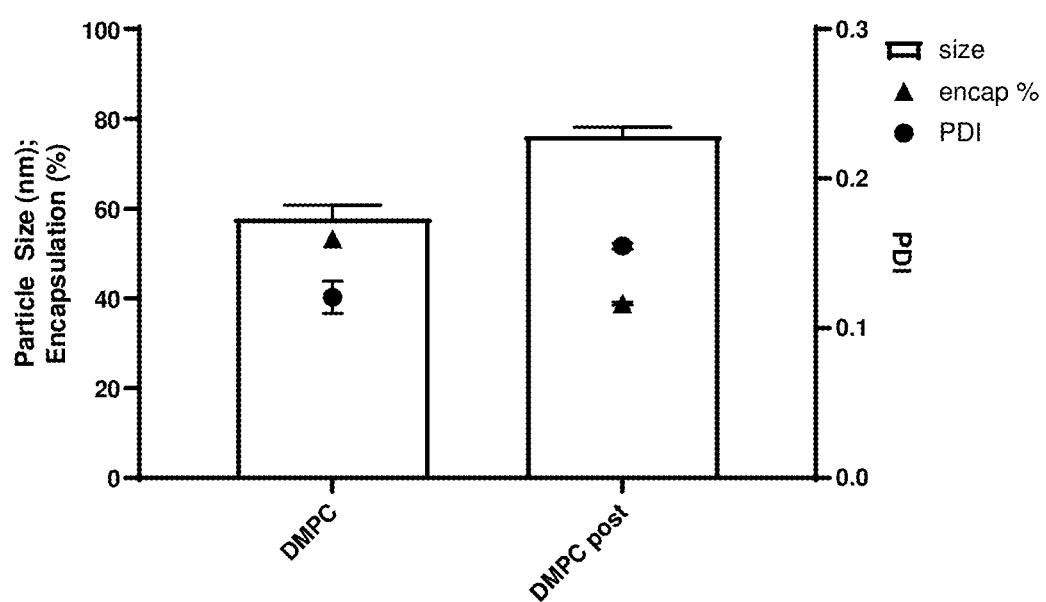

FIG. 13 is a graph showing entrapment (%), particle size (nm) and PDI of mRNA-LNPs containing no PEG and formulated with 12 ionizable lipid. The formulations were 12 ionizable lipid/DMPC/cholesterol (27.4/50/22.6 mol/mol) and were prepared using an unmodified ethanol mixing method. The nitrogen-to-phosphate (N/P) ratio was 9.

Figure 14A:
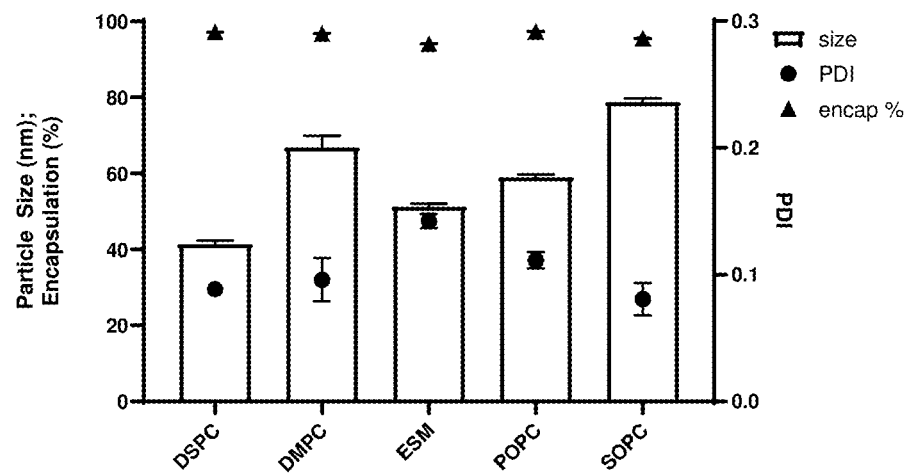

FIG. 14A is a graph showing entrapment (%), particle size (nm) and PDI of mRNA-LNPs containing no PEG and formulated with 1 ionizable lipid using different structural lipids having choline head groups, namely DSPC, DMPC, ESM, POPC and SOPC. The formulations were 1/structural lipid/cholesterol (33.05/40/26.95 mol/mol) and were prepared using an unmodified ethanol mixing method. The nitrogen-to-phosphate (N/P) ratio was 9. The physiochemical properties were measured after dialysis.

Figure 14B:
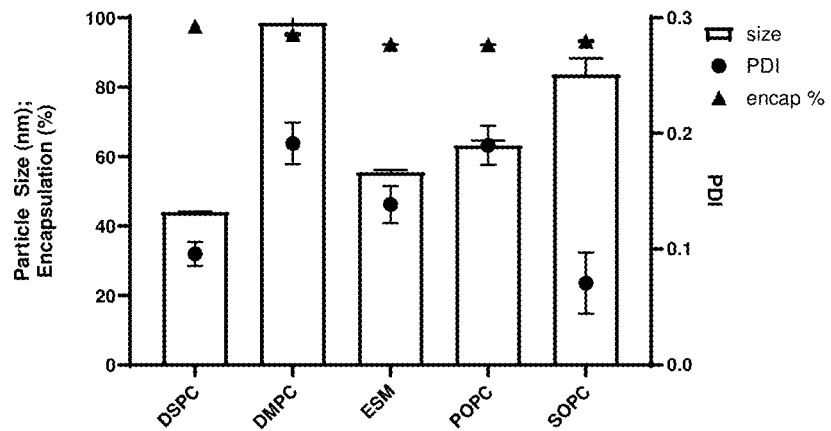

FIG. 14B is a graph showing entrapment (%), particle size (nm) and PDI of mRNA-LNPs containing no PEG and formulated with 1 ionizable lipid using different structural lipids having choline head groups, namely DSPC, DMPC, ESM, POPC and SOPC. The formulations were 1/structural lipid/cholesterol (33.05/40/26.95 mol/mol) and were prepared using an unmodified ethanol mixing method. The nitrogen-to-phosphate (N/P) ratio was 9. The physiochemical properties were measured after concentration and overnight storage subsequent to dialysis.

Figure 15:
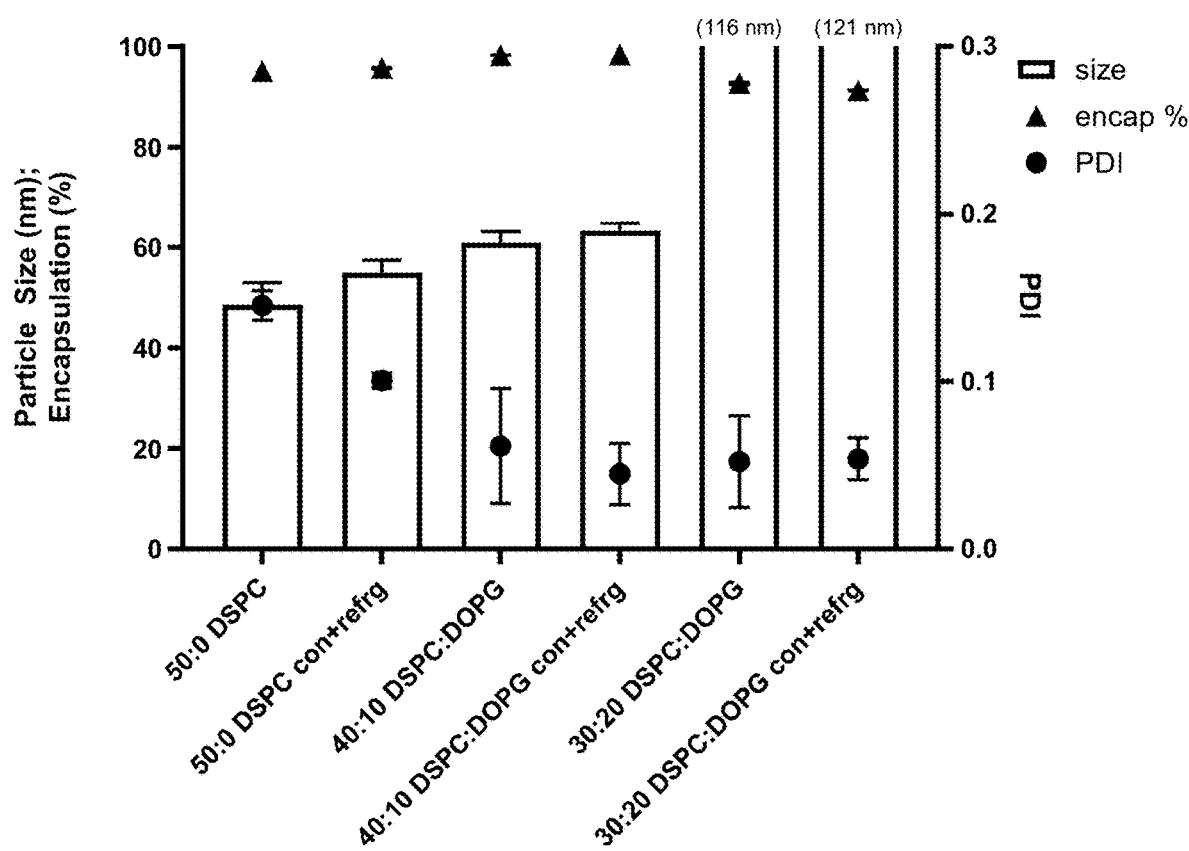

FIG. 15 is a graph showing entrapment (%), particle size (nm) and PDI of pDNA-LNPs containing no PEG and formulated with 1 ionizable lipid using different ratios of DSPC and dioleoylphosphatidylglycerol (DOPG) structural lipids. The formulations were 1/DSPC+DOPG/cholesterol (27.4/50/22.6 mol/mol) and were prepared using an unmodified ethanol mixing method (see Table 7 of Example 9). The combined DSPC+DOPG content was 50 mol % with DSPC present at 30 mol %, 40 mol % and 50 mol % and the balance being DOPG. The nitrogen-to-phosphate (N/P) ratio was 9. The results show physiochemical properties before (after dialysis) and after (post) concentration and storage of the LNPs.

Figure 16:
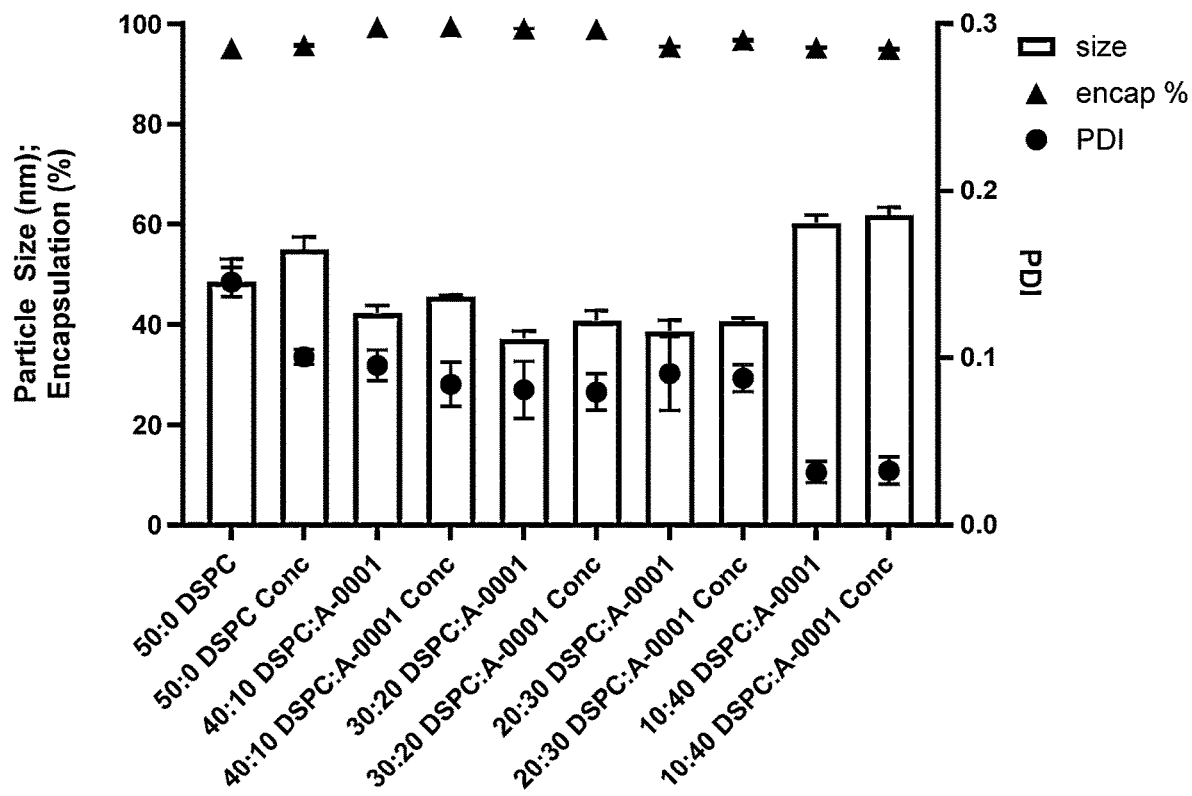

FIG. 16 is a graph showing entrapment (%), particle size (nm) and PDI of pDNA-LNPs containing no PEG and formulated with 1 ionizable lipid using different ratios of DSPC and A-0001 lipid set forth in Example 9 (see Table 8). The formulations were 1/DSPC+A0001/cholesterol (27.4/50/22.6 mol/mol) and were prepared using an unmodified ethanol mixing method. The combined DSPC+A0001 content was 50 mol % with DSPC was present at 10 mol %, 20 mol %, 30 mol %, 40 mol % and 50 mol % with the balance being A0001. The nitrogen-to-phosphate (N/P) ratio was 9.

Figure 17:
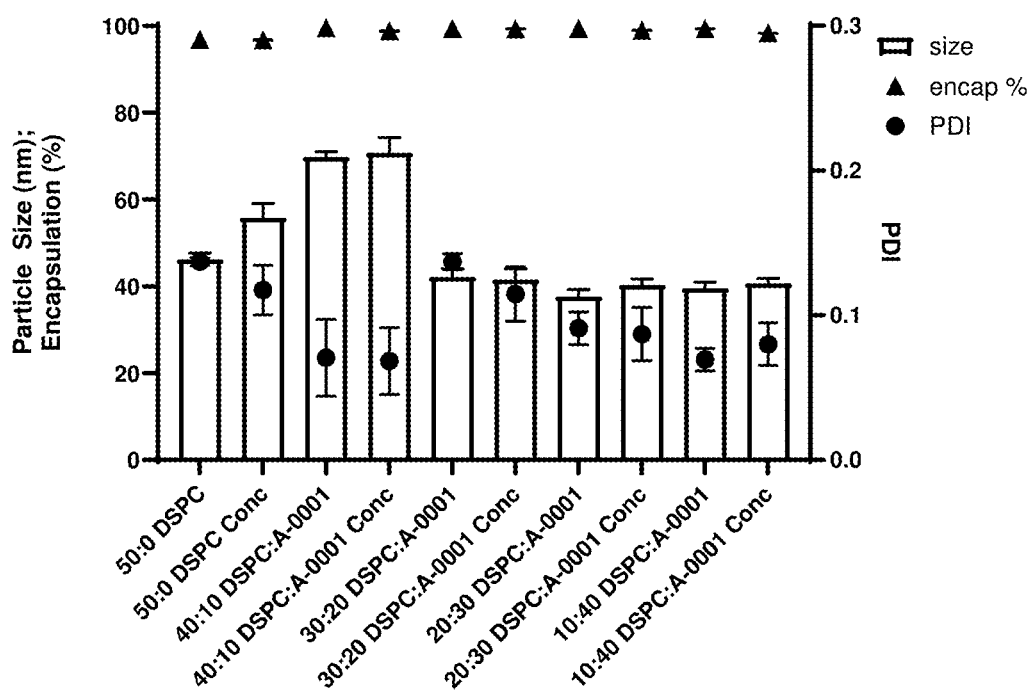

FIG. 17 is a graph showing entrapment (%), particle size (nm) and PDI of mRNA-LNPs containing no PEG and formulated with 1 ionizable lipid using different ratios of DSPC and A-0001 lipid set forth in Example 9 (see Table 9). The formulations were prepared using an unmodified ethanol mixing method. The combined DSPC+DOPG or DSPC+A0001 content was 50 mol % with DSPC was present at 10 mol %, 20 mol %, 30 mol %, 40 mol % and 50 mol % with the balance being DOPG or A0001 (see Table 9). The nitrogen-to-phosphate (N/P) ratio was 9.

Figure 18:
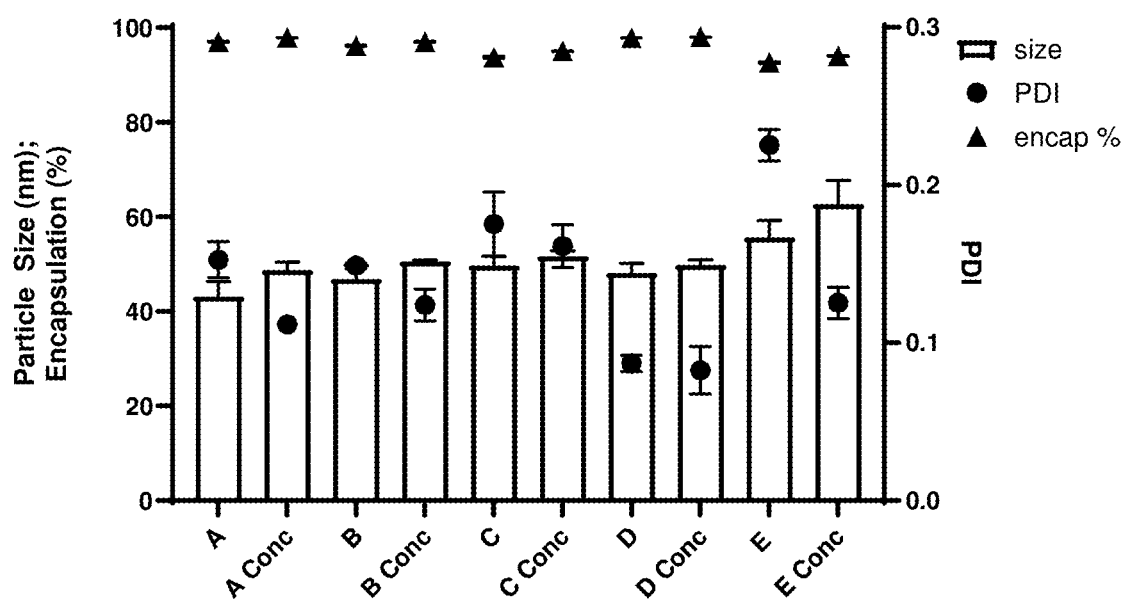

FIG. 18 is a graph showing entrapment (%), particle size (nm) and PDI of mRNA-LNPs containing no PEG and formulated with 1 ionizable lipid using various mole percentages of DSPC (40, 50 and 60 mol %; see Example 10, Table 10). Various formulations with 50 mol % DSPC were prepared with different amounts of ionizable lipid and cholesterol (see Example 10, Table 10 for formulation mol %). The formulations were 1/DSPC/cholesterol and DSPC was present at 50 mol % (LNP A and B), 40 mol % (LNP C), 50 mol % DSPC (LNP D) and 60 mol % DSP (LNP E) and were prepared using an unmodified ethanol mixing method.

Figure 19A:
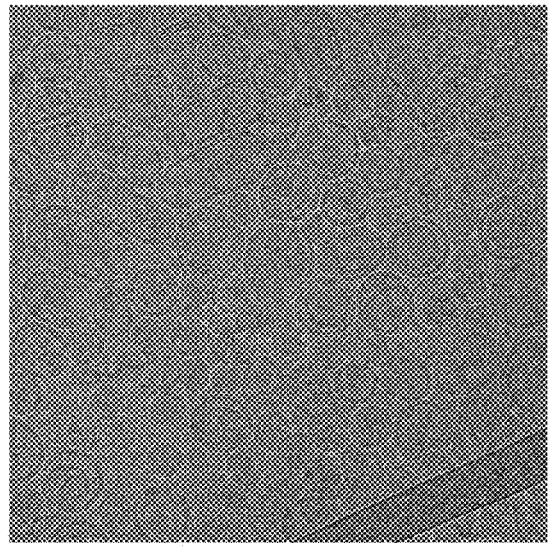

FIG. 19A is a cryo-TEM image of a lipid nanoparticle preparation of 1/DSPC/chol at 25/50/25 mol/mol.

Figure 19B:
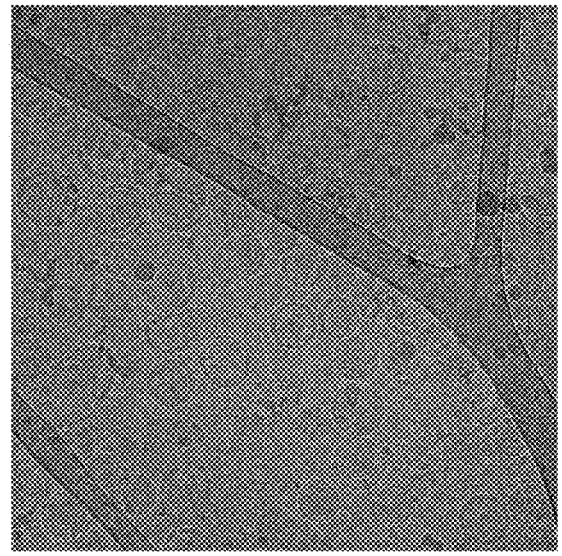

FIG. 19B is a cryo-TEM image of a lipid nanoparticle preparation of 1/DSPC/chol at 33/40/27 mol/mol.

Figure 19C:
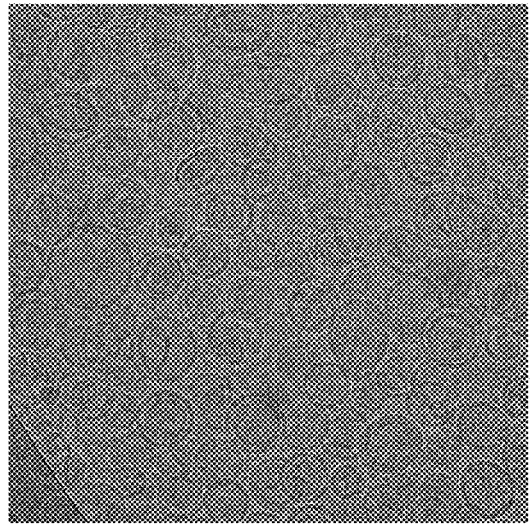

FIG. 19C is a cryo-TEM image of a lipid nanoparticle preparation of 1/DSPC/chol at 15/50/35 mol/mol.

Figure 19D:
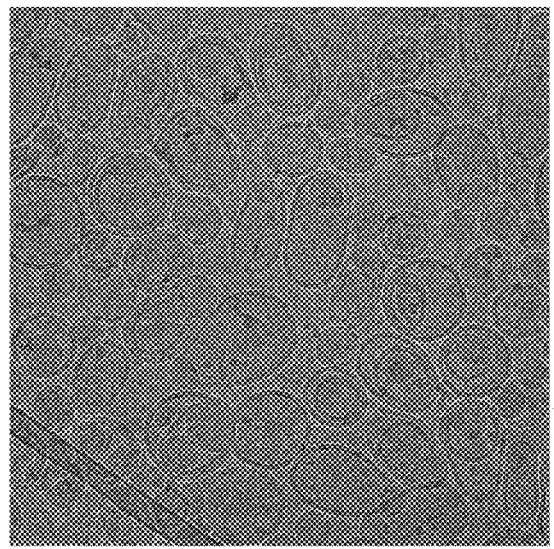

FIG. 19D is a cryo-TEM image of a lipid nanoparticle preparation of 1/DSPC/chol at 21/60/19 mol/mol.

Figure 19E:
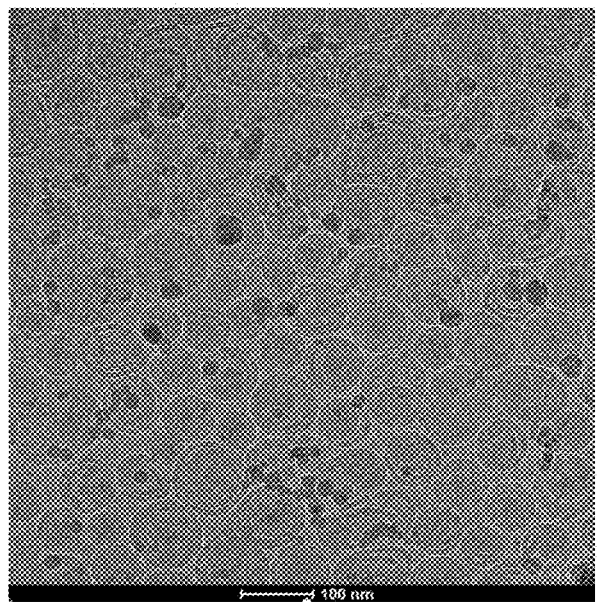

FIG. 19E is a cryo-TEM image of a lipid nanoparticle preparation of 12/DSPC/chol at 27.4/50/22.6 mol/mol.

Figure 19F:
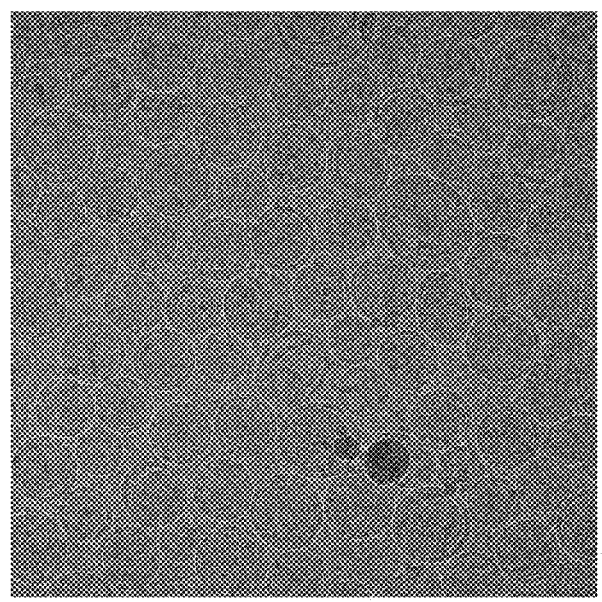

FIG. 19F is a cryo-TEM image of a lipid nanoparticle preparation of 16/DSPC/chol at 27.4/50/22.6 mol/mol.

Figure 20A:
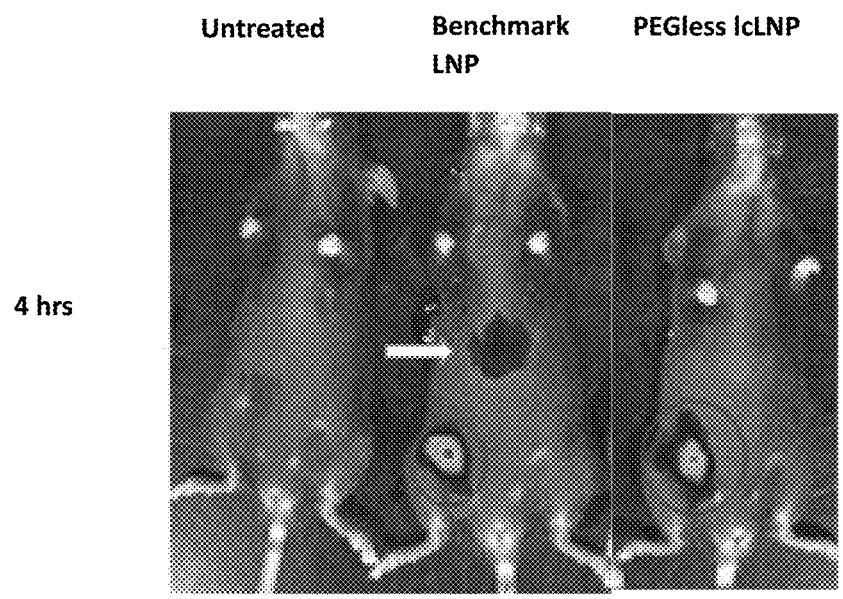

FIG. 20A shows the luciferase expression level in mice as indicated by bioluminescence imaging using Lumina II In Vivo Imaging System (IVIS®) at 4 hours post-injection with 1 mg of LNPs encapsulating luciferase mRNA having PEG (Ionizable lipid 3:DSPC:Chol:PEG$_{2000}$-DMG (27.4:50: 21.1:1.5 mol:mol)); lacking PEG (Ionizable lipid 3:DSPC: Chol (27.4:50:22.6)) ("PEGless lcLNP™"); and an untreated mouse used as a negative control. The ionizable lipid is lipid 15 of Table 3.

Figure 20B:
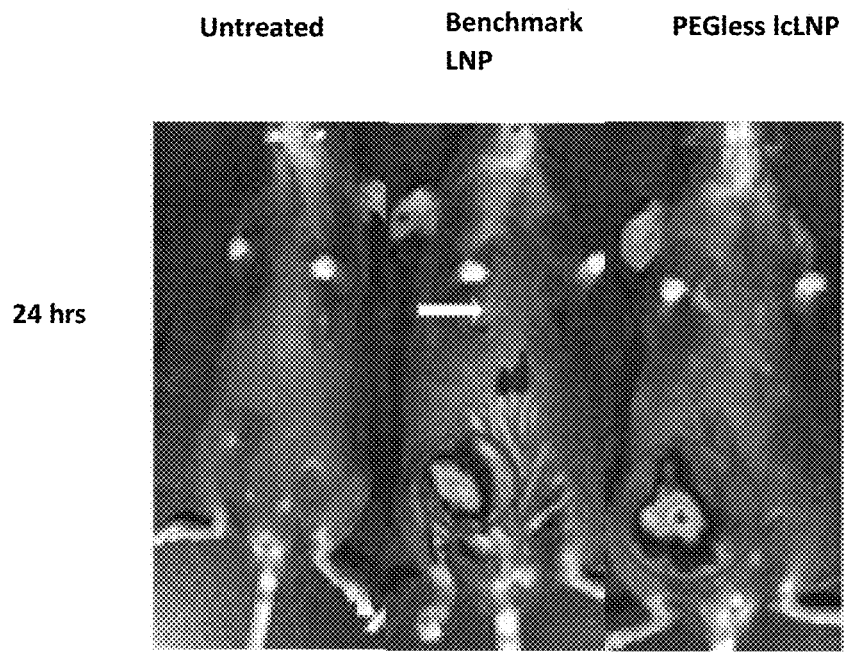

FIG. 20B shows the luciferase expression level in mice as indicated by bioluminescence imaging using the IVIS® imaging system at 24 hours post-injection of mice for the PEG-containing, PEGless formulations described in FIG. 20A and in Example 12. An untreated mouse was used as a negative control.

Figure 21A:
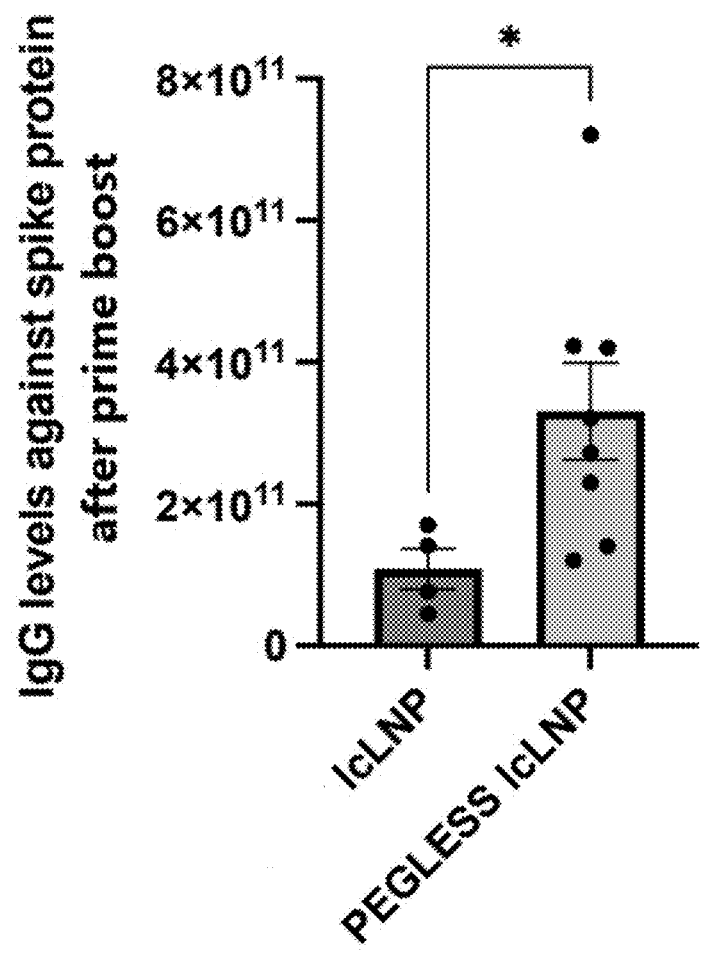

FIG. 21A shows electrochemiluminescence signals of induced IgG levels against the spike protein in mice serum as indicated at Day 35 post-injection after a prime dose at Day 0 and a boost dose at Day 21, respectively, of the following formulations: ionizable lipid 3:DSPC:Chol: PEG$_{2000}$-DMG (27.4:50:21.1:1.5, mol:mol) or ionizable lipid 15:DSPC:Chol (27.4:50:22.6 mol:mol). Each formulation comprises mRNA encoding for the Sars-Cov2 spike protein.

Figure 21B:
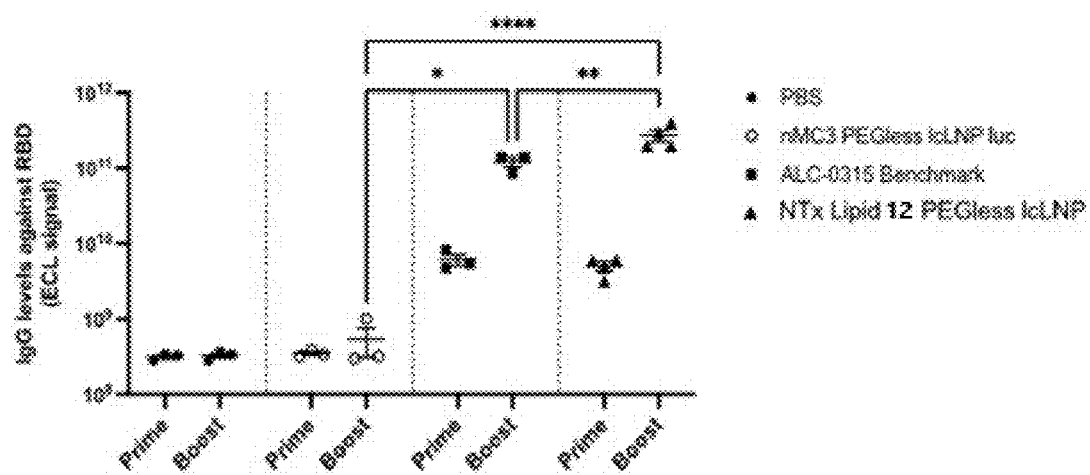

FIG. 21B shows the electrochemiluminescence signals of the induced IgG levels against the spike protein in mice serum as indicated at Day 35 post-injection after a prime dose at Day 0 and a boost dose at Day 21, respectively, of the following formulations: Nor MC3:DSPC:Chol (27.4:50: 22.6, mol:mol encapsulating luciferase; ALC-0315:DSPC: Chol:PEG$_{2000}$-DMG (27.4:50:21.1:1.5, mol:mol) encapsulating mRNA for Sars-Cov2 spike protein; and ionizable lipid 12:DSPC:Chol (27.4:50:22.6, mol:mol) encapsulating mRNA for Sars-Cov2 spike protein (see also Table 14).

Figure 21C:
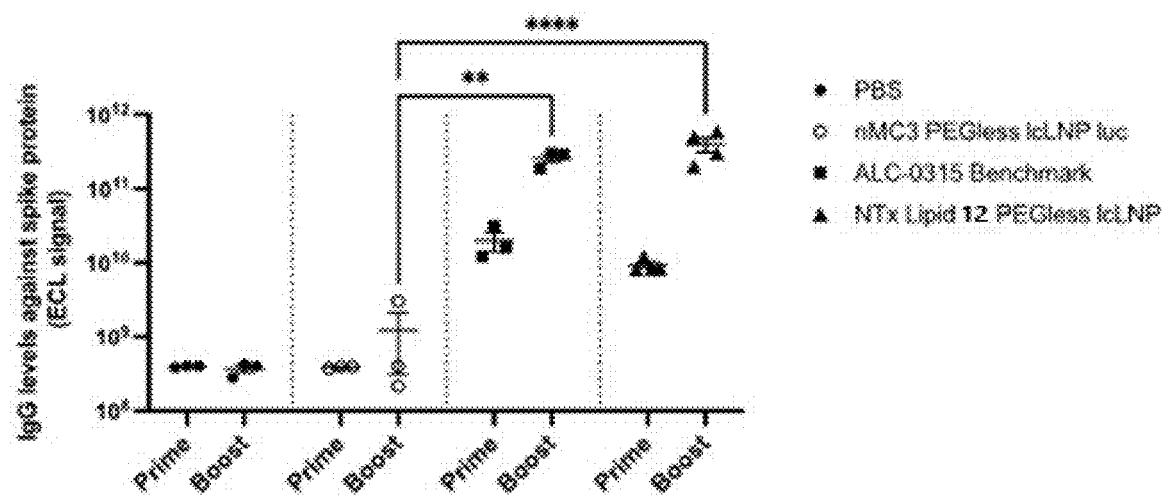

FIG. 21C shows the electrochemiluminescence signals of the induced IgG levels against receptor binding protein (RBC) in mice serum as indicated at Day 35 post-injection after a prime dose at Day 0 and a boost dose at Day 21, respectively, of the formulations set out in FIG. 4B above (see also Table 14).

Figure 22A:
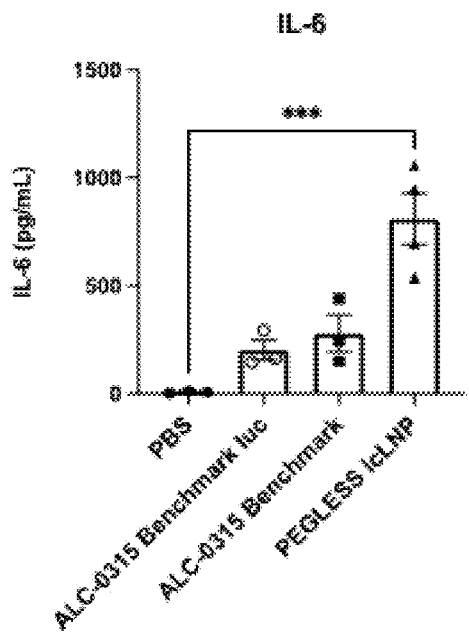

FIG. 22A shows the interleukin-6 (IL-6) pg/mL in mice measured ex vivo as indicated at 6 hours post-injection after a prime dose at Day 0 of the following two PEG-containing baselines and PEGless formulation: ALC-0315:DSPC:Chol: PEG$_{2000}$-DMG (50:10:38.5:1.5 mol:mol) containing mRNA encoding luciferase (ALC 50/10 luc); ALC-0315:DSPC: Chol:PEG$_{2000}$-DMG (27.4:50:21.1:1.5 mol:mol) containing mRNA coding for SARS-CoV2 Spike Protein (ALC 50/10); and ionizable lipid 12:DSPC:Chol (Ionizable lipid 12:DSPC:Chol (27.4:50:22.6 mol:mol) containing mRNA coding for SARS-CoV2 Spike protein. A mouse treated with phosphate buffered saline (PBS) was used as a negative control. The formulations and ionizable lipids are described in described in Table 15.

Figure 22B:
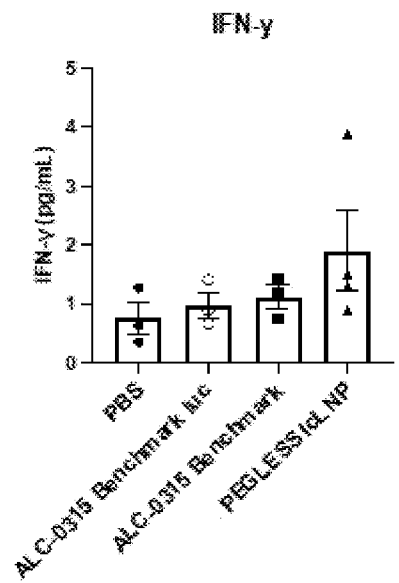

FIG. 22B shows the interferon gamma (IFN-γ) pg/mL in mice measured ex vivo at 6 hours after the prime dose of the same formulations and negative control as described in FIG. 22A (see also Table 15) encapsulating mRNA encoding luciferase or SARS-CoV2.

Figure 22C:
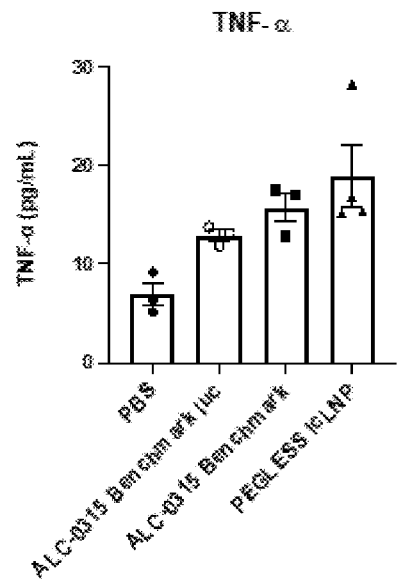

FIG. 22C shows the interferon gamma (TNF-α) pg/mL in mice measured ex vivo at 6 hours after the prime dose of the same formulations and negative control as described in FIG. 22A (see also Table 15) encapsulating mRNA encoding luciferase or SARS-CoV2.

Figure 23A:
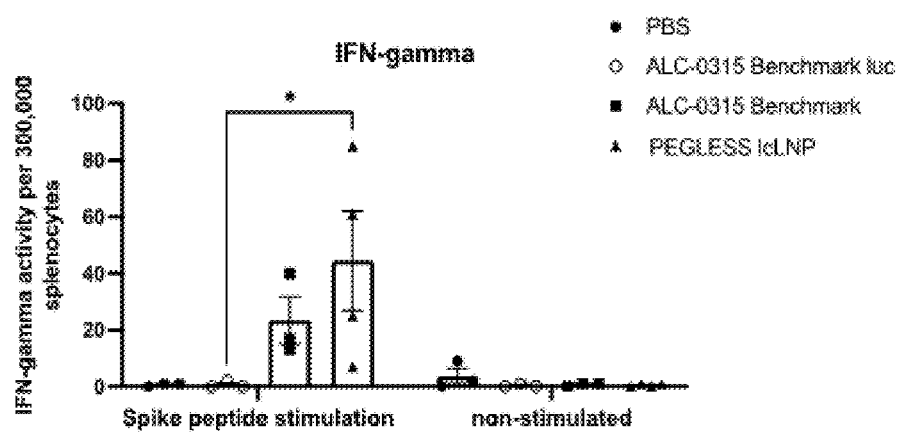

FIG. 23A shows the interferon gamma (IFN-γ) activity/ 300,000 splenocytes in mice measured ex vivo as indicated at day 35 post-injection after a prime dose at Day 0 and a boost dose at Day 21 of the of the same formulations and negative control as described in FIG. 22A (see also Table 15) encapsulating mRNA encoding luciferase or SARS-CoV2.

Figure 23B:
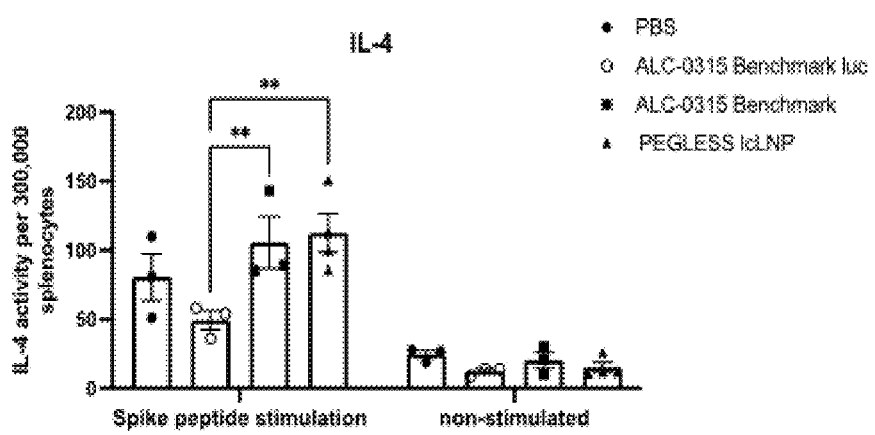

FIG. 23B shows the interleukin-4 (IL-4) activity/300,000 splenocytes in mice measured ex vivo as indicated at day 35 post-injection after the prime dose and booster of the same formulations and negative control as described in FIG. 22A encapsulating mRNA encoding luciferase or SARS-CoV2 RBD (see also Table 15).

Figure 24A:
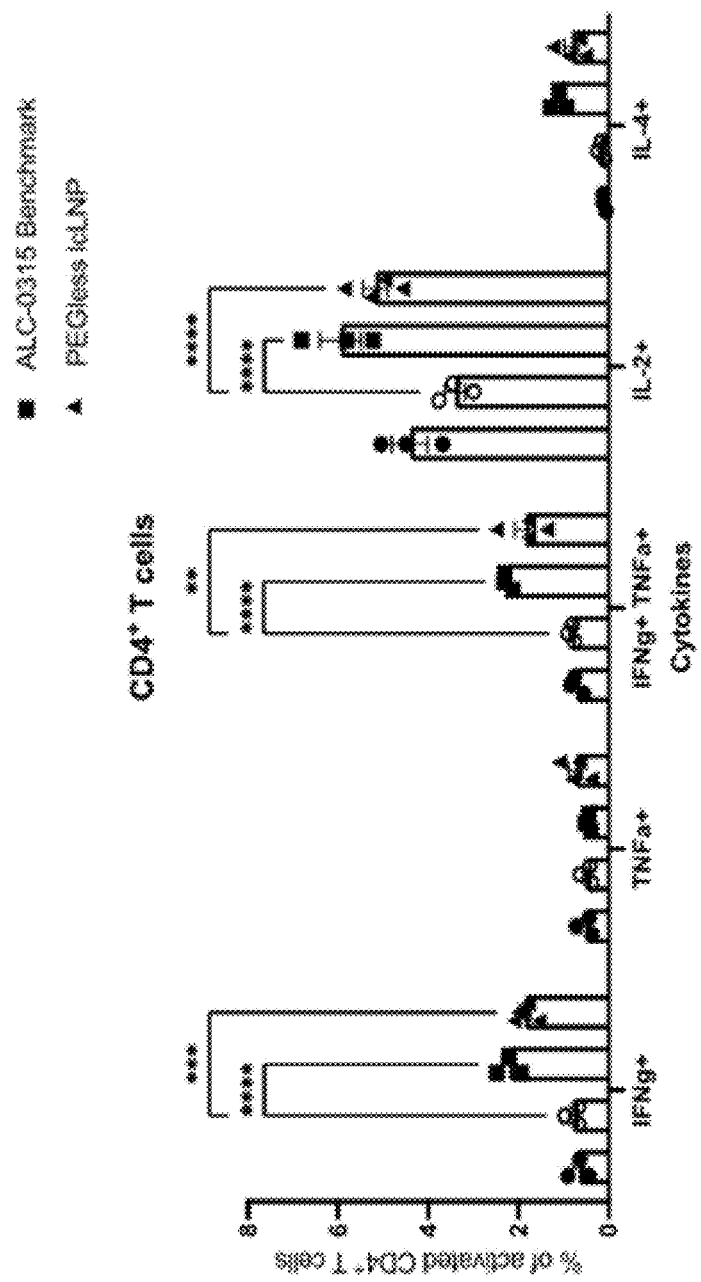

FIG. 24A shows the percentage of activated CD4$^+$ cells positive for various T-helper type 1 (TH-type 1) cytokines of mice measured ex vivo, namely interferon gamma (IFN-γ+), tumour necrosis factor alpha (TNF-α+), IFN-γ+ and TNF-α+, interleukin-2 (Il-2+) and minute levels of T helper type 2 (TH-type 2) cytokine interleukin-4 (IL-4+)) at Day 35 post-injection after a prime dose at Day 0 and a boost dose at Day 21. The same formulations were injected as in FIG. 22A (see also Table 15) with mRNA encoding luciferase or SARS-CoV2 Spike protein. The negative control was PBS treated mice.

Figure 24B:
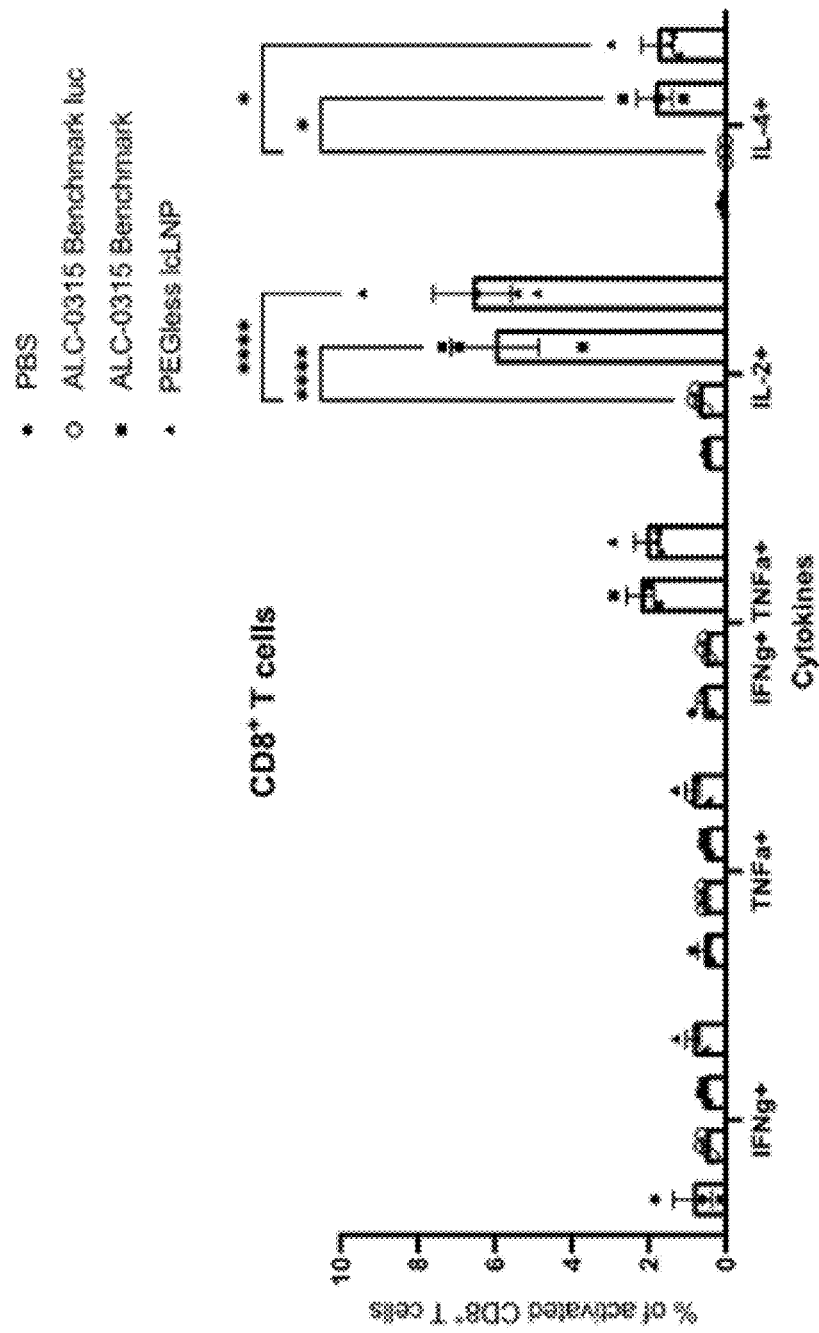

FIG. 24B shows the percentage of activated CD8$^+$ cells positive for various type 1 cytokines in mice measured ex vivo as indicated (IFN-γ+, TNF-α+, IFN-γ+ and TNF-α+, Il-2+) and type 2 cytokine IL-4+ at Day 35 post-injection after a prime dose at Day 0 and a boost dose at Day 21. The same formulations and PBS (negative control) were injected as in FIG. 22A (see also Table 15) encapsulating mRNA encoding luciferase or SARS-CoV2 Spike protein.

Figure 25A:
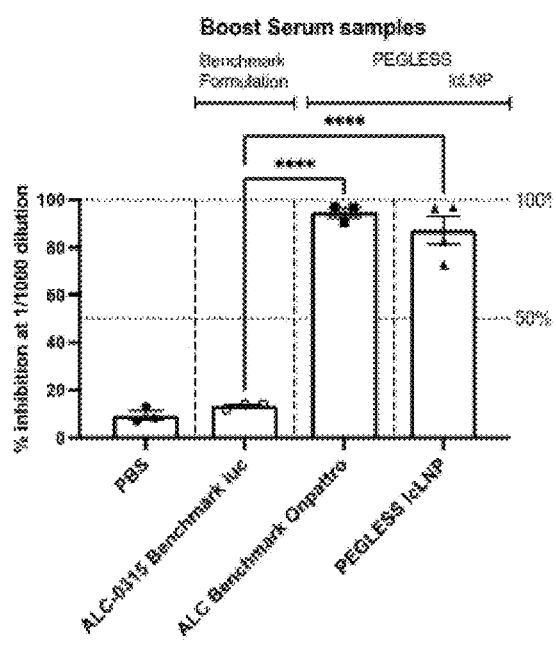

FIG. 25A shows the percentage inhibition of functional antibody ex vivo that inhibits ACE2 binding to SARS CoV-2 RBD (at 1/300 dilution) in the serum of mice after a prime dose at Day 0. The same formulations were injected as in FIG. 22A (see also Table 15) encapsulating mRNA encoding luciferase or SARS-CoV2 Spike protein. The negative control was PBS treated mice.

Figure 25B:
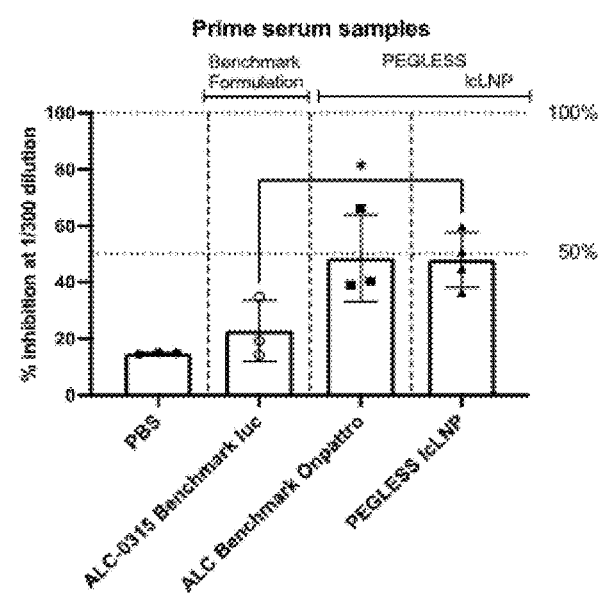

FIG. 25B shows the percentage inhibition of functional antibody ex vivo that inhibits ACE2 binding to SARS CoV-2 RBD (at 1/1000 dilution) in the serum of mice after a boost dose at Day 21. The same formulations and PBS (negative control) were injected as in FIG. 22A (see also Table 15) encapsulating mRNA encoding luciferase or SARS-CoV2 Spike protein.

Figures 26A, 26B:
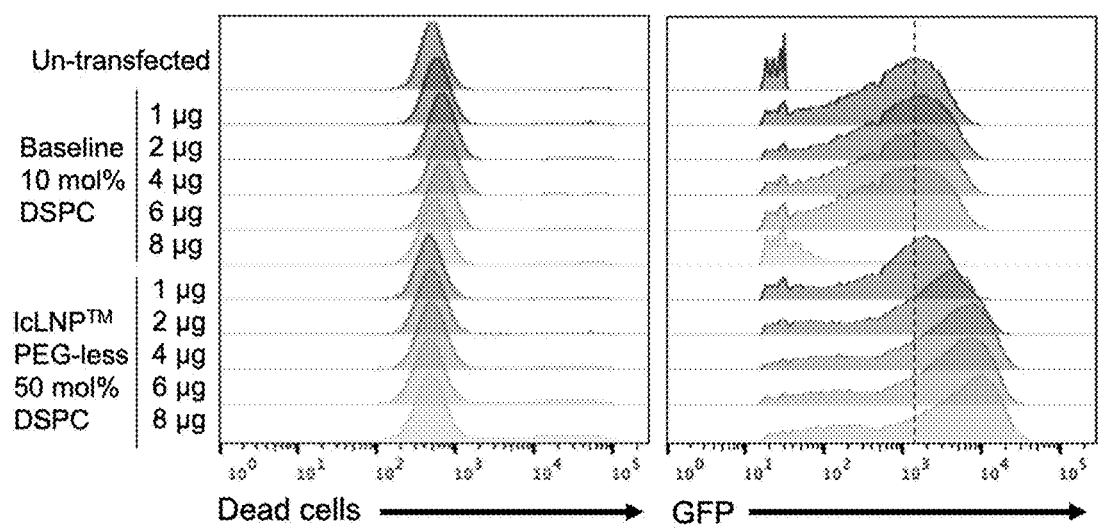

FIG. 26A shows flow cytometry data for untreated and LNP-treated primary human CD8+ T cells staining for dead cells at 48 hours post treatment. The LNPs examined encapsulate mRNA encoding for eGFP and contained 10 mol % DSPC (nMC3:DSPC:Chol:PEG$_{2000}$-DMG-lipid (50:10:38.5:1.5 mol:mol) (Baseline)); or were unshielded LNPs (ionizable cationic lipid:DSPC:Chol (28.15:50:21.85 mol:mol) ("lcLNP™-PEG-less) and were titrated at doses of 1, 2, 4, 6 and 8 μg. The ionizable cationic lipids used in the lcLNP™ compositions were 1 and 15 as described in Table 16 of Example 18.

FIG. 26B shows flow cytometry data for untreated and LNP-treated primary human CD8+ T cells quantifying for green fluorescent protein (GFP) expression at 48 hours post treatment. The LNP formulations are the baseline and unshielded lcLNP™ formulations described in Table 16 of Example 18.

Figure 27:
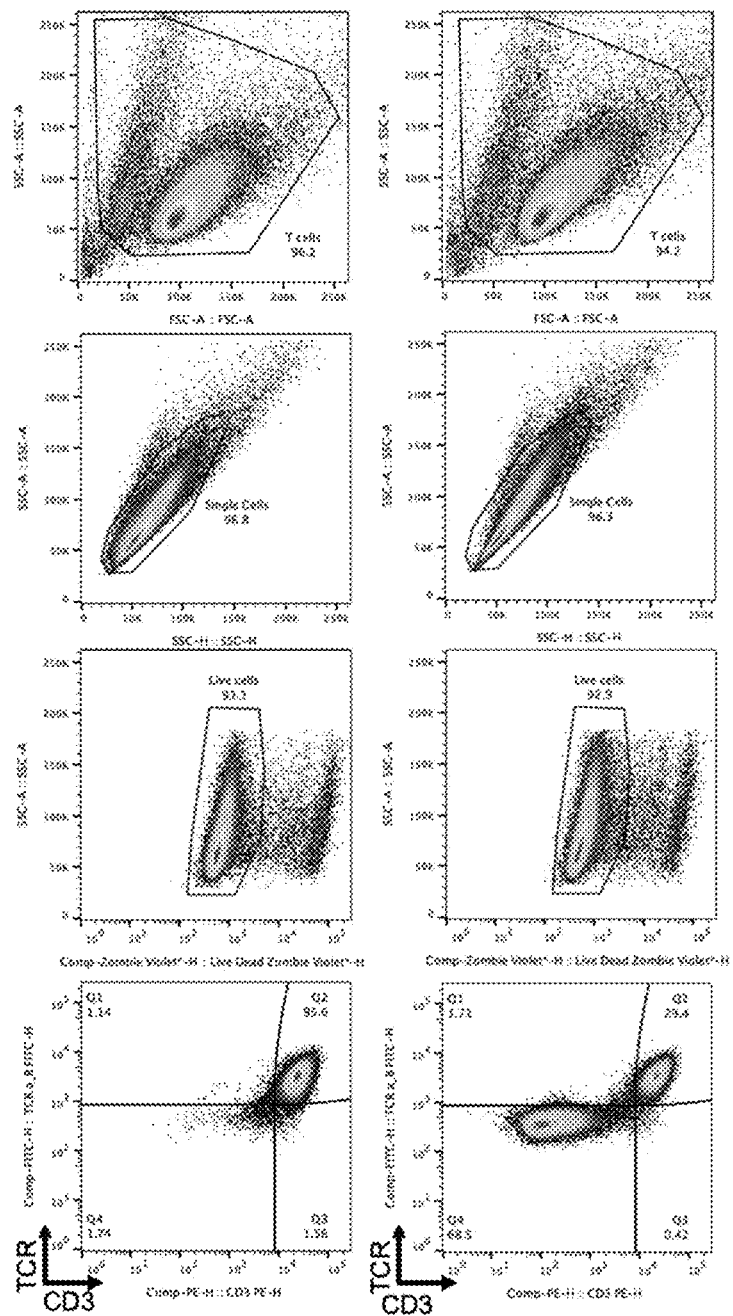

FIG. 27 shows ex vivo representative flow cytometry gating strategy for TCR/CD3 for the flow cytometry data of FIGS. 28 and 29 below.

Figure 28A:
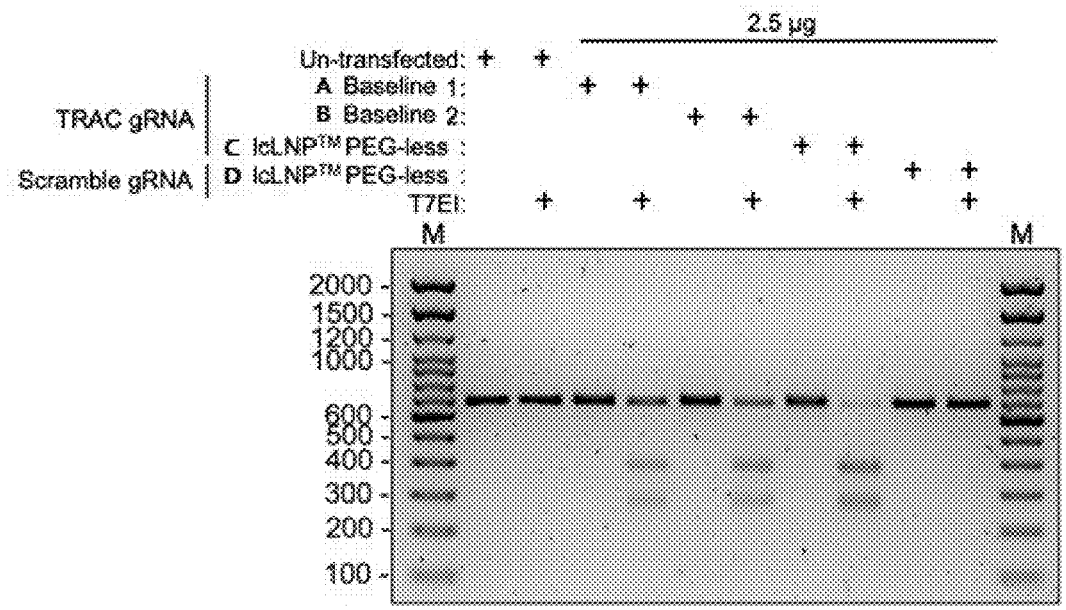

FIG. 28A depicts a gel showing genomic DNA undigested and digested with T7 endonuclease (T7EI) after treatment of CD8+ T cells ex vivo with LNP formulations encapsulating mRNA encoding Cas9 and T cell receptor a constant (TRAC) gRNA or scrambled gRNA at a dose of 2.5 μg. The LNPs examined were baseline 1, composed of ionizable lipid 1:DSPC:Chol:PEG$_{2000}$-DMG (50:10:38.5:1.5 mol:mol); baseline 2, ionizable lipid 15:DSPC:Chol:PEG$_{2000}$-DMG (50:10:38.5:1.5 mol:mol); lcLNP™ PEG-less, ionizable lipid 15:DSPC:Chol (28.15:50:21.85 mol:mol); and lcLNP™ PEG-less, with scrambled gRNA composed of ionizable lipid 15:DSPC:Chol (28.15:50:21.85 mol:mol). The ionizable cationic lipids used in the lcLNP™ compositions were lipids 1 and 15 as described in Table 18 of Example 19.

Figure 28B:
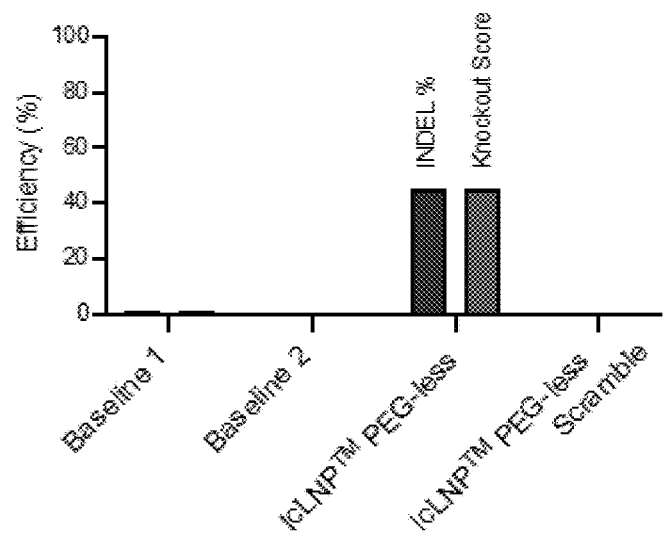

FIG. 28B is a graph showing ex vivo efficiency (%) INDEL and knockout score for CD8+ T cells treated with the LNPs set out in FIG. 28A as well as untreated samples using Interference of CRISPR Editing (ICE) at 48 hours post-LNP treatment to the T cells.

Figure 28C:
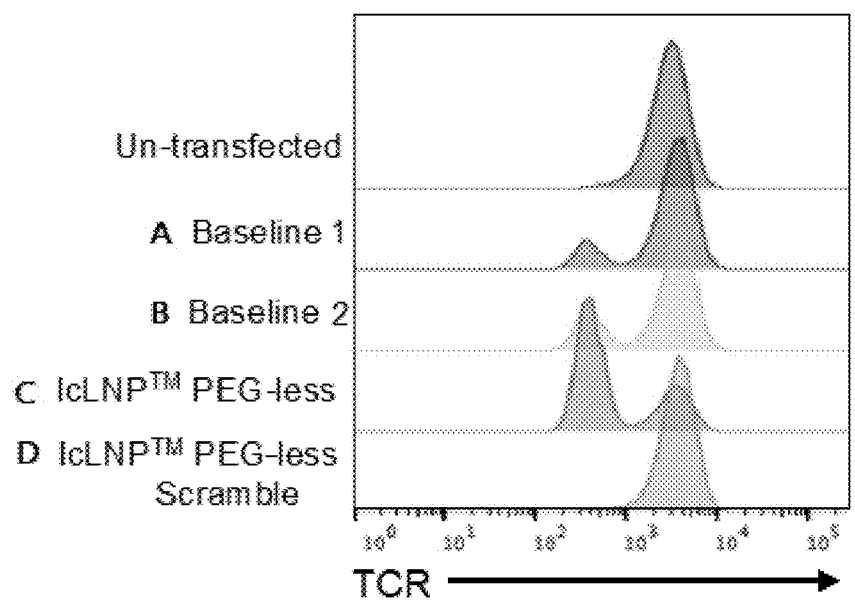

FIG. 28C is a graph showing ex vivo flow cytometry T cell receptor (TCR) data for CD8+ T cells treated with the LNPs set out in FIG. 28A as well as untreated samples at 8 days post-LNP treatment.

Figure 28D:
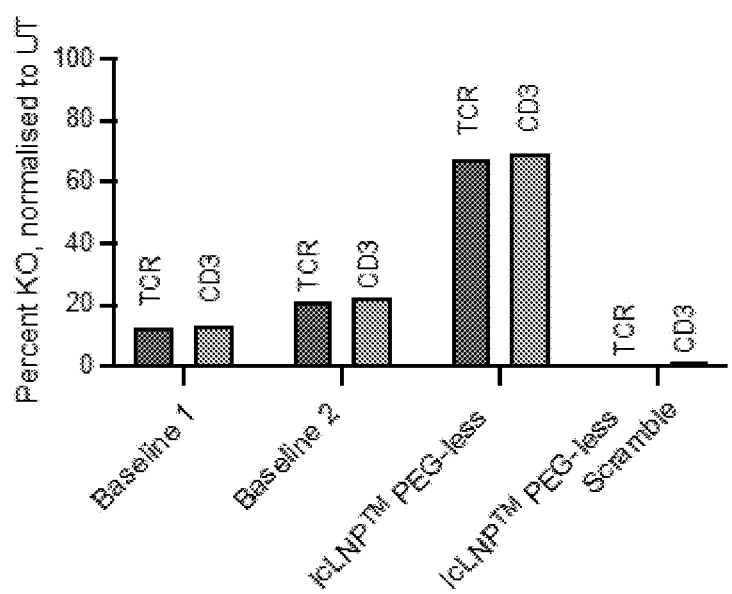

FIG. 28D is a graph showing quantification of TCR and CD3 expression ex vivo normalized to un-transfected cells by flow cytometry for CD8+ T cells treated with the LNPs set out in FIG. 28A as well as untreated samples at 8 days post-LNP treatment.

Figure 29A:
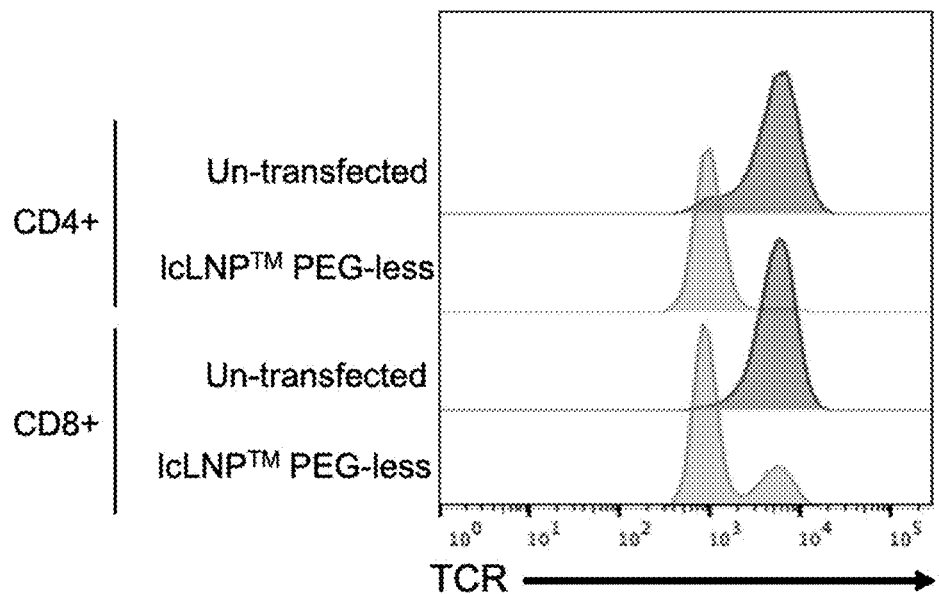

FIG. 29A is a graph showing ex vivo T cell receptor (TCR) expression by flow cytometry 8 days post LNP treatment in primary human CD4+ and CD8+ cells treated with unshielded lcLNP™ (PEG-less LNP) having ionizable lipid 15:DSPC:Chol (28.15:50:21.85 mol:mol) encapsulating Cas9 and TRAC gRNA. Ionizable lipid 15 is set forth in Table 18 of Example 19.

Figure 29B:
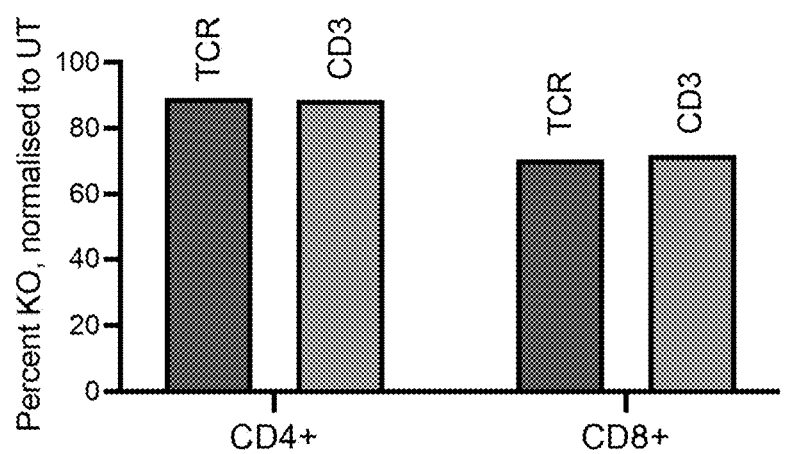

FIG. 29B is a graph showing quantification of TCR and CD3 expression normalized to un-transfected samples by the flow cytometry comparing CD4+ and CD8+ T cells treated with unshielded lcLNP™ (PEG-less LNP) having ionizable lipid 15:DSPC:Chol (28.15:50:21.85 mol:mol) encapsulating Cas9 and TRAC gRNA. Ionizable lipid 15 is set forth in Table 18 of Example 19.

FIG. 30A depicts the homology directed repair (HDR) template comprising a sequence encoding eGFP flanked by left homology arm (LHA) and right homology arm (RHA) sequences.

FIG. 30B shows flow cytometry data for un-transfected primary human CD4+ T cells in the ex vivo knock-out/knock-in study set forth in Example 21.

FIG. 30C shows flow cytometry data for primary human CD4+ T cells treated with lcLNP™ with Cas9 mRNA:TCR gRNA (1:1 wt:wt) in the ex vivo knock-out/knock-in study set forth in Example 21.

FIG. 30D shows flow cytometry data for primary human CD4+ T cells treated with lcLNP™ having Cas9 mRNA: TCR gRNA:GFP homology directed repair (HDR) (1:1:3 wt:wt) DNA in the ex vivo knock-out/knock-in study set forth in Example 21.

FIG. 30E shows flow cytometry data for primary human CD4+ T cells treated with lcLNP™ having Cas9 mRNA: TCR gRNA:GFP HDR DNA (1:1:3 wt:wt) in the ex vivo knock-out/knock-in study with inhibitor set forth in Example 21.

Figure 31A:
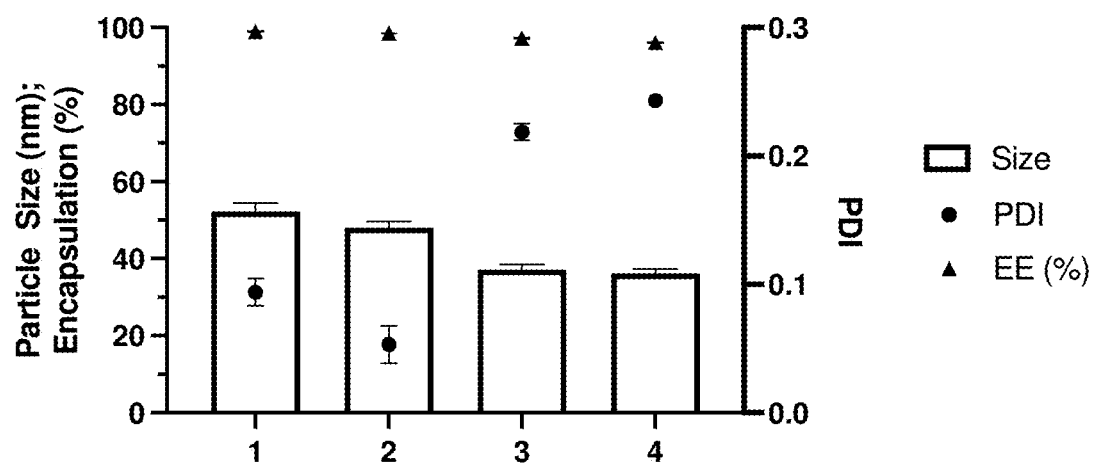

FIG. 31A shows size (nm), polydispersity (PDI) and encapsulation % of luciferase control lipid nanoparticle 1 (luciferase mRNA) composed of ionizable cationic lipid 1:DSPC:Chol (40:40:20 mol:mol), eGFP-mRNA lipid nanoparticle 2 (Onpattro™) composed of ionizable cationic lipid 1:DSPC:Chol:PEG$_{2000}$-DMG (50:10:38.5:1.5 mol:mol) or eGFP-mRNA unshielded uLNP (LNPs 3 and 4) composed of ionizable cationic lipid:DSPC:Chol (40:40:20 mol:mol). Ionizable cationic lipid 1 was used in the luciferase mRNA and Onpattro™ LNP formulations 1 and 2 and ionizable lipids 16 and 22 were used in the uLNP compositions 3 and 4 (described in Table 20 of Example 22).

Figure 31B:
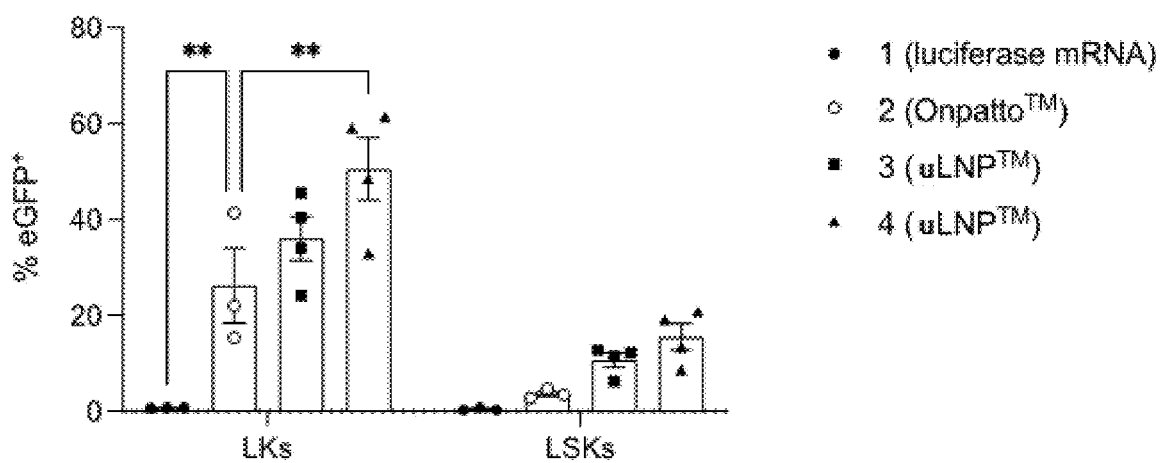

FIG. 31B shows the percentage of enhanced green fluorescent protein (eGFP) positive cells (% eGFP) in bone marrow LK (Lineage⁻c-Kit⁺) and LSK (Lineage⁻c-Kit⁺ Sca1⁺) sub-populations as indicated after 24 hours post-injection of LNP 1 (luciferase mRNA), LNP 2 eGFP-mRNA (Onpattro™) and LNPs 3 and 4 (uLNP) to C57Bl/6 mice. The LNP formulations 1 to 4 are described in FIG. 31A above.

Figure 31C:
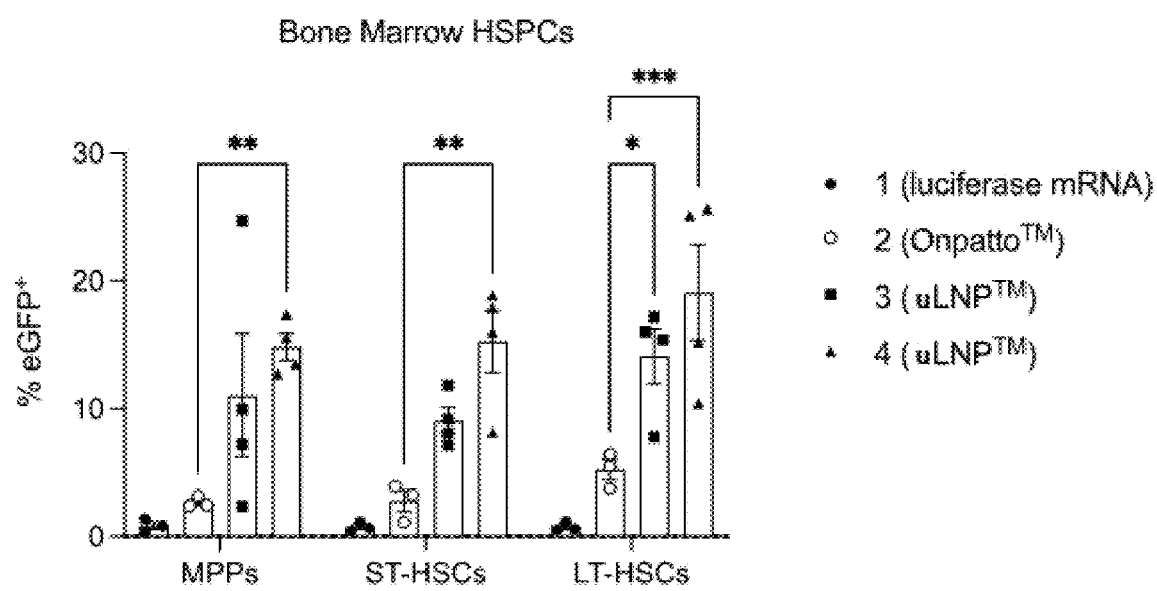

FIG. 31C shows the percentage of enhanced green fluorescent protein (eGFP) positive cells (% eGFP) in bone marrow multipotent progenitor (MPP; Lineage⁻c-Kit⁺Sca1⁺ CD34⁺), short term HSC (ST-HSC; Lineage⁻c-Kit⁺Sca-1⁺ CD34⁺) and long-term HSC (LT-HSC; Lineage cKit⁺Sca1⁺ CD34⁻CD135⁻) sub-populations as indicated after 24 hours post-injection of LNP 1 (luciferase mRNA), LNP 2 eGFP-mRNA (Onpattro™) and LNPs 3 and 4 (uLNP) to C57Bl/6 mice. The LNP formulations 1 to 4 are described in FIG. 31A above.

DETAILED DESCRIPTION

Neutral Lipid

The LNP includes "a neutral lipid", which includes one or more neutral lipids other than sterols. The neutral lipid includes any lipid that bears no charge at physiological pH, including zwitterionic lipids having at least substantially no net charge at physiological pH. In one embodiment, the neutral lipid is amphipathic and has at least two tails and a polar region, such as a head group. The term includes lipids with choline head groups (e.g., phosphatidylcholine), meaning an amphipathic lipid that has a choline head group and that bears no or substantially no net charge at physiological pH. The neutral lipid also includes phospholipids conjugated to sterols. In some embodiments, the lipid with a choline head group is a phosphatidylcholine lipid, such as a lipid that is selected from distearoylphosphatidylcholine (DSPC), dioleoylphosphatidylcholine (DOPC), dimyristoylphosphatidylcholine (DMPC), 1-palmitoyl-2-oleoyl-phosphatidylcholine (POPC) and dipalmitoyl-phosphatidylcholine (DPPC) and sphingomyelin with a phosphocholine head group.

As used herein "head group", means a moiety that imparts polarity to the lipid and comprises one or more electronegative atoms, such as nitrogen, oxygen and/or phosphorus. Generally, the electronegative atom or atoms are part of one or more functional groups. In some embodiments, the head group is zwitterionic. In some embodiments, the head group comprises a phosphate group and a nitrogen atom. In some embodiments, the head group is zwitterionic and has no net charge at physiological pH.

The phosphatidylcholine lipid content may include mixtures of two or more types of different phosphatidylcholine lipids. In one embodiment, the phosphatidylcholine lipid content is a mixture of two or more of the phosphatidylcholine lipids selected from DSPC, DPPC, DMPC, DOPC and POPC. In some embodiments, the phosphatidylcholine lipid content is primarily DSPC or DMPC or primarily DSPC.

In such embodiments, the neutral lipid mixture may have a DSPC content of at least 20, 22, 30, 35, 40 or 45 mol % based on the total lipid content of the lipid nanoparticle with the balance of the phosphatidylcholine lipid content being another phosphatidylcholine lipid(s). In another embodiment, the phosphatidylcholine content is made up of at least 40 or 50 mol % DSPC relative to the total phosphatidylcholine content of the lipid nanoparticle.

In alternative embodiments, the neutral lipid mixture may have a DMPC content of at least 20, 30, 35, 40 or 45 mol % based on the total lipid content of the lipid nanoparticle. In another embodiment, the phosphatidylcholine content is made up of at least 40 mol % DMPC relative to the total phosphatidylcholine content of the lipid nanoparticle. In another embodiment the phospholipid content of the lipid nanoparticle has less than 10, or less than 5 mol % of non-phosphatidylcholine lipids, such as DOPE.

In some embodiments, the transition temperature of the lipid (e.g., phospholipid) having a choline head group is at least 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. In some embodiments, the transition temperature of the lipid (e.g., phospholipid) having a choline head group is at least 42° C., 43° C., 44° C., 45° C., 46° C., 47° C., 48° C., 49° C. or 50° C. In some embodiments, the transition temperature of the lipid (e.g., phospholipid) having a choline head group is between 20° C. and 60° C. or between 42° C. and 60° C. The phase transition temperature of the lipid is measured using differential scanning calorimetry (DSC) using techniques known to those of skill in the art and is the main phase transition temperature.

Without intending to be limited by any particular theory, it is believed that fusion and agglomeration of lipid nanoparticles with no hydrophilic polymer lipid conjugate (or low levels thereof) during particle formation using the mixing method described herein could be avoided by selecting a phospholipid having a choline head group that is in the gel phase rather than in the disordered liquid crystalline phase at room temperature and above. This inclusion of such phosphatidylcholine lipids in the lipid nanoparticle may also improve blood stability after injection.

In some embodiments, the phosphatidylcholine lipid is a phosphatidylcholine-sterol conjugate, such as an SPC-cholesterol, OPC-cholesterol or PPC-cholesterol conjugate. Additional phospholipid-sterol conjugates are described in US2011/0177156, which is incorporated herein by reference. An example of a suitable phospholipid that is an SPC-cholesterol conjugate is set forth below:

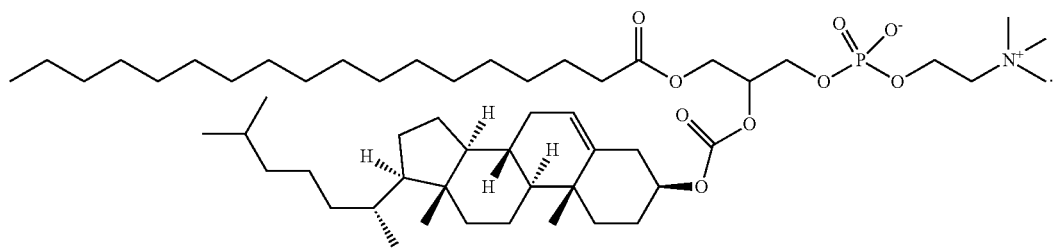

In some embodiments, the phosphatidylcholine lipid is a sphingolipid. As used herein the term "sphingolipid", means a lipid comprising a sphingosine backbone and that is suitable for formulation in the LNPs herein. The sphingolipid includes a ceramide, a sphingomyelin, a cerebroside, a ganglioside, or derivatives, such as but not limited to reduced analogues thereof, that lack a double bond in the sphingosine unit. The sphingolipid has a phosphocholine head group and includes sphingomyelin.

The neutral lipid content in some embodiments (excluding sterol) is greater than 20 mol %, greater than 22 mol %, greater than 22.5 mol %, greater than 25 mol %, greater than 27.5 mol % greater than 30 mol %, greater than 32 mol %, greater than 34 mol %, greater than 36 mol %, greater than 38 mol %, greater than 40 mol %, greater than 42 mol %, greater than 44 mol %, or greater than 46 mol % In some embodiments, the upper limit of phosphatidylcholine lipid content is 70 mol %, 65 mol %, 60 mol %, 55 mol %, 50 mol % or 45 mol %. The disclosure also encompasses sub-ranges of any combination of the foregoing numerical upper and lower limits.

The content of neutral lipid having a choline head group in some embodiments (excluding sterol) is greater than 20 mol %, greater than 22 mol %, greater than 22.5 mol %, greater than 25 mol %, greater than 27.5 mol % greater than 30 mol %, greater than 32 mol %, greater than 34 mol %, greater than 36 mol %, greater than 38 mol %, greater than 40 mol %, greater than 42 mol %, greater than 44 mol %, or greater than 46 mol % In some embodiments, the upper limit of phosphatidylcholine lipid content is 70 mol %, 65 mol %, 60 mol %, 55 mol %, 50 mol % or 45 mol %. The disclosure also encompasses sub-ranges of any combination of the foregoing numerical upper and lower limits.

The content of neutral lipid having at least two tails and a polar region (e.g., head group) in some embodiments (excluding sterol) is greater than 20 mol %, greater than 22 mol %, greater than 22.5 mol %, greater than 25 mol %, greater than 27.5 mol % greater than 30 mol %, greater than 32 mol %, greater than 34 mol %, greater than 36 mol %, greater than 38 mol %, greater than 40 mol %, greater than 42 mol %, greater than 44 mol %, or greater than 46 mol % In some embodiments, the upper limit of phosphatidylcholine lipid content is 70 mol %, 65 mol %, 60 mol %, 55 mol %, 50 mol % or 45 mol %. The disclosure also encompasses sub-ranges of any combination of the foregoing numerical upper and lower limits.

The phosphatidylcholine lipid content in some embodiments is greater than 20 mol %, greater than 22 mol %, greater than 22.5 mol %, greater than 25 mol %, greater than 27.5 mol % greater than 30 mol %, greater than 32 mol %, greater than 34 mol %, greater than 36 mol %, greater than 38 mol %, greater than 40 mol %, greater than 42 mol %, greater than 44 mol %, or greater than 46 mol % In some embodiments, the upper limit of phosphatidylcholine lipid content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the neutral lipid content is from 22 mol % to 60 mol %, 25 mol % to 60 mol %, 30 mol % to 60 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

For example, in certain embodiments, the content of neutral lipid having a choline head group is from 22 mol % to 60 mol %, 25 mol % to 60 mol %, 30 mol % to 60 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

For example, in certain embodiments, the content of neutral lipid having at least two tails and a polar region (e.g., head group) in some embodiments (excluding sterol) is from 22 mol % to 60 mol %, 25 mol % to 60 mol %, 30 mol % to 60 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

For example, in certain embodiments, the phosphatidylcholine lipid content is from 22 mol % to 60 mol %, 25 mol % to 60 mol %, 30 mol % to 60 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

In certain embodiments, the DSPC lipid content is from 25 mol % to 65 mol %, 30 mol % to 65 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

In certain embodiments, the DMPC lipid content is from 25 mol % to 65 mol %, 30 mol % to 65 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

In certain embodiments, the sphingolipid or sphingomyelin lipid content is from 25 mol % to 65 mol %, 30 mol % to 65 mol %, 35 mol % to 60 mol %, 40 mol % to 60 mol %, 42 mol % to 58 mol %, 43 mol % to 57 mol %, 44 mol % to 56 mol % or 45 mol % to 55 mol % of total lipid present in the lipid nanoparticle.

The phosphatidylcholine lipid content is determined based on the total amount of lipid in the lipid nanoparticle, including the sterol and any amounts of additional lipid components that are optionally present.

In alternative embodiments, the DMPC content is less than 22 mol %, 20 mol %, 18 mol %, 16 mol %, 14 mol %, 12 mol %, 10 mol %, 8 mol %, 6 mol %, 4 mol % or 2 mol % based on the total lipid content of the lipid nanoparticle. In alternative embodiments, the DPPC content is less than 22 mol %, 20 mol %, 18 mol %, 16 mol %, 14 mol %, 12 mol %, 10 mol %, 8 mol %, 6 mol %, 4 mol % or 2 mol % based on the total lipid content of the lipid nanoparticle. In alternative embodiments, the DOPE content is less than 22 mol %, 20 mol %, 18 mol %, 16 mol %, 14 mol %, 12 mol %, 10 mol %, 8 mol %, 6 mol %, 4 mol % or 2 mol % mol % based on the total lipid content of the lipid nanoparticle.

Sterol

As set forth herein, the LNPs of the disclosure comprise a sterol.

The term "sterol" refers to steroids that are naturally-occurring or synthetic. The term includes sterol derivatives such as phytosterols, zoosterols and derivatives thereof.

The term "sterol derivatives" refers to modified sterols or precursors thereof, including triterpenes.

The term "cholesterol" refers to a naturally-occurring or synthetic compound having a gonane skeleton and that has a hydroxyl moiety attached to one of its rings, typically the A-ring.

The LNP may alternatively or additionally comprise a "cholesterol derivative". The cholesterol derivative may be naturally-occurring or man-made and includes but is not limited to a cholesterol molecule having a gonane structure and one or more additional functional groups.

In another embodiment, the LNP may comprise a triterpene. Non-limiting examples include squalene, achilleol A, polypodatetraene, malabaricane, lanostane, cucuribitacin, hopane, oleanane, and urosolic acid.

The LNP may further comprise a tocopherol as an additional component. In certain embodiments, the cholesterol derivative is a phytosterol. The phytosterol may be β-sitosterol, 3-sitosterol, campesterol, stigmasterol, fucosterol, or stigmastanol or a salt or ester thereof.

In certain embodiments, the cholesterol derivative is selected from β-sitosterol, β-sitosterol 3-sitosterol, campesterol, stigmasterol, fucosterol, or stigmastanol, dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3β[N—(N'N'-dimethylaminoethyl) carbamoyl cholesterol (DC-Chol), 24 (S)-hydroxycholesterol, 25-hydroxycholesterol, 25 (R)-27-hydroxycholesterol, 22-oxacholesterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, 3,6,9-trioxaoctan-1-ol-cholesteryl-3e-ol, dehydroergosterol, 9,11-dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol, daucosterol, or a salt or ester thereof.

The sterol or cholesterol derivative may be conjugated to another moiety, such as an amino acid or an alkyl group.

In one embodiment, the sterol (which encompasses a derivative thereof) is present at from 12 to 40 mol %, 12 to 35 mol %, 14 to 32 mol %, 15 to 28 mol % or 15 to 26 mol % based on the total lipid present in the lipid nanoparticle. In a further embodiment, the sterol is present at 21 to 40 mol %.

In another embodiment, the sterol (which encompasses a derivative thereof) is present at greater than 12 mol %, 13 mol %, 14 mol %, 15 mol %, 16 mol %, 17 mol %, 18 mol %, 19 mol %, 20 mol %, 21 mol % or 22 mol %. The upper limit of the sterol or sterol derivative content may be 46 mol %, 44 mol %, 42 mol %, 40 mol %, 38 mol %, 36 mol %, 34 mol %, 32 mol % or 30 mol %. The sterol content may include any combination of the foregoing lower and upper limits and may include mixtures of different kinds of sterols.

In one embodiment, the cholesterol (encompassing derivatives thereof) is present at from 12 to 40 mol %, 12 to 35 mol %, 14 to 32 mol %, 15 to 28 mol % or 15 to 26 mol % based on the total lipid present in the lipid nanoparticle. In a further embodiment, the cholesterol is present at 21 to 40 mol %.

In another embodiment, the cholesterol is present at greater than 12 mol %, 13 mol %, 14 mol %, 15 mol %, 16 mol %, 17 mol %, 18 mol %, 19 mol %, 20 mol %, 21 mol % or 22 mol %. The upper limit of the cholesterol or cholesterol derivative content may be 46 mol %, 44 mol %, 42 mol %, 40 mol %, 38 mol %, 36 mol %, 34 mol %, 32 mol % or 30 mol %. The cholesterol content may include any combination of the foregoing lower and upper limits.

In some embodiments, the combined neutral lipid and sterol content (e.g., phosphatidylcholine, sterol and any additional neutral lipids, if present) is at least 50, 55, 60, 65 or 70 mol % relative to the total lipid content of the lipid nanoparticle. As used herein, the neutral lipid content encompasses non-sterol helper lipids.

In one embodiment, the neutral lipid:sterol molar ratio is between 0.6:1 and 3.5:1 (mol:mol). In another embodiment, the neutral lipid:sterol molar ratio is between 0.7:1 and 3.2:1 (mol:mol). In a further embodiment, the neutral lipid:sterol molar ratio is between 0.8:1 and 2:1 (mol:mol). In a further embodiment, the neutral lipid:sterol molar ratio is between 0.7:1 and 1.5:1 (mol:mol).

In one embodiment, the phospholipid:sterol molar ratio is between 0.6:1 and 3.5:1 (mol:mol). In another embodiment, the phospholipid:sterol molar ratio is between 0.7:1 and 3.2:1 (mol:mol). In a further embodiment, the phospholipid:sterol molar ratio is between 0.8:1 and 2:1 (mol:mol). In a further embodiment, the phospholipid:sterol molar ratio is between 0.7:1 and 1.5:1 (mol:mol).

In one embodiment, the phosphatidylcholine:sterol molar ratio is between 0.6:1 and 3.5:1 (mol:mol). In another embodiment, the phosphatidylcholine:sterol molar ratio is between 0.7:1 and 3.2:1 (mol:mol). In a further embodiment, the phosphatidylcholine:sterol molar ratio is between 0.8:1 and 2:1 (mol:mol). In a further embodiment, the phosphatidylcholine:sterol molar ratio is between 0.7:1 and 1.5:1 (mol:mol).

In one embodiment, the sphingolipid:sterol molar ratio is between 0.6:1 and 3.5:1 (mol:mol). In another embodiment, the sphingolipid:sterol molar ratio is between 0.7:1 and 3.2:1 (mol:mol). In a further embodiment, the sphingolipid:sterol molar ratio is between 0.8:1 and 2:1 (mol:mol). In a further embodiment, the sphingolipid:sterol molar ratio is between 0.7:1 and 1.5:1 (mol:mol).

In some embodiments, the phosphatidylcholine:sterol molar ratio is greater than 1:1, such as between 1.2:1 and 4:1, between 1.5:1 and 3.5:1, between 1.8:1 and 3.2:1 or between 2:1 and 3:1 (mol:mol).

In some embodiments, the distearoylphosphatidylcholine:sterol molar ratio is greater than 1:1, such as between 1.2:1 and 4:1, between 1.5:1 and 3.5:1, between 1.8:1 and 3.2:1 or between 2:1 and 3:1 (mol:mol).

In some embodiments, the distearoylphosphatidylcholine:cholesterol molar ratio is greater than 1:1, such as between 1.2:1 and 4:1, between 1.5:1 and 3.5:1, between 1.8:1 and 3.2:1 or between 2:1 and 3:1 (mol:mol).

Ionizable Cationic Lipid

The LNP of the disclosure has an ionizable cationic lipid, which includes one or a combination of two or more of such lipids.

As used herein, the term "ionizable cationic lipid" refers to a lipid that, at a given pH, such as physiological pH, is in an electrostatically neutral form and that accepts protons, thereby becoming electrostatically positively charged at a pH below its pKa. The electrostatically neutral form has a calculated logarithm of the partition coefficient between water and 1-octanol (i.e., a cLogP) greater than 8. In some embodiments, the cationic lipid has an apparent pKa (determined using the method described herein) that is between 5.0 and 7.5 or between 6.0 and 7.5 when formulated in the LNP.

Accordingly, the ionizable cationic lipid is charged at low pH and bears substantially no net charge at physiological pH. This allows for electrostatic interactions between the lipid and the negatively charged nucleic acid cargo during initial formulation. Since the ionizable lipid is near neutral at physiological pH, toxicity and renal clearance is reduced. Without being limited by theory, after cellular uptake by endocytosis, the acidic environment of the endosome leads to an increase in the net positive charge of the ionizable amino lipids, which promotes fusion with the anionic lipids of the endosomal membrane and subsequent membrane destabilization and release of the nucleic acid-based therapeutics into the cytoplasm to exert their effects. Since the LNPs are non-sterically stabilized, it is believed that fusion with the endosomal membrane is enhanced relative to the same particle having 1.5 mol % PEG-lipid (e.g., PEG$_{2000}$-DMG).

In some embodiments, the LNP has an apparent pKa of between 5.0 and 7.5, between 6.5 and 7.5 or between 6.8 and 7.3. The apparent pKa is measured using a 6-(p-Toluidino)-2-naphthalenesulfonic acid (TNS) assay adapted from previous studies from other groups (Shobaki et al., 2018, International Journal of Nanomedicine, 13:8395-8410; and Jayaraman et al., 2012, Angew. Chem Int. Ed., 51:8529-8533, which are incorporated herein by reference for the purposes of determining apparent pKa). According to the method, a series of buffers are prepared spanning a pH range of 2-11 in 0.5 pH unit increments consisting of 130 mM NaCl, 10 mM ammonium acetate, 10 mM 2-(N-morpholino) ethanesulfonic acid (MES), and 10 mM HEPES. 0.15-0.2 mM of the LNP. A solution of 0.06 mM of TNS is subsequently mixed with 175 µL of the LNP at each buffered pH in triplicate in a black, polystyrene 96-well plate, to yield a final concentration of 6.25 and 6 µM of lipid and TNS in each well, respectively. Fluorescence is subsequently measured using an SpectraMax™ M5 microplate reader at $\lambda_{ex}$=321 nm, $\lambda_{em}$=445 nm. The fluorescence is then plotted against pH using a sigmoidal curve fit through Prism™, in which the pKa is determined to be the pH value with 50% of maximal fluorescent intensity.

In some embodiments, it is desirable to include less than 40 mol % ionizable lipid in the LNP. In certain embodiments, the ionizable lipid content is from 5 mol % to 50 mol % or 8 mol % to 47 mol % or 10 mol % to 50 mol % or 15 mol % to 45 mol % or 15 mol % to 35 mol % of total lipid present in the lipid nanoparticle.

In certain embodiments, the ionizable lipid content may be less than 48 mol %, less than 45 mol %, less than 40 mol %, less than 35 mol %, less than 30 mol %, less than 25 mol %, less than 20 mol %, less than 15 mol %, less than 10 mol % or less than 5 mol %. In certain embodiments, the lower limit of the ionizable lipid content may be greater than 5 mol %, greater than 8 mol %, greater than 10 mol %, greater than 12 mol %, greater than 14 mol %, greater than 15 mol %, greater than 16 mol %, greater than 18 mol % or greater than 20 mol %. Any one of the upper limits may be combined with any one of the lower limits to arrive at a suitable ionizable lipid content in the LNP.

In some embodiments, the ionizable cationic lipid has an amino group. In another embodiment, the ionizable cationic lipid has a single amino group that is ionizable. In some embodiments, the ionizable cationic lipid comprises a protonatable tertiary amine (e.g., pH titratable) head group. Such lipids include, but are not limited to sulfur lipids, such as MF019 described herein and DODMA. Other lipids that may be used in the practice of the disclosure include MC3- and KC2-type lipids, which are well-known to those of skill in the art. In further embodiments, the ionizable lipid is selected from one or more lipids set forth in WO 2022/246555; WO 2022/246568; WO 2022/246571; WO 2023/147657; WO2022/155728; WO 2023/215989; WO 2024/065041; WO 2024/065042; WO 2024/130421; WO 2024/065043; and U.S. patent application Ser. No. 18/442,431 filed on Feb. 15, 2024, each incorporated herein by reference.

In one embodiment, the ionizable cationic lipid comprises an ionizable amino head group and at least two lipophilic groups that converge to a central carbon or nitrogen atom and wherein the central carbon or nitrogen atom is bonded to a head group moiety. At least one or more, typically both, of the lipophilic chains may contain a biodegradable group, such as an ester, and/or one or more sulfur atoms. In some embodiments, at least one lipophilic group comprises alkyl branching disposed between the head group and the biodegradable group and/or one or more cyclic alkyl groups distal to the biodegradable group. Examples of ionizable cationic lipids comprising an ionizable amino head group and two lipophilic chains, at least one chain comprising one or more sulfur atoms and/or ester groups are described in co-owned and co-pending WO 2023/215989; WO 2024/065041; WO 2024/065042; WO 2024/130421; and WO 2024/065043, which are incorporated herein by reference. Functional groups comprising one or more heteroatoms may be biodegradable in vivo.

In one embodiment, the lipid nanoparticle comprises a "sulfur-containing amino lipid", which is an ionizable lipid having at least one ionizable nitrogen (tertiary nitrogen) and one or more sulfur atoms in at least one of its lipophilic chains. In one embodiment, the sulfur-containing amino lipid further comprises a biodegradable group such as an ester moiety in one or more of its lipophilic chains. Non-limiting examples of sulfur-containing lipids are provided in Table 3 and in the foregoing co-owned PCT applications. The incorporation of the biodegradable group(s) into the lipid increases metabolism post-administration and improves clearance of the lipid from the body following delivery of the active agent to a target area. Generally, such lipids have decreased toxicity when compared to similar lipids without the biodegradable groups.

Sulfur-containing ionizable lipids and/or ionizable lipids with one or more biodegradable groups (e.g., esters, groups comprising an ester or a disulfide) in one or more of their lipophilic chains have been shown to be particularly efficacious when formulated in the unshielded LNPs as described in the Example section herein.

Non-limiting examples of atoms or substituents that may replace a carbon atom (interrupt the alkyl) in the lipophilic chains of the ionizable cationic lipid include cycloalkyl groups (mono or polycyclic); —O—; —(C=O)O—; —O(C=O)—; —C(=O); —O(C=O)O—; —S(O)$_x$—; —S—; —S—S—; —C(=O)S—; —SC(=O)—; —NR'—; —NR'C(=O)—; —C(=O) NR'—; —NR'C(=O) NR'—; —OC(=O)NR'—; —NR'C(=O)OR'—; —NR'S(O)$_x$NR'—; —NR'S(O)$_x$R'—; and —S(O)$_x$NR'—, wherein R' at each occurrence is independently selected from H, C$_1$-C$_{15}$ alkyl or cycloalkyl, and x is 0, 1 or 2.

The term "biodegradable group", with reference to a group in a lipophilic chain of an ionizable lipid, includes a functional group with one or more electronegative atoms (e.g., O, N, S or P) that is metabolized in vivo by an enzyme, thereby increasing its metabolism relative to an otherwise identical ionizable lipid that does not contain such group. Non-limiting examples include —O—; —(C=O)O—; —O(C=O)—; —C(=O); —O(C=O)O—; —S(O)$_x$—; —S—; —S—S—; —C(=O)S—; —SC(=O)—; —NR'—; —NR'C(=O)—; —C(=O)NR'—; —NR'C(=O) NR'—; —OC(=O)NR'; —NR'C(=O)OR'—; —NR'S(O)$_x$NR'; —NR'S(O)$_x$R'—; and —S(O)$_x$NR'—, wherein R' at each occurrence is independently selected from H, C$_1$-C$_{15}$ alkyl or cycloalkyl, and x is 0, 1 or 2.

Non-limiting examples of atoms or substituents that may replace a hydrogen atom in the ionizable cationic lipid include halogen; deuterium, an alkyl group; a cycloalkyl group (mono or polycyclic); an oxo group (=O); a hydroxyl group (—OH); —(C=O)OR'; —O(C=O)R'; —C(=O)R';

O(C=O)OR'—; —OR'; —S(O)$_x$R'; —SR', —S—SR'; —C(=O)SR'; —SC(=O)R'; —NR'R'; —NR'C(=O) R'; —C(=O) NR'R'; —NR'C(=O)NR'R'; —OC(=O)NR'R'; NR'C(=O)OR'; —NR'S(O)$_x$NR'R'; —NR'S(O)$_x$R'; and —S(O)$_x$NR'R', wherein R' at each occurrence is independently selected from H, $C_1$-$C_{15}$ alkyl or cycloalkyl, and x is 0, 1 or 2.

In one embodiment, the ionizable amino lipid lacks a five-membered ring, including a furan ring, such as an oxolane in the head group moiety. In an alternative embodiment, the ionizable lipid lacks an ionizable amino group that is a methyl 4-(dimethylamino) butanoate.

In one embodiment, the ionizable amino lipid is a "non-furan ring-containing ionizable lipid" which is an ionizable lipid that lacks a furan ring, such as an oxolane in the head group moiety. In an alternative embodiment, the ionizable lipid is a "non-MC3 type lipid", which is an ionizable lipid that lacks an ionizable amino group that is a methyl 4-(dimethylamino) butanoate.

Generally, it is not conventional in the art to include an ionizable cationic lipid at an amount that is less than the 50 mol % used in Onpattro™ and the Covid vaccines. The inventors have found that including lower amounts of ionizable cationic lipid may not impact potency of the LNP. In some embodiments, it is desirable to include less than 40 mol % ionizable cationic lipid in the LNP. That is, the ionizable cationic lipid content may be less than 40 mol %, less than 35 mol %, less than 30 mol %, less than 25 mol %, less than 20 mol %, less than 15 mol %, less than 10 mol % or less than 5 mol %.

In certain embodiments, the ionizable cationic lipid content is from 15 mol % to 40 mol % or 8 mol % to 47 mol % or 10 mol % to 50 mol % or 15 mol % to 45 mol % or 15 mol % to 35 mol % of total lipid present in the lipid nanoparticle.

In certain embodiments, the ionizable amino cationic lipid content is from 15 mol % to 40 mol % or 8 mol % to 47 mol % or 10 mol % to 50 mol % or 15 mol % to 45 mol % or 15 mol % to 35 mol % of total lipid present in the lipid nanoparticle.

In some embodiments, the ionizable cationic lipid is not a lipidoid structure, including but not limited to C12-200 (see Khare et al., 2022, AAPS Journal, 24:8, incorporated by reference) and related structures known to those of skill in the art. In some embodiments, the ionizable cationic lipid is not a dendrimer (termed herein "non-dendrimer").

Substantially No Surface Stabilizer (e.g., Hydrophilic Polymer-Lipid Conjugate)

The lipid nanoparticle has "substantially no hydrophilic polymer-lipid conjugate" or is "non-sterically stabilized", "unshielded" or "uncoated", meaning the lipid nanoparticle has less than 0.8 mol % total hydrophilic-polymer lipid conjugate or less than 0.8 mol % other surface stabilizer content as measured based on the total lipid content of the nanoparticle.

As used herein, the term "surface stabilizer" is a macromolecule, including a protein, polysaccharide or polymer, including a block copolymer, that is used to stabilize a lipid nanoparticle, and in which at least a portion (e.g., hydrophilic portion) is present on the surface of the lipid nanoparticle. Such molecules are employed by those of skill in the art to prevent aggregation, improve shelf life and/or improve the stability of the particle after administration, such as the circulation lifetime of the lipid nanoparticle. The term includes surface stabilizers that are known to control the size of lipid nanoparticles, such as amphiphilic polymers (e.g., block co-polymer). As would be appreciated by those of skill in the art, a hydrophobic portion of the surface stabilizer may partition in a lipophilic portion of the lipid nanoparticle.

In some embodiments, the surface stabilizer is present at less than 0.75, 0.70, 0.65, 0.60, 0.55, 0.50, 0.45, 0.40, 0.35, 0.30, 0.25, 0.20, 0.15, or 0.10 mol % as measured based on the total lipid content of the lipid nanoparticle. In further embodiments, the surface stabilizer mol % content is between 0 and 0.75 mol %, 0 and 0.70 mol %, 0 and 0.65 mol %, 0 and 0.60 mol %, 0 and 0.55 mol %, 0 and 0.50 mol %, 0 and 0.45 mol %, 0 and 0.40 mol %, 0 and 0.35 mol %, 0 and 0.30 mol %, 0 and 0.25 mol %, 0 and 0.20 mol %, 0 and 0.15 mol % or 0 and 0.10 mol %.

In some embodiments, the hydrophilic-polymer conjugate (e.g., a hydrophilic-polymer lipid conjugate) content is less than 0.75, 0.70, 0.65, 0.60, 0.55, 0.50, 0.45, 0.40, 0.35, 0.30, 0.25, 0.20, 0.15 or 0.10 mol % as measured based on the total lipid content of the nanoparticle. In further embodiments, the hydrophilic-polymer conjugate (e.g., a hydrophilic-polymer lipid conjugate) mol % content is between 0 and 0.75 mol %, 0 and 0.70 mol %, 0 and 0.65 mol %, 0 and 0.60 mol %, 0 and 0.55 mol %, 0 and 0.50 mol %, 0 and 0.45 mol %, 0 and 0.40 mol %, 0 and 0.35 mol %, 0 and 0.30 mol %, 0 and 0.25 mol %, 0 and 0.20 mol %, 0 and 0.15 mol %, 0 and 0.10 mol % or 0 and 0.05 mol %.

The hydrophilic-polymer lipid conjugate (e.g., a lipid conjugate) includes a lipophilic portion that resides in the lipid nanoparticle lipid layer (e.g., bilayer or monolayer) and a polymer chain that is hydrophilic and extends into the surrounding solution. Examples of hydrophilic polymers include polyethyleneglycol (PEG), polyvinylpyrrolidone, polyvinylmethylether, polyhydroxypropyl methacrylate, polyhydroxypropylmethacrylamide, polyhydroxyethyl acrylate, polymethacrylamide, polydimethylacrylamide, polymethyloxazoline, polyethyloxazoline, polyhydroxyethyloxazoline, polyhydroxypropyloxazoline, polysarcosine and polyaspartamide. In one embodiment, the hydrophilic-polymer lipid conjugate is a PEG-lipid conjugate. The hydrophilic polymer may be composed of sugar monomer units. For example, the hydrophilic polymer lipid conjugate may be a naturally-occurring or synthesized oligosaccharide-containing molecule, such as, for example, monosialoganglioside ($G_{M1}$). The lipid nanoparticle may comprise a hydrophilic polymer-lipid conjugate conjugated to a targeting ligand at its distal end.

In some embodiments, the amphipathic polymer content is less than 0.75, 0.70, 0.65, 0.60, 0.55, 0.50, 0.45, 0.40, 0.35, 0.30, 0.25, 0.20, 0.15, 0.10 mol % as measured based on the total lipid content of the nanoparticle. In further embodiments, the amphipathic polymer mol % content is between 0 and 0.75 mol %, 0 and 0.70 mol %, 0 and 0.65 mol %, 0 and 0.60 mol %, 0 and 0.55 mol %, 0 and 0.50 mol %, 0 and 0.45 mol %, 0 and 0.40 mol %, 0 and 0.35 mol %, 0 and 0.30 mol %, 0 and 0.25 mol %, 0 and 0.20 mol %, 0 and 0.15 mol %, 0 and 0.10 mol % or 0 and 0.05 mol %. Examples of amphipathic polymers are provided in US 2021/0046192, which is incorporated herein by reference.

In some embodiments, the poloxamer content is less than 0.50, 0.45, 0.40, 0.35, 0.30, 0.25, 0.20, 0.15, 0.10 mol % as measured based on the total lipid content of the nanoparticle. In further embodiments, the poloxamer mol % content is between 0 and 0.50 mol %, 0 and 0.45 mol %, 0 and 0.40 mol %, 0 and 0.35 mol %, 0 and 0.30 mol %, 0 and 0.25 mol %, 0 and 0.20 mol %, 0 and 0.15 mol %, 0 and 0.10 mol % or 0 and 0.05 mol %.

In further embodiments, the LNP lacks a surface stabilizer that is a protein, referred to as a protein stabilizer. This includes an apolipoprotein stabilizer, derivative or mimetic thereof (see e.g., WO 2023/233042, which is incorporated herein by reference). Such apolipoprotein may be selected from one or a combination of apo A1, apo A1-Milano, apo A2, apo A4, apo A5, apo B48, apo B100, apo C-1, apo C-1 I, apo C-Ill, apo C—IV, apo D, apo E, apo F, apo H, apo L and apo M. In some embodiments, the protein stabilizer content is less than 0.75, 0.70, 0.65, 0.60, 0.55, 0.50, 0.45, 0.40, 0.35, 0.30, 0.25, 0.20, 0.15 or 0.10 mol % as measured based on the total lipid content of the nanoparticle. In some embodiments, the protein stabilizer content is less than 0.45, 0.40, 0.35, 0.30, 0.25, 0.20, 0.15 or 0.10 mol % as measured based on the total lipid content of the nanoparticle. In further embodiments, the protein stabilizer content mol % content is between 0 and 0.75 mol %, 0 and 0.70 mol %, 0 and 0.65 mol %, 0 and 0.60 mol %, 0 and 0.55 mol %, 0 and 0.50 mol %, 0 and 0.45 mol %, 0 and 0.40 mol %, 0 and 0.35 mol %, 0 and 0.30 mol %, 0 and 0.25 mol %, 0 and 0.20 mol %, 0 and 0.15 mol % or 0 and 0.10 mol %. Since lipid nanoparticles can adsorb proteins after administration, the protein content is measured in vitro prior to administration.

Alternatively, in some embodiments a lipid nanoparticle preparation lacks or has low levels thereof of one or more stabilizing agents, which includes a surface stabilizer as described above and a cryoprotectant that functions as a stabilizer. In some embodiments, the lipid nanoparticle preparation has less than 2 w/v, 1.75 w/v, 1.50 w/v, 1.25 w/v, 1.00 w/v, 0.75 w/v, 0.50 w/v, 0.25, 0.10 or 0.05 w/v of one or more cryoprotectants in the preparation. In some embodiments, a lipid nanoparticle preparation having a plurality of LNPs has low levels or lacks glycerol and/or propylene glycol as a cryoprotectant, such as at concentration levels less than 2 w/v, 1.75 w/v, 1.50 w/v, 1.25 w/v, 1.00 w/v, 0.75 w/v, 0.50 w/v, 0.25, 0.10 or 0.05 w/v in the preparation. In some embodiments, the lipid nanoparticle preparation consists essentially of buffer, meaning that a lipid nanoparticle preparation comprises buffer and has less than 2 w/v, 1.75 w/v, 1.50 w/v, 1.25 w/v, 1.00 w/v, 0.75 w/v, 0.50 w/v, 0.25, 0.10 or 0.05 w/v of one or more cryoprotectants in the preparation. In some embodiments, the lipid nanoparticle preparation comprises no cryoprotectant, such as for example, glycerol and/or propylene glycol.

In another embodiment, the lipid nanoparticle is "PEGless", meaning that the lipid nanoparticle has no detectable amounts of polyethylene-glycol lipid conjugate. In further embodiments, the lipid nanoparticle is "PEGless", meaning that the LNP lacks a surface stabilizer comprising a hydrophilic polymer with a polyethylene oxide repeating unit or includes low levels thereof, such as less than 0.75, 0.70, 0.65, 0.60, 0.55, 0.50, 0.45, 0.40, 0.35, 0.30, 0.25, 0.20, 0.15, 0.10 mol % as measured based on the total lipid content of the lipid nanoparticle. In further embodiments, surface stabilizer comprising a hydrophilic polymer has a mol % content that is between 0 and 0.75 mol %, 0 and 0.70 mol %, 0 and 0.65 mol %, 0 and 0.60 mol %, 0 and 0.55 mol %, 0 and 0.50 mol %, 0 and 0.45 mol %, 0 and 0.40 mol %, 0 and 0.35 mol %, 0 and 0.30 mol %, 0 and 0.25 mol %, 0 and 0.20 mol %, 0 and 0.15 mol % or 0 and 0.10 mol %.

Optional Additional Lipid Components

In some embodiments, the lipid nanoparticle is a non-sterically stabilized or unshielded particle encapsulating a nucleic acid cargo and wherein the lipid components are lipids "consisting essentially of" three primary lipid components, which lipid components are a neutral lipid, e.g., an amphipathic lipid with a choline head group, such as a phosphatidylcholine lipid or a sphingolipid, a sterol, including a derivative thereof and an ionizable cationic lipid and in which the lipid nanoparticle has less than 10, 9, 8, 7, 6, 5, 4, 3, 2 or 1 mol % of additional lipid components beyond the foregoing three primary lipid components and has less than 0.75, 0.50, 0.25, 0.15, 0.10 or 0.05 mol % of a surface stabilizer as measured based on the total lipid content of the lipid nanoparticle.

In one embodiment, the unshielded lipid nanoparticle has an outer lipid layer with lipids consisting essentially of helper lipid, namely a phosphatidylcholine or other lipid having a choline head group at greater than 25, 30, 35 or 40 mol % and sterol, and in which the ionizable cationic lipid and nucleic acid cargo is present in the core of the LNP, and in which the lipid nanoparticle has less than 0.75, 0.50, 0.25, 0.15, 0.10 or 0.05 mol % of a surface stabilizer as measured based on the total lipid content of the lipid nanoparticle, wherein the surface stabilizer is a macromolecule. In some embodiments, the lipid nanoparticle has an electron dense region and aqueous portion as visualized by cryo-TEM microscopy.

In some examples, the additional lipid components (excluding any low amounts of surface stabilizer) are present at 0-20 mol %, 0-15 mol %, 0-10 mol %, 0 to 8 mol % or 0 to 5 mol % and include any one of a number of charged and/or uncharged lipids. In some embodiments, the additional lipid component consists of one or more neutral lipids rather than lipids that are charged at physiological pH. Avoiding such charged lipids may reduce uptake by the RES system and thereby not compromise the circulation lifetime of the particle. Examples of such optional additional lipids include triacylglycerides, zwitterionic lipids, such as phospholipids, antioxidants and vitamins.

Examples of additional phospholipids include phosphatidyl glycerols, such as dioleoylphosphatidylglycerol (DOPG), distearoylphosphatidylethanolamine (DSPE), dioleoylphosphatidylethanolamine (DOPE), distearoylphosphatidylserine (DSPS) and sphingomyelins. Examples of sphingomyelins in this context include a ceramide, a sphingomyelin, a cerebroside, a ganglioside, or reduced analogues thereof, that lack a double bond in the sphingosine unit.

In those embodiments in which an anionic lipid is included in the formulation, the anionic lipid may be a lipid with a head group that has a hydroxyl group (see Example 9). Without limitation, this includes anionic lipids such as DOPG and A-0001, which is described in WO 2024/192528 (incorporated herein by reference) and Example 9 below.

Further additional components include hydrophobic moieties such as lipids conjugated to targeting ligands. The ligand includes monosaccharides, disaccharides, polysaccharides, such as mannose or GalNAc, peptides, polypeptides, proteins, which includes without limitation antibodies or fragments thereof, or small molecule ligands, such as without limitation, an ionizable lipid conjugated with a small molecule ligand moiety, folic acid to target a folic acid receptor, or a small molecule glycoside, such as oubain and strophanthidin. In one embodiment, the ligand may be a single-chain antibody fragment. The targeting ligand may be used to target receptors on cells in vivo. In some embodiments, the targeting ligand may be conjugated to any lipophilic component of a molecule, such as a lipid, for example a phospholipid, sterol or ionizable lipid component of the LNP. If small amounts of hydrophilic polymer lipid conjugate are present (e.g., less than 0.2 mol % or typically less), a targeting ligand may be conjugated to its distal end. In certain embodiments, the phospholipid-targeting ligand conjugate is present at less than 10 mol %, less than 5 mol % or less than 3 mol %. In some embodiments, the targeting ligand is most advantageously absent or present at less than 1 mol %.

In one embodiment, the lipid nanoparticle has low levels (less than 5 mol %) or no permanently charged cationic lipid content. In some examples of the disclosure, the lipid nanoparticles, due to the lack of a net charge at physiological pH, promote extended circulation longevity, thereby facilitating extrahepatic delivery to cells. Examples of permanently charged cationic lipids that are best avoided include dioctadecyldimethylammonium bromide (DDAB), and 1,2-Dioleoyl-3-trimethylammonium propane (DOTAP). It is also possible that such permanently charged cationic lipids could impart toxicity to the lipid nanoparticles.

Nanoparticle Preparation and Particle Morphology

Lipid nanoparticles can be prepared using any of a variety of suitable methods, such as a rapid mixing/ethanol dilution process. Examples of preparation methods are described in Jeffs, L. B., et al., Pharm Res, 2005, 22 (3): 362-72; and Leung, A. K., et al., The Journal of Physical Chemistry. C, Nanomaterials and Interfaces, 2012, 116 (34): 18440-18450, each of which is incorporated herein by reference in its entirety.

For example, the method of preparing the lipid nanoparticles may comprise dissolving lipid components (e.g., ionizable lipid, phosphatidylcholine and a sterol or derivative thereof) at appropriate ratios in an organic solvent (e.g., ethanol). An aqueous buffer comprising nucleic acid is prepared separately at a suitable pH to ensure that the head group (e.g., amino group) of an ionizable lipid is protonated to facilitate electrostatic interaction with the negatively charged cargo, and the positively charged ionizable lipid. Such charge interaction improves nucleic acid encapsulation.

In some embodiments, the aqueous phase comprising the nucleic acid is subsequently combined with the organic solvent-lipid mixture comprising the lipids. Combining of the aqueous phase and the organic-solvent-lipid mixture may be carried out in a mixing device (e.g., in-line mixer), such as a T-junction mixer with pumps (e.g., a T-tube mixer), a herringbone micromixer, a toroidal mixer, a multi-inlet vortex mixer or other suitable mixing devices known to those of skill in the art. In some embodiments, the mixing device refers to a device comprising two or more inlets meeting in a central mixing region and an outlet through which the mixture exits the device. The LNP formation may occur upon mixture of the aqueous phase and organic solvent-lipid mixture and/or subsequent to such mixing. (Kulkarni et al., 2019, Nanoscale, 11 (18): 9023-9031, which is incorporated herein by reference).

The aqueous phase typically comprises a buffer. Non-limiting examples of suitable buffers include one or more of sodium acetate, phosphate buffered saline (PBS), sodium formate and sodium succinate. Examples of suitable solvents to prepare the organic solvent-lipid mixture are organic solvents including ethanol, isopropanol, methanol and acetone. In one embodiment, the organic solvent-lipid mixture comprises ethanol.

The aqueous phase and organic-solvent lipid mixture may be introduced to the mixer as two separate respective streams via pumps. The volumetric flow rate of each stream may be the same or different and the respective flow rates of each stream may be adjusted to achieve optimal mixing and/or LNP formation.

In one embodiment, the lipid nanoparticle is prepared using a modified process in which the amount of organic solvent in the lipid nanoparticle preparation formed in the mixing device is reduced relative to the conventional process. The modified process allows for the formulation of ionizable cationic lipids in PEG-less lipid nanoparticles that may not otherwise be capable of being formulated in such particles (see Example 4).

The inventive process involves producing unshielded lipid nanoparticles (e.g., PEG-less lipid nanoparticles or lipid nanoparticles with substantially no hydrophilic polymer-lipid conjugate) with lower amounts of organic solvent relative to the conventional rapid mixing process. In one exemplary embodiment, this is achieved by adjusting volumetric flow rates of the two streams combined in the mixer. In one embodiment, the volumetric flow rate of the aqueous buffer solution comprising the nucleic acid is greater than the flow rate of the organic solvent lipid containing mixture, thereby resulting in a lipid nanoparticle solution having reduced levels of the organic solvent. A non-limiting example of a suitable flow rate ratio is 3:1 aqueous:organic solutions v/v. A person of ordinary skill in the art can select a suitable flow rate to the mixer or this could be determined empirically to best suit the mixer used. The flow rate of the aqueous phase may be at least 10%, 20%, 30%, 40%, 50%, 60%, 70%, 80%, 90% or 100% greater than the volumetric flow rate of the organic solvent lipid mixture.

Alternatively or additionally, the lipid nanoparticle solution may be diluted with a buffer solution after exiting the mixing device to reduce the organic solvent concentration. In some embodiments, the lipid nanoparticle so produced may be diluted at a dilution ratio above 0.5:1 (v:v) of buffer solution:lipid nanoparticle solution after existing the mixing device. In some embodiments, the dilution ratio of buffer: lipid nanoparticle solution is at least 0.5:1, 0.55:1, 0.60:1, 0.65:1, 0.70:1, 0.75:1, 0.80:1, 0.85:1, 0.90:1, 0.95:1, 1:1, 1.05:1, 1.10:1, 1.15:1, 1.20:1, 1.25:1, 1.30:1, 1.35:1, 1.40:1, 1.45:1, 1.50:1, 1.55:1, 1.60:1, 1.65:1, 1.70:1, 1.75:1, 1.80:1, 1.85:1, 1.90:1, 1.95:1 or 2.0:1. In some advantageous embodiments, the dilution ratio of buffer:lipid nanoparticle solution is at least 0.90:1, 0.95:1, 1:1, 1.05:1, 1.10:1, 1.15:1, 1.20:1, 1.25:1, 1.30:1, 1.35:1, 1.40:1, 1.45:1, 1.50:1, 1.55:1, 1.60:1, 1.65:1, 1.70:1, 1.75:1, 1.80:1, 1.85:1, 1.90:1, 1.95:1 or 2.0:1. In some embodiments, the upper limit of the dilution ratio of buffer:lipid nanoparticle solution is 5:1, 4.5:1, 4.0:1, 3.5:1, 3.0:1 or 2.5:1.

In some examples, the buffer used to dilute the lipid nanoparticle solution after exiting the mixing device may be sodium acetate, phosphate buffered saline (PBS), sodium formate and/or sodium succinate. The buffer may be the same or different from the buffer used in the aqueous buffer solution comprising the nucleic acid.

The LNP prepared as described above generally comprises a "core" region, which may include an electron dense region and optionally an aqueous portion as visualized by cryo-TEM microscopy. Without being limiting, the electron dense region within the core may be partially surrounded by an aqueous portion within the enclosed space, entirely surrounded or enveloped by an aqueous portion within the core or may have a solid core without an aqueous portion as observed by cryo-TEM. The core may comprise nucleic acid and ionizable lipid. In one embodiment, the phosphatidylcholine and sterol or derivative thereof is present primarily in an outer lipid layer and the ionizable cationic lipid and nucleic acid cargo is present in the core of the LNP.

In some embodiments, the LNP is not a lipoplex. Lipoplexes are prepared by mixing preformed cationic liposomes with nucleic acid in an aqueous solution and may exhibit undesirable properties such as localization of the cargo on the particle surface. Lipoplexes lack the above-described core of the LNP particle. Further, LNPs have a defined size, shape and morphology whereas lipoplexes lack such defined physical characteristics. (See Kubota et al., 2017, Int. J. Nanomedicine, 12:5121-5133 and Kulkarni et al., 2018, Nucleic Acid Therapeutics, 28 (3): 146-157, which are each incorporated herein by reference).

Thus, according to some embodiments, the LNPs disclosed herein have a defined mean particle size that ranges between 40 and 150 nm or between 40 and 140 nm or between 45 and 150 nm or between 50 and 150 nm or between 50 and 120 nm or between 50 and 140 nm. In some embodiments, at least 90% of the particles have a size within any one of the foregoing ranges using dynamic light scattering as set forth in the Materials and Methods herein. In some embodiments, the particle size distribution is +/−40, 30 or 20 nm, meaning the lipid nanoparticles in a lipid nanoparticle preparation do not vary significantly in size. In some embodiments, the LNPs herein have a PDI of less than 0.25, less than 0.20, less than 0.18, less than 0.16, less than 0.15 or less than 0.14.

As used herein, the term "encapsulation," with reference to incorporating the nucleic acid cargo within an LNP refers to any association of the nucleic acid with any lipid component or compartment of the lipid nanoparticle. However, this excludes localization of the nucleic acid on the particle surface as in lipoplexes. In some examples of the disclosure, the nucleic acid is present in the core of the LNP. Without being limited by theory, the nucleic acid may be present in micelles within the core of the LNP.

Nucleic Acid Cargo

In one embodiment, the cargo is a nucleic acid. The nucleic acid includes, without limitation, RNA, including small interfering RNA (siRNA), small nuclear RNA (snRNA), small nucleolar RNA (snoRNA), micro RNA (miRNA), guide RNA (gRNA), including single guide RNA (sgRNA), prime editing guide RNA (pegRNA), messenger RNA (mRNA), small activating RNA (saRNA), self-replicating RNA (srRNA), transamplifying RNA (taRNA), circular RNA (circRNA), long noncoding RNA (lncRNA), transfer RNA (tRNA), and peptide nucleic acid (PNA); and DNA such as vector DNA and linear DNA, or hybrids thereof. The nucleic acid length can vary and can include nucleic acid of 1-50,000 nucleotides in length. The nucleic acid can be in any form, including single stranded DNA or RNA, double stranded DNA or RNA, or hybrids thereof. Single stranded nucleic acid includes antisense oligonucleotides. The nucleic acid may be conjugated to another molecule, including a targeting moiety. An example of such a nucleic acid conjugate is an antibody-nucleic acid conjugate, or an oligosaccharide-nucleic acid conjugate, such as a GalNAc-nucleic acid conjugate.

In some embodiments, the nucleic acid does not encode for a reporter protein or peptide such as eGFP. In some embodiments, the LNP is part of a pharmaceutical composition that has a therapeutic, diagnostic or prophylactic effect to a subject.

In one embodiment, the cargo is an mRNA, which includes a polynucleotide that encodes at least one peptide, polypeptide or protein. The mRNA includes, but is not limited to, RNA as described in co-pending WO 2023/184038, which is incorporated herein by reference.

The mRNA as used herein encompasses both modified and unmodified mRNA. In one embodiment, the mRNA comprises one or more coding and non-coding regions. The mRNA can be purified from natural sources, produced using recombinant expression systems and optionally purified, or may be chemically synthesized.

In those embodiments in which an mRNA is a chemically synthesized molecule, the mRNA can comprise nucleoside analogs such as analogs having chemically modified bases or sugars, and/or backbone modifications. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The mRNAs of the disclosure may be synthesized according to any of a variety of known methods. For example, mRNAs in certain embodiments may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor.

In some embodiments, in vitro synthesized mRNA may be purified before encapsulation to remove undesirable impurities including various enzymes and other reagents used during mRNA synthesis.

The present disclosure may be used to encapsulate mRNAs of a variety of lengths. In some embodiments, the present disclosure may be used to encapsulate in vitro synthesized mRNA ranging from about 1-20 kb, about 1-20 kb, about 1-15 kb, about 1-10 kb, about 2-20 kb, about 2-15 kb, about 2-10 kb, about 5-20 kb, about 5-15 kb, about 5-12 kb, about 5-10 kb, about 8-20 kb, or about 8-15 kb in length.

Typically, mRNA synthesis includes the addition of a "cap" on the 5' end, and a "tail" on the 3' end. The presence of the cap is advantageous in that it may provide resistance to nucleases found in eukaryotic cells. The presence of a "tail" serves to protect the mRNA from exonuclease degradation.

In some embodiments, mRNAs include a 5' and/or 3' untranslated region. In some embodiments, a 5' untranslated region includes one or more elements that affect an m'NA's stability or translation, for example, an iron responsive element. In some embodiments, a 5' untranslated region may be between about 1 and 500 nucleotides in length or 50 and 500 nucleotides in length or longer.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 1 and 500 nucleotides in length or 50 and 500 nucleotides in length or longer.

In a further embodiment, the mRNA is circular. Advantageously, such mRNA lacks 5' and 3' ends and thus may be more stable in vivo due to its resistance to degradation by exonucleases. The circular mRNA may be prepared by any known method, including any one of the methods described in Deviatkin et al., 2023, "Cap-Independent Circular mRNA Translation Efficiency", Vaccines, 11 (2), 238, which is incorporated herein by reference. Translation of the circular mRNA is carried out by a cap-independent initiation mechanism.

While mRNA provided from in vitro transcription reactions may be desirable in certain embodiments, other sources of mRNA are contemplated, such as mRNA produced from bacteria, fungi, plants, and/or animals.

The mRNA sequence may comprise a reporter gene sequence, although the inclusion of a reporter gene sequence in pharmaceutical formulations for administration is optional. Such sequences may be incorporated into mRNA for in vitro studies or for in vivo studies in animal models to assess expression and biodistribution.

In another embodiment, the cargo is an siRNA. An siRNA becomes incorporated into endogenous cellular machineries to result in mRNA breakdown, thereby preventing transcription. Since RNA is easily degraded, its incorporation into a delivery vehicle can reduce or prevent such degradation, thereby facilitating delivery to a target site.

The siRNA encompassed by embodiments of the disclosure may be used to specifically inhibit expression of a wide variety of target polynucleotides. The siRNA molecules targeting specific polynucleotides for any therapeutic, prophylactic or diagnostic application may be readily prepared according to procedures known in the art. An siRNA target site may be selected and corresponding siRNAs may be chemically synthesized, created by in vitro transcription, or expressed from a vector or PCR product. A wide variety of different siRNA molecules may be used to target a specific gene or transcript. The siRNA may be double-stranded RNA, or a hybrid molecule comprising both RNA and DNA, e.g., one RNA strand and one DNA strand. The siRNA may be of a variety of lengths, such as 1 to 30 nucleotides in length or 15 to 30 nucleotides in length or 20 to 25 nucleotides in length. In certain embodiments, the siRNA is double-stranded and has 3' overhangs or 5' overhangs. In certain embodiments, the overhangs are UU or dTdT 3'. In particular embodiments, the siRNA comprises a stem loop structure.

In a further embodiment, the cargo molecule is a microRNA or small nuclear RNA. Micro RNAs (miRNAs) are short, noncoding RNA molecules that are transcribed from genomic DNA, but are not translated into protein. These RNA molecules are believed to play a role in regulation of gene expression by binding to regions of target mRNA. Binding of miRNA to target mRNA may downregulate gene expression, such as by inducing translational repression, deadenylation or degradation of target mRNA. Small nuclear RNA (snRNA) are typically longer noncoding RNA molecules that are involved in gene splicing. The snRNA molecules may have therapeutic or diagnostic importance in diseases that are an outcome of splicing defects.

In another embodiment, the cargo is a DNA vector. The encapsulated DNA vectors may be administered to a subject for the purpose of repairing, enhancing or blocking or reducing the expression of a cellular protein or peptide. In another embodiment, the encapsulated DNA vectors may be administered to a subject for diagnosis of disease. The DNA vector may localize in target cells (e.g., rapidly dividing cells) and expression of encoded DNA may be used to provide a measurable signal. Accordingly, the nucleotide polymers can be nucleotide sequences including genomic DNA, cDNA, or RNA.

As will be appreciated by those of skill in the art, the vectors may encode promoter regions, operator regions or structural regions. The DNA vectors may contain double-stranded DNA or may be composed of a DNA-RNA hybrid. Non-limiting examples of double-stranded DNA include structural genes, genes including operator control and termination regions, and self-replicating systems such as vector DNA.

Single-stranded nucleic acids include antisense oligonucleotides (complementary to DNA and RNA), ribozymes and triplex-forming oligonucleotides. In order to have prolonged activity, the single-stranded nucleic acids will most advantageously have some or all of the nucleotide linkages substituted with stable, non-phosphodiester linkages, including, for example, phosphorothioate, phosphorodithioate, phophoroselenate, or O-alkyl phosphotriester linkages.

The DNA vectors may include nucleic acids in which modifications have been made in one or more sugar moieties and/or in one or more of the pyrimidine or purine bases. Such sugar modifications may include replacement of one or more hydroxyl groups with halogens, alkyl groups, amines, azido groups or functionalized as ethers or esters. In another embodiment, the entire sugar may be replaced with sterically and electronically similar structures, including azasugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

The DNA vector may be modified in certain embodiments with a modifier molecule such as a peptide, protein, steroid or sugar moiety. Modification of a DNA vector with such molecule may facilitate delivery to a target site of interest. In some embodiments, such modification translocates the DNA vector across a nucleus of a target cell. By way of example, a modifier may be able to bind to a specific part of the DNA vector (typically not encoding of the gene-of-interest), but also has a peptide or other modifier that has nucleus-homing effects, such as a nuclear localization signal. A non-limiting example of a modifier is a steroid-peptide nucleic acid conjugate as described by Rebuffat et al., 2002, Faseb J. 16 (11): 1426-8, which is incorporated herein by reference. The DNA vector may contain sequences encoding different proteins or peptides. Promoter, enhancer, stress or chemically-regulated promoters, antibiotic-sensitive or nutrient-sensitive regions, as well as therapeutic protein encoding sequences, may be included as required. Non-encoding sequences may be present as well in the DNA vector.

The nucleic acids used in the present disclosure can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Known procedures for solid phase synthesis of nucleic acids by phosphite-triester, phosphotriester, and H-phosphonate chemistries are widely available.

In one embodiment, the DNA vector is double stranded DNA and comprises more than 700 base pairs, more than 800 base pairs or more than 900 base pairs or more than 1000 base pairs.

Alternatively or additionally, the cargo comprises or encodes a peptide or protein that is part of an editor or forms an editing complex.

The nucleic acid editing complex includes, without limitation, Cas-based (e.g., CRISPR or non-CRISPR), transcription activator-like effector nuclease (TALEN), megaTALs, zinc finger nuclease (ZFN), Adenosine Deaminase Acting on RNA (ADAR), prime editors, base editors, epigenetic, transposase, meganuclease, ARCUS gene editing systems or any variant or combination thereof. These nucleic acid editing systems are exemplary and include any cargo that can modify genetic material (including RNA transcripts and non-coding regions) of a cell to treat, prevent or ameliorate a disorder or disease. Without limitation, the gene editing system may include those that are designed by a process referred to as Directed Nuclease Editor (DNE), which is known to those of skill in the art.

Extrahepatic Nucleic Acid Delivery

As noted, the unshielded lipid nanoparticles herein exhibit similar or improved extrahepatic delivery of nucleic acid to an LNP stabilized with a surface stabilizer such as a hydrophilic polymer (e.g., PEG). In some embodiments, this includes without limitation comparable or improved expression of a coding sequence of an mRNA or a DNA molecule. The lipid nanoparticles of the disclosure may alternatively be used for extrahepatic delivery of antisense oligonucleotide or siRNA for gene silencing.

As used herein, "expression" of an mRNA or DNA sequence refers to translation of a given nucleic acid, such as mRNA or DNA, into a peptide (e.g., an antigen), polypeptide, or protein (e.g., an enzyme) and also can encompass, in certain embodiments, the post-translational modification of the peptide, polypeptide or fully assembled protein (e.g., enzyme).

In one embodiment, the lipid nanoparticle exhibits similar or increased gene expression of the nucleic acid cargo in vivo as measured in an extrahepatic tissue or organ relative to a control having 1.5 mol % PEG-lipid using the procedure of the Examples herein.

In another embodiment, the extrahepatic tissue or organ is spleen, bone marrow, lungs, kidney, heart, abdominal skin, back skin and/or ear. In another embodiment, the extrahepatic tissue or organ is spleen, heart, skin or small intestine.

As described in Example 1, unexpectedly, the non-sterically stabilized LNPs of the disclosure possess similar or even improved nucleic acid expression in extrahepatic organs and/or tissues than otherwise identical PEG-lipid containing formulations for nucleic acid delivery, including but not limited to delivery to the spleen, heart, skin or small intestine.

Whether or not a lipid nanoparticle exhibits such enhanced nucleic acid delivery to a given extrahepatic tissue or organ can be determined by biodistribution studies in an in vivo mouse model. In such embodiments, luciferase may be used to detect nucleic acid expression in a given tissue or organ. In particular, according to such embodiments, LNPs are prepared encapsulating nucleic acid (e.g., mRNA or DNA vector) coding for luciferase and luciferase expression in cell populations in the spleen and bone marrow are evaluated by measuring luminescence following systemic administration.

In particular, to assess whether a given lipid nanoparticle exhibits an increase in gene expression in a relevant tissue or organ at 12 hours, 24 hours, 48 hours or 3 days post-injection, the nucleic acid-LNP of the disclosure is compared to the unshielded LNP herein (e.g., a PEG-less formulation) having identical amounts of ionizable cationic lipid and DSPC of the Examples. The two LNPs being compared are subjected to the same experimental methods and materials to determine in vivo expression as set forth in the Examples.

In one embodiment, the lipid nanoparticle exhibits a similar (e.g. +/−5% increase in gene expression) or an increased mRNA gene expression, such as 5%, 10%, 20%, 30%, 40%, 50% increase in gene expression of an encapsulated mRNA or DNA encoding luciferase as measured in vivo in an extrahepatic organ or tissue post-injection at 12 hours, 24 hours, 48 hours or 3 days as compared to a PEG-containing control formulation of 1/DSPC/cholesterol/$PEG_{2000}$-DMG at 27.4/50/21.1/1.5; mol:mol, (in which $PEG_{2000}$-DMG is included at the expense of 1.5 mol % of cholesterol), wherein the gene expression is measured in a mouse model by detection of the luciferase translated from the mRNA or DNA. The measurement is carried out using a luminometer as set forth in the Examples. The percentage increase is determined by comparing the luminescence signal in each organ after homogenization thereof and comparing the luminescence to the PEG-containing control (having 1.5 mol % $PEG_{2000}$-DMG).

Local Nucleic Acid Administration

The unshielded lipid nanoparticles herein may exhibit similar or improved local delivery of nucleic acid relative to an otherwise identical LNP stabilized with a surface stabilizer, such as a hydrophilic polymer (e.g., $PEG_{2000}$-DMG). In some embodiments, this includes nucleic acid at a local site of injection with reduced off-target levels in the liver relative to a PEG-containing baseline. (E.g., see results in Example 12). The unshielded lipid nanoparticles of the disclosure may also be used for local administration of mRNA, antisense oligonucleotide or siRNA for gene silencing. Various non-limiting examples of local delivery of nucleic acid using the unshielded lipid nanoparticles are set forth below.

In one embodiment, the unshielded LNPs are for intratumoral injection of a nucleic acid therapeutic. For example, the unshielded LNPs herein may be used to deliver nucleic acid for immunotherapy, such as delivery of one or more mRNA encoding immune stimulators to a tumor site to mount an anti-tumour immune response and cause at least partial tumour regression. In some embodiments, the unshielded LNP comprises mRNA(s) that encode(s) for one or more cytokines, including interleukin family members and/or T cell co-stimulators. In some embodiments, the administration of such an unshielded LNP converts a cold tumour to a hot tumour by increasing the inflammatory signature of the tumour to recruit T cells. For example, this may include increasing T cell (e.g., cytotoxic T cell) infiltration and checkpoint activation; see for example Wang et al, 2023, MedComm, 4 (5): e343, and Hewitt et al., 2019, Science Translational Medicine, 11 (477): eaat9143, which are each incorporated herein by reference).

The mRNA may encode an immune modulator that is a cytokine, which in some examples is selected from IL-12, IL-23, IL36γ, IL-27 and/or granulocyte-macrophage colony-stimulating factor (GM-CSF). In another embodiment, the mRNA encodes a gasdermin family protein (GSDM). For example, the mRNA may encode an N-terminal domain of a GSDM protein that causes pyroptosis, which is an inflammatory cell death (see Li et al., 2023, Nature Communications, 14, article number 4223, incorporated herein by reference). In another example, the unshielded lipid nanoparticle encapsulates mRNA encoding tumour necrosis factor-related apoptosis-inducing ligand (TRAIL), which triggers apoptosis upon binding with death receptors (DR4 and DR5). (See Gu et al., 2024, Biomedicine & Pharmacotherapy, 174:116603, incorporated herein by reference). In another example, the lipid nanoparticle encapsulates a nucleic acid encoding a stimulator of interferon genes (STING), such as, without limitation, STING1, which regulates an immune response by transmitting signals that activate type I interferon responses. In one embodiment, STING activates T-cells, such as $CD8^+$ T cells. In some embodiments, the unshielded LNP comprises a plurality of mRNA encoding for more than one immune stimulator. In a further embodiment, the unshielded LNP comprises an antisense oligonucleotide or siRNA against an immune checkpoint inhibitor.

In another embodiment, the unshielded LNP comprising cargo to stimulate the immune system is co-administered with a second therapeutic agent, such as a checkpoint inhibitor. The second therapeutic agent may be encapsulated with a first therapeutic agent in an LNP or administered in a separate pharmaceutical formulation (e.g., an LNP or formulated with a pharmaceutically acceptable salt or carrier).

In one embodiment, the unshielded LNPs comprising nucleic acid are for intracardiac injection. For example, the LNPs comprising nucleic acid can be used for cardiac repair and regeneration. In some embodiments, the LNPs comprising nucleic acid can protect from acute myocardial damage, such as after ischemia or cancer chemotherapy; induce new blood vessel formation, stimulate cardiomyocyte proliferation to increase cardiac mass; treat cardiac inherited conditions, such as by gene editing; and/or treat chronic heart failure. In some embodiments, cardiac LNP delivery is via intracoronary administration.

In one embodiment, the unshielded LNPs comprising nucleic acid are for intraocular injection. In one example, the intraocular injection is selected from intravitreal injection, subretinal or suprachoroidal injection. The intraocular injection may be used in some embodiments to treat age-related macular degeneration, diabetic retinopathy or retinal vein occlusions.

In one embodiment, the unshielded LNPs comprising nucleic acid are for intraosseous injection, in which LNPs are injected directly into the marrow of a bone, such as by infusion. In another embodiment, the unshielded LNPs are for intrafemoral injection. In one example, the unshielded LNPs comprise one or more materials having affinity for a bone microenvironment, such as bisphosphonate.

In one embodiment, the unshielded LNPs comprising nucleic acid are for intra-articular injection, in which LNPs are injected into a joint space. The LNPs for intra-articular injection may be used to treat one of a variety of musculoskeletal conditions, such as osteoarthritis and rheumatoid arthritis.

In one embodiment, the unshielded LNPs comprising nucleic acid are for intrapancreatic injection, in which LNPs are injected directly into the pancreas. In some embodiments, the intrapancreatic injection is to deliver mRNA for protein expression in pancreatic cells, such as beta cells. In some embodiments, the cells transfected in the pancreas are pancreatic islets. In some embodiments, intrapancreatic injection is to treat pancreatic diseases such as pancreatic cancer or diabetes. In alternative embodiments, the unshielded LNP for pancreatic delivery is injected via a bile duct.

In another embodiment, delivery of the unshielded LNPs is via intraperitoneal injection. Intraperitoneal injection may be used to target a variety of tissues or organs. In some embodiments, intraperitoneal injection is used to target immune cells in the intraperitoneal space In one embodiment, the unshielded LNPs comprising nucleic acid are for transtympanic injection. In another embodiment, the unshielded LNP is used to treat hearing impairment. In some embodiments, the unshielded LNP includes nucleic acid for gene editing applications to treat a genetic disease, such as hereditary hearing loss. In another non-limiting example, gene silencing is used to silence genes in the inner ear.

Enhanced Stability and Shelf Stability of Unshielded LNPs

In some embodiments, the unshielded lipid nanoparticle or lipid nanoparticle having no or substantially no hydrophilic polymer-lipid conjugate is characterized as being stable subsequent to vortexing. For example, to determine whether an LNP is stable upon vortexing, an LNP of the disclosure that is unshielded or having no or substantially no hydrophilic polymer-lipid conjugate may be prepared along with a control that is identical except for the incorporation of 1.5 mol % PEG$_{2000}$-DMG in place of 1.5 mol % of the sterol as described in Example 6.

The LNP being examined is then subjected to vortexing at increments ranging from 15 sec-4 min, up to a total of 12 mins of total vortex time. If the LNP has less than 30%, 20% or 10% change in encapsulation of nucleic acid, PDI and/or particle size (nm) after vortexing (within 1 hour of vortexing) as set forth in Example 6, the lipid nanoparticle is considered as being stable subsequent to vortexing.

In some embodiments, the lipid nanoparticle that is unshielded or having no or substantially no hydrophilic polymer-lipid conjugate is characterized as being stable subsequent to the introduction of a stream of air to the lipid nanoparticle (e.g., air bubbles). For example, to determine whether an LNP maintains stability after introduction of an air stream, an LNP of the disclosure that is unshielded or having no or substantially no hydrophilic polymer-lipid conjugate may be prepared along with a control that is identical except for the incorporation of 1.5 mol % PEG$_{2000}$-DMG in place of 1.5 mol % of the sterol as described in Example 6.

The LNP being examined is then subjected to a stream of air for 5 minutes. If the LNP has less than 30%, 20% or 10% change in encapsulation of nucleic acid, PDI and/or particle size (nm) after exposure to the air (within 1 hour of introduction of an air stream) as set forth in Example 7, the lipid nanoparticle is considered as being stable subsequent to exposure to the introduction of the air.

In another embodiment, the LNP has less than 30%, 20% or 10% change in encapsulation of nucleic acid, PDI and/or particle size (nm) after dialysis and after concentration to 0.25 mg/mL subsequent to a step of dialysis as described in Example 4 using the modified ethanol mixing method of the Materials and Methods, the dialysis carried out with sodium acetate or phosphate buffered saline.

In another embodiment, a preparation comprising a plurality of unshielded LNPs does not agglomerate during or after the preparation is made or during/after dialysis. Agglomeration can be observed by the naked eye or can be visualized by Cryo-EM using the procedure set forth in the Materials and Methods herein.

Clinical and Non-Clinical Uses of the Unshielded LNP Herein

In some embodiments, the unshielded or non-sterically stabilized lipid nanoparticle comprising nucleic acid cargo is part of a pharmaceutical composition. The treatment may provide a prophylactic (preventative), ameliorative or a therapeutic benefit to treat any undesirable condition, such as a disease condition or disorder. In other embodiments, the unshielded lipid nanoparticle encapsulates a diagnostic agent. The pharmaceutical composition will be administered at any suitable dosage.

The LNPs described herein may be used to treat and/or prevent any disease, disorder or condition in a mammalian subject. This includes a disease, disorder or condition, such as cancer, infectious diseases such as bacterial, viral, fungal or parasitic infections, inflammatory and/or autoimmune disorders, including treatments that induce immune tolerance and cardiovascular diseases such as hypertension, cardiac arrhythmia and restenosis.

Examples of cancers include lung cancer, colon cancer, rectal cancer, anal cancer, bile duct cancer, small intestine cancer, stomach (gastric) cancer, esophageal cancer; gallbladder cancer, liver cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma.

Non-limiting examples of other diseases, disorders or conditions that may be treated by the nucleic acid-LNPs herein and that may be attributed at least in part to an immunological disorder include colitis, Crohn's disease, allergic encephalitis, allograft transplant/graft vs. host disease (GVHD), diabetes and multiple sclerosis.

The LNP may be part of a vaccine pharmaceutical formulation.

In some embodiments, the nucleic acid in the LNP encodes for a protein, peptide or polypeptide that is non-antigenic for infectious disease, such as a virus. In some embodiments, the LNP is a non-vaccine composition for infectious disease.

The LNPs herein may also be used in other applications besides the treatment and/or prevention of a disease or disorder. The LNPs may be used to treat conditions such as aging, preventative medicine and/or as part of a personalized medicine regime. In further embodiments, the LNP is used in a diagnostic application.

In one embodiment, the LNP is part of a pharmaceutical composition administered parenterally, i.e., intra-arterially, intravenously, subcutaneously or intramuscularly. In yet a further embodiment, the pharmaceutical compositions are for intra-tumoral administration. In another embodiment, the pharmaceutical compositions are administered intranasally, intravitreally, subretinally, intrathecally or via other local routes.

The pharmaceutical composition comprises pharmaceutically acceptable salts and/or excipients.

The compositions described herein may be administered to a patient. The term patient as used herein includes a human or a non-human subject.

Optional Pretreatment to Induce Leukopenia and/or Suppress the Immune System

The method of the disclosure, in some examples, comprises carrying out at a first time point an immunosuppressive pretreatment prior to administration of the unshielded LNPs described herein. The pretreatment induces leukopenia or comprises injection of an immunosuppressive drug.

By the phrase "induces leukopenia", it is meant reducing a patient's white blood cell count in any bodily site, including any organ and/or tissue in the body. In some embodiments, a subject's white blood cell count is reduced in the bloodstream by the pretreatment. Alternatively, or additionally, a subject's white blood cell count is reduced in an organ such as the liver and/or spleen.

Leukopenia may be induced by an agent that causes a reduction in white blood cell count. In some embodiments, leukopenia is induced by an immunosuppressive drug.

As used herein "immunosuppressive drug" is any pharmaceutical compound that suppresses the immune system. In some embodiments, the immunosuppressive drug is a glucocorticoid, a cytostatic, an antibiotic, an antibody or an immunophilin. In another embodiment, the immunosuppressive drug is glucocorticoid, a cytostatic, an antibiotic or any combination thereof. In another embodiment, the immunosuppressive drug is a glucocorticoid or an antibiotic. In another embodiment, the glucocorticoid or antibiotic is encapsulated in a drug delivery vehicle. In a further embodiment, the glucocorticoid or antibiotic is encapsulated in a lipid-based drug delivery vehicle, such as but not limited to a liposome or a lipid nanoparticle.

Non-limiting examples of glucocorticoids are prednisone, dexamethasone and hydrocortisone. Such agents are typically administered to reduce inflammation. In some embodiments, glucocorticoids suppress cell-mediated immunity and/or humoral immunity. For example, the glucocorticoid may inhibit gene expression of cytokines. In some embodiments, the decrease in cytokine production reduces T cell proliferation. In another embodiment, the glucocorticoid suppresses humoral immunity. In some embodiments, the glucocorticoid reduces B cell clone expansion and/or antibody production.

Non-limiting examples of cytostatics are alkylating agents, antimetabolites, cytotoxic antibiotics, antibodies and agents that act on immunophilins. Examples of alkylating agents include nitrogen mustards (cyclophosphamide), nitrosoureas and platinum compounds, among others. Examples of antimetabolites include folic acid analogues (e.g., methotrexate), purine analogues (e.g., azathioprine and mercaptopurine), pyrimidine analogues (fluorouracil), cytotoxic antibiotics (e.g., anthracyclines, such as doxorubicin, daunorubicin, mitoxantrone, epirubicin, aclarubicin and idarubicin, dactinomycin, mitomycin C, bleomycin and methramycin) and protein synthesis inhibitors. Antibodies include without limitation polyclonal antibodies, monoclonal antibodies, T-cell receptor directed antibodies and IL-2 receptor directed antibodies. Drugs acting on immunophilins include ciclosporin, tacrolimus, sirolimus, everolimus and zotarolimus.

In some embodiments, the lipid-based particle comprises aqueous soluble loadable agent(s) of interest in the aqueous portion of the LNP. In other embodiments, the LNP comprises hydrophobic or lipophilic loadable agent(s) of interest, e.g., therapeutic, diagnostic, and/or theranostic agent(s), or prodrugs thereof, present in the lipid portion of the LNP. The loadable agents of interest may be any molecule of interest, e.g., small molecules (e.g., small molecule drugs, imaging agents, and the like), proteins (e.g., antibodies and the like), peptides or nucleic acids.

Without intending to be limiting, the pH gradient loadable agent may be an anti-neoplastic agent. Non-limiting examples of anti-neoplastic agents that can be loaded into lipid-based particles, such as liposomes, by the pH gradient loading method and that therefore may be used in practice of this disclosure include, but are not limited to anthracycline antibiotics such as doxorubicin, daunorubicin, mitoxantrone, epirubicin, aclarubicin and idarubicin; anti-neoplastic antibiotics such as mitomycin, bleomycin and dactinomycin; vinca alkaloids such as vinblastine, vincristine and navelbine; purine derivatives such as 6-mercaptopurine and 6-thioguanine; purine and pyrimidine derivatives such as 5-fluorouracil; camptothecins such as topotecan, irinotecan, lurtotecan, 9-aminocamptothecin, 9-nitrocamptothecin and 10-hydroxycamptothecin; cytarabines such as cytosine arabinoside; antimicrobial agents such as ciprofloxacin and salts thereof.

In another embodiment, the immunostimulatory drug is a pro-drug and the pro-drug is incorporated in the particle during formation thereof. For example, the pro-drug may be lipid-drug conjugate. An example of such a lipid-drug conjugate is a dexamethasone prodrug. Such pro-drugs are well known to those of ordinary skill in the art.

In another embodiment, the lipid-based drug delivery vehicle comprising the immunostimulatory drug has a diameter of less than 230 nm. In one embodiment, the particle size distribution is such that at least 90% of the particles in the LNP preparation of the disclosure have a diameter of between 40 nm and 230 nm, between 45 and 200 nm or between 50 and 175 nm.

In another embodiment, the lipid-based drug delivery vehicle comprising the immunostimulatory drug is substantially uncharged or comprises less than 10 mol % of an anionic lipid. In one embodiment, the lipid-based drug delivery vehicle comprising the immunostimulatory drug comprises less than 9 mol %, 8 mol %, 7 mol %, 6 mol % or 5 mol % of an anionic lipid.

In another embodiment, the pretreatment comprises leukapheresis, which is a physical method to reduce white blood cell count. The method comprises withdrawing blood from the subject, separating white blood cells from the blood and introducing the blood from which white blood cells are withdrawn back to the subject. Continuous processing may include feeding whole blood into a channel designed for separation of white blood cells, red blood cells and plasma are pumped back to the subject and targeted cells, namely white blood cells, are pumped into a collection bag. An example of an apparatus for white blood cell depletion is a Spectra Optia™ apheresis system.

The examples below are intended to illustrate the preparation of specific lipid nanoparticle mRNA preparations and properties thereof but are in no way intended to limit the scope of the invention.

The examples are intended to illustrate the preparation of specific lipid nanoparticle preparations and properties thereof but are in no way intended to limit the scope of the invention.

The article "a" or "an" as used herein is meant to include both singular and plural, unless otherwise indicated.

EXAMPLES

Materials and Methods

Unmodified LNP preparation method

Unless otherwise specified, the LNPs were prepared by dissolving mRNA or plasmid DNA (pDNA) in 25 mM sodium acetate, pH 4.0, while the lipid components at the mole % specified were dissolved in absolute ethanol. The lipids in ethanol and the nucleic acid cargo in buffer were combined in a 1:3 volume by volume ratio using a t-junction with dual-syringe pump. The solutions were pushed through the t-junction at a combined flow rate of 20 mL/min (5 mL/minute for the lipid-containing syringe, 15 mL/minute for the mRNA-containing syringe). The mixture was subsequently dialyzed overnight against at least ~100 volumes of 1× phosphate buffered saline (PBS), pH 7.4 using Spectro/Por™ dialysis membranes (molecular weight cut-off 12 000-14 000 Da). The LNPs were concentrated as required with an Amicon Ultra™ 100 000 MWCO (molecular weight cut-off), regenerated cellulose concentrator.

Encapsulation efficiency was calculated by determining unencapsulated mRNA content by measuring the fluorescence upon the addition of RiboGreen™ to the mRNA-LNP ($F_i$) and comparing this value to the total mRNA content that is obtained upon lysis of the LNP by 2% Triton X-100 ($F_t$): % encapsulation=$(F_t-F_i)/F_t \times 100$.

The particle size and polydispersity index (PDI) were characterized using a Zetasizer Nano ZS™.

Modified LNP Preparation Method

The above LNP preparation was modified to formulate ionizable lipids that were otherwise not capable of being formulated without the inclusion of $PEG_{2000}$-lipid using the standard LNP preparation method described above (see Example 4). After T-mixing, 1× phosphate buffered saline (PBS) or other buffer as indicated, was added to the formulation mixture in increasing ratios of LNP: 1× buffer prior to dialysis and gently mixed, followed by transfer to dialysis in 1×PBS (or other suitable buffer as indicated) followed by processing as usual.

Tissue Homogenate Assay

The LNPs at a luciferase mRNA or pDNA concentration of 0.1 mg/mL were injected intravenously (i.v.) in mice. Organs were harvested at 24 hours after the LNP injections.

Tissues were removed from the mice and placed in 2 mL tubes and snap frozen in liquid nitrogen. The tissues were subsequently stored at −80° C. An appropriate volume of GLO™ lysis buffer from Promega™ was added to each of the tubes, ensuring that the samples remained frozen before addition of the lysis buffer. Samples were placed in a FastPrep™ homogenizer and the homogenizer was operated at a speed of 6 m/s for 20 seconds and repeated 2 times for a total of three rounds. The homogenized samples were spun down for 10 minutes at 12,000 rpm at room temperature and subsequently 50 μL of homogenate in duplicate was added to a black plate. The plate was transferred to a plate reader and the fluorescence was read at 640 nm excitation/720 nm emissions. Luminescence was determined by adding 50 μL of Steady Glo™ substrate into the homogenate sample and a luciferase signal was read.

Cryo-TEM

LNPs were concentrated to between 15-25 mg/mL estimated total lipid prior to cryo-TEM imaging. A defined volume, for example 2-4 μL, of the resulting LNP solution was applied to a glow-discharged copper grid, and plunge-frozen using an FEI Mark IV Vitrobot™ to generate vitreous ice. These grids were stored in liquid nitrogen until imaged by an FEI Titan Krios™ or an FEI Glacios TEM™. The instrument was operated at 200 kV in low-dose conditions and the resulting images were obtained using a bottom-mount FEI Falcon™ direct electron detector camera at 47-88,000× magnification with an under-focus of 0.5-2 μm in order to enhance contrast.

In Vivo Imaging

LNPs encapsulating mRNA encoding luciferase were injected at time 0 to three mice. Shortly prior to imaging, D-luciferin (as listed in Cayman™ chemicals catalog #14681) was administered to the mice at a dose of 150 mg/kg intraperitoneally. A 15 mg/mL stock of D-luciferin was prepared using 1× Dulbecco's Phosphate Buffered Saline (containing no calcium or magnesium) and 10 μL/gram of body weight was administered intraperitoneally to each of the mice.

At 4 and 24 hours after LNP injection, the mice were anesthetized using 2.5-3% isoflurane in a chamber and were subsequently placed on the imaging platform maintained under 2% isoflurane through a nose cone.

All mice were imaged 10 mins post D-luciferin injection at an exposure time of 15 seconds. Bioluminescence imaging was performed using IVIS® Lumina II In Vivo Imaging System (IVIS). An untreated mouse was used as a negative control for background luminescence.

Immune Response Studies

Mice (C57BL6) that were 6-8 weeks old were injected intramuscularly with the indicated doses of LNPs. Mice were injected intramuscularly (IM) at Day 0 (prime dose) and at Day 21 (boost dose). Blood samples were collected by saphenous bleeds at 6 hours post IM injections for innate immune responses and at 21 days (prime IgG levels) post IM injections for prime serum IgG levels. At 35 days post IM injection (terminal end point), blood samples were collected by cardiac puncture to measure boost serum IgG levels. Prime and boost serum IgG levels were measured using Mesoscale Discovery (MSD). Neutralizing antibodies that inhibit the binding of angiotensin converting enzyme 2 (ACE2) to receptor binding domain (RBD) of spike protein were measured using MSD. Serum samples taken at 6 hours were used to measure levels of cytokines for innate immune responses. At day 35 post IMs, spleens were extracted and splenocytes were isolated to determine T cell responses. T cell responses were measured by stimulating splenocytes ex vivo with a spike peptide pool. IFN-g/IL-4 enzyme-linked immunospot (ELISpot™) and intracellular cytokine staining were used to measure T cell responses.

T7 Endonuclease Detection Assay

To assess the efficiency of TCR genomic cleavage, the GeneArt Genomic Cleavage Detection Kit (Invitrogen) was utilised. 48 hours post LNP treatment, genomic DNA extraction was performed using DNeasy Blood and Tissue Kit (QIAGEN). PCR was performed to amplify a 600 bp region covering the TCR cut site and purified using Monarch PCR & DNA Cleanup Kit (NEW ENGLAND Biolabs). 60 ng of DNA was heated to 95° C. for 5 minutes before cooling to 25° C. to generate heteroduplex DNA. The DNA was then incubated for 1 hour at 37° C. with Detection enzyme before being subject to agarose gel electrophoresis.

Interference of CRISPR Editing (ICE)

For assessment of INDEL and knockout efficiency, the PCR amplified and purified DNA samples used for the T7 endonuclease detection assay were sent to Source Bioscience for Sanger sequencing. The resulting Sanger sequencing data was analyzed using Synthego's ICE algorithm, providing the frequency of INDELs (INDEL %) and the contribution which will produce a frameshift and therefore a functional knockout (Knockout score).

Flow Cytometry In Vivo Studies

The LNPs at the eGFP mRNA concentration of 1.0 mg/mL were injected intravenously (i.v.) in mice at a volume using the formula weight of the mouse (in grams) *10 µL. Bone marrow and blood was harvested 24 hours after the LNP injections.

The bone marrow was harvested and processed into a single cell suspension. In particular, the mice were anesthetized with 5% isoflurane until reflex was lost and then exposed to $CO_2$ with 1% air. The marrow was isolated from the femur by centrifugation of the bone for 30 s at 3,810 g and resuspended in FACS buffer (1× sterile PBS (pH 7.4), 2.5 mM ethylenediaminetetraacetic acid (EDTA), 0.05% (w/v) sodium azide ($NaN_3$), 2% (v/v) heat-inactivated fetal bovine serum (HI—FBS)). The bone marrow was then washed once in FACS buffer before final resuspension.

After isolation, the bone marrow and/or blood cells were stained. One to three million cells were added to a well of 96-well round bottom plates and the volume in each well was increased to 150 µL using FACS buffer. Cells were centrifuged at 484 g at 4° C. for 5 minutes and the liquid was discarded. Subsequently, cells were incubated with Fc block and then a solution containing staining antibodies for 45 minutes. Cells were centrifuged at 484 g at 4° C. for 5 minutes and the liquid was discarded. The volume was increased to 150 µL and cells were centrifuged at 484 g at 4° C. for 5 minutes and the liquid was discarded twice. A volume of 150 µL of propidium iodide (PI) was added at a 1:5,000 dilution (1 mg/mL stock) and the stained, single cells were introduced to a flow cytometer (Cytoflex™, Beckman Coulter™). Single colour set-ups were used to generate the compensation matrix which was applied to all the samples.

The blood was harvested and processed into a single cell suspension. In particular, the mice were anesthetized with 5% isoflurane until reflex was lost and then exposed to $CO_2$ with 1% air. The blood was harvested via immediate cardiac puncture and added to 0.5 mL of 0.5M EDTA solution. The blood-EDTA solution was then transferred to 12 mL of pre-warmed 1× RBC Lysis buffer and incubated in a 37 C water bath for 5 minutes. Cells were then centrifuged at 484 g at 4° C. for 5 minutes and the liquid was discarded. Blood cells were then washed in FACS buffer (1× sterile PBS (pH 7.4), 2.5 mM ethylenediaminetetraacetic acid (EDTA), 0.05% (w/v) sodium azide ($NaN_3$), 2% (v/v) heat-inactivated fetal bovine serum (HI—FBS)) and resuspended in a final volume of FACS buffer.

The flow cytometry data was analyzed using FlowJo™ version 10 (Becton Dickinson™ & Company (BD)). Corresponding T cell sub-sets were identified based on an appropriate gating scheme.

Ex Vivo eGFP, TCR and CD3 Flow Cytometry

For ex vivo analysis of GFP or TCR and CD3 expression, purified CD4+ or CD8+ T cells (Stem Cell Technologies) were stained for flow cytometry analysis. 1 million cells were centrifuged for 5 minutes at 300× g and washed with FACS buffer (5% FBS, 2 mM EDTA in 1× sterile PBS (pH 7.4)) before staining in 100 mL FACS buffer for 30 minutes at 4° C. with the following reagents: Zombie Violet viability dye, PE anti-human CD3, Alexa Fluor 488 anti-human TCRa/b. Cells were washed 2× in FACS buffer before acquisition on a BD FACSMelody™ flow cytometer. An ex vivo representative flow cytometry gating strategy is provided in FIG. 2.

The bar graphs for the percentage of eGFP positive (eGFP+) cells were generated using Prism™ version 8 (GraphPad™) software.

Ex Vivo GFP Knock-Out/Knock-In

For GFP knock-in studies, LNPs were prepared at a 1:1:3 weight ratio of Cas9 mRNA:TCR gRNA:GFP HDR DNA. $1\times10^6$ Primary CD4+ cells were treated with an RNA dose of 2.5 µg for 48 hours with or without co-treatment with a HDR enhancer (M3814). Cells were expanded and analysed for TCR KO and GFP knock-in (KI) at 7 days post LNP treatment. For flow cytometry analysis, $1\times10^6$ cells were centrifuged for 5 minutes at 300× g and washed with FACS buffer (5% FBS, 2 mM EDTA in 1× sterile PBS (pH 7.4)) before staining in 100 µl FACS buffer for 30 minutes at 4° C. with the following reagents: Zombie Violet viability dye, APC anti-human TCRa/b. Cells were washed 2× in FACS buffer before acquisition on a BD FACSMelody™ flow cytometer. The percentage of TCR KO and GFP KI were calculated from the preceding viable cell population.

Example 1: High PC-Containing LNPs of the Disclosure Lacking PEG (Unshielded) were Found to Exhibit Favourable Biophysical Characteristics and Enhanced Storage Stability This example examines the effect of reducing the PEG-lipid content on the physical properties of lipid nanoparticles having elevated phosphatidylcholine (50 mol %), 17.6 to 22.6 mol % sterol and PEG-lipid between 0 and 5 mol %. The formulation characteristics tested included particle size, polydispersity index (PDI), encapsulation % and storage stability.

LNPs having various molar concentrations of $PEG_{2000}$-DMG (0 to 5 mol %) were prepared as described in the Materials and Methods. The nucleic acid cargo was plasmid DNA (pDNA) or mRNA encoding for firefly luciferase and the N/P for each formulation was 9. The formulations tested are provided in Table 1 below.

TABLE 1

Nucleic acid-LNP formulations tested for biophysical characteristics with decreasing amounts of PEG-lipid

| LNP | Ionizable lipid mol % (1) See WO 2022/246571A1 | Phosphatidylcholine mol % (DSPC) | Cholesterol mol % | PEG-lipid mol % |
|---|---|---|---|---|
| A | 27.4 1 | 50 DSPC | 22.6 | 0 |
| B | 27.4 1 | 50 DSPC | 22.5 | 0.1 |
| C | 27.4 1 | 50 DSPC | 22.4 | 0.2 |
| D | 27.4 1 | 50 DSPC | 22.3 | 0.3 |
| E | 27.4 1 | 50 DSPC | 22.1 | 0.5 |
| F | 27.4 1 | 50 DSPC | 21.85 | 0.75 |
| G | 27.4 1 | 50 DSPC | 21.6 | 1.0 |
| H | 27.4 1 | 50 DSPC | 21.1 | 1.5 |
| I | 27.4 1 | 50 DSPC | 20.6 | 2 |
| J | 27.4 1 | 50 DSPC | 19.6 | 3 |
| K | 27.4 1 | 50 DSPC | 17.6 | 5 |

Figure 1A:
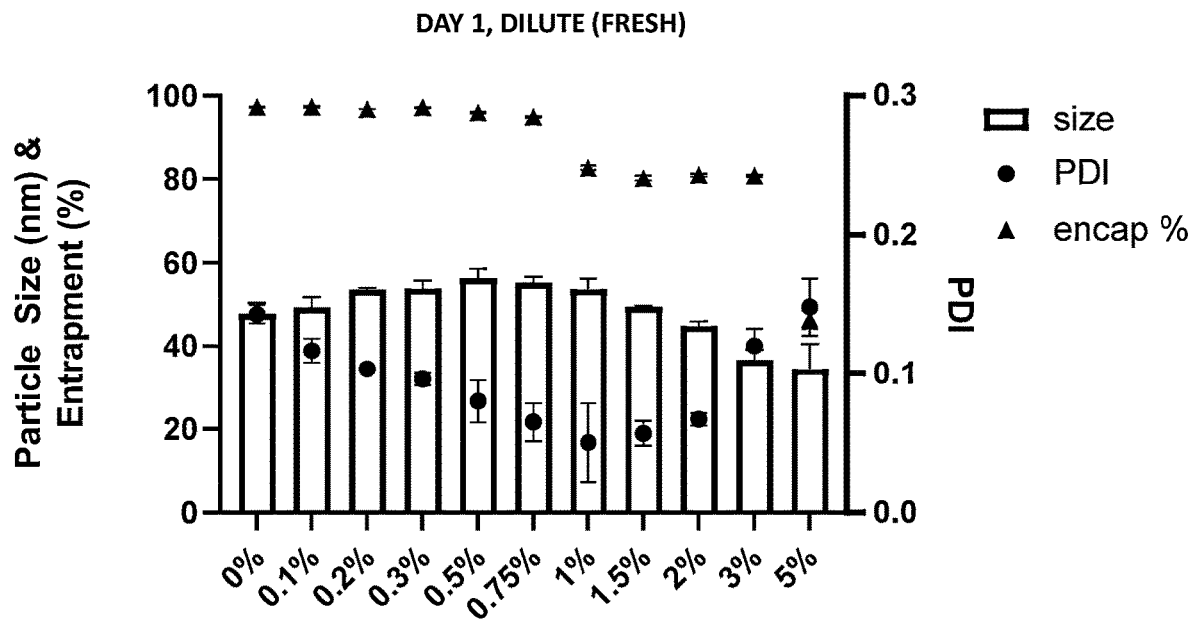
FIG. 1A is a graph showing encapsulation efficiency (%), particle size (nm) and polydispersity index (PDI) of lipid nanoparticle (LNP) formulations of 1 ionizable lipid/DSPC/Chol/PEG$_{2000}$-DMG) at respective mol % ratios of 27.4/50/22.6-X/X encapsulating plasmid DNA (pDNA) encoding for luciferase as a function of decreasing PEG content. The PEG-lipid content (represented by X) was decreased from 5 to 0 mol %. The nitrogen-to-phosphate (N/P) ratio was 9 and the sample was undiluted and measured at day 1 (fresh).
Figure 1B:
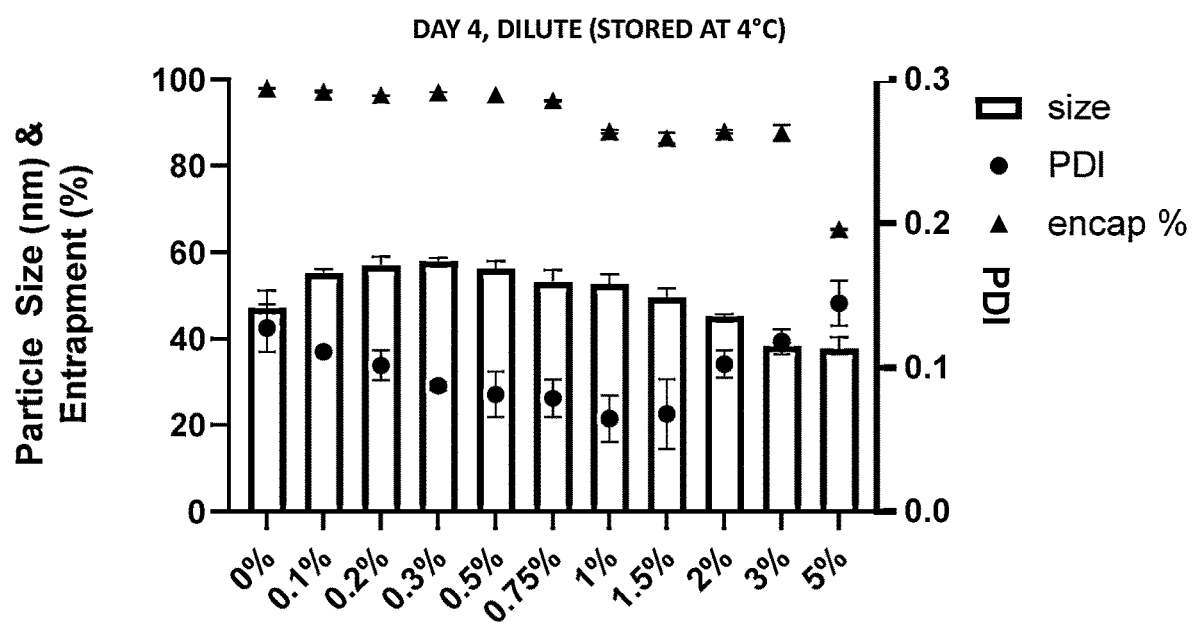
FIG. 1B is a graph showing encapsulation efficiency (%), particle size (nm) and polydispersity index (PDI) of lipid nanoparticle (LNP) formulations of 1 ionizable lipid/DSPC/Chol/PEG$_{2000}$-DMG) at respective mol % ratios of 27.4/50/22.6-X/X encapsulating plasmid DNA encoding for luciferase as a function of decreasing PEG content. The PEG-lipid content (represented by X) was decreased from 5 mol % to 0 mol %. The nitrogen-to-phosphate (N/P) ratio was 9 and the sample was stored at 4° C. and biophysical characteristics measured at day 4.
Figure 1C:
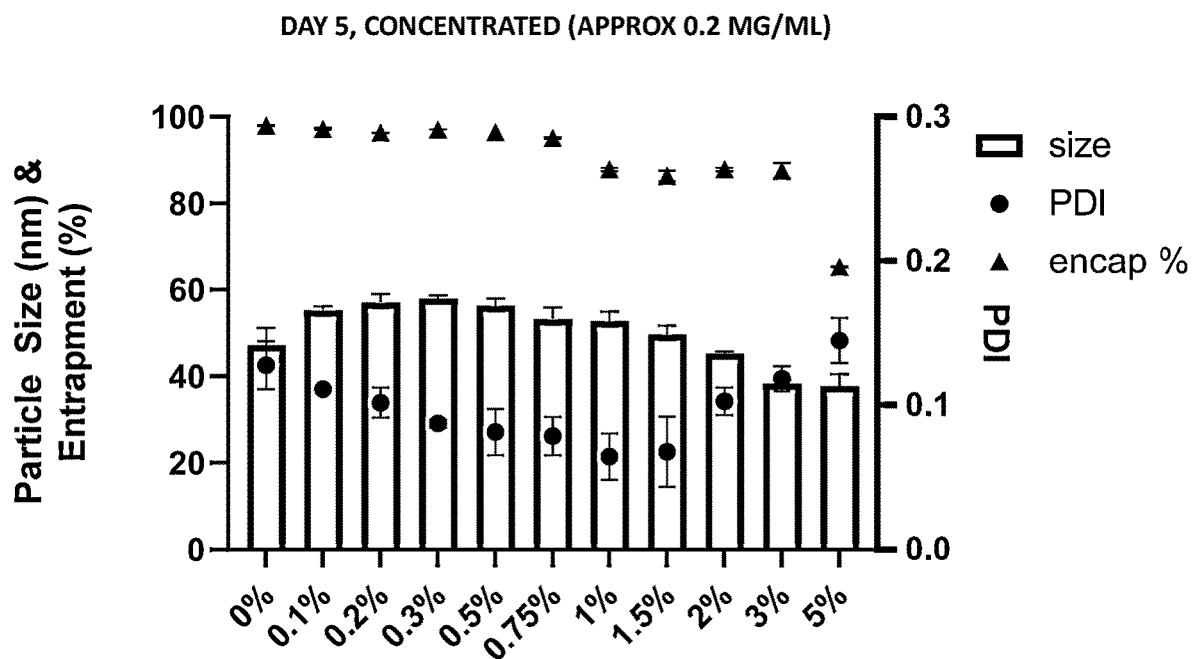
FIG. 1C is a graph showing encapsulation efficiency (%), particle size (nm) and polydispersity index (PDI) of lipid nanoparticle (LNP) formulations of 1 ionizable lipid/DSPC/Chol/PEG$_{2000}$-DMG) at respective mol % ratios of 27.4/50/22.6-X/X encapsulating plasmid DNA (pDNA) encoding for luciferase as a function of decreasing PEG content. The PEG-lipid content (represented by X) was decreased from 5 mol % to 0 mol %. The nitrogen-to-phosphate (N/P) ratio was 9 and the sample was stored at 4° C. and biophysical characteristics measured at day 5 after concentration to 0.2 mg/mL.

FIGS. 1A-C show the effect of decreasing the mol % of PEG-lipid in pDNA-LNPs having 50 mol % DSPC and 27.4 mol % ionizable lipid. The lipid nanoparticles were prepared at respective mol % ratios of 27.4/50/22.6-X/X ionizable lipid/DSPC/chol/$PEG_{2000}$-DMG, in which X is PEG-lipid and varied from 0-5 mol %.

Unexpectedly, the PEG-free LNPs (LNP A) or LNPs having less than 1.5 mol % PEG (LNPs B-G) all exhibited favourable size, PDI and encapsulation efficiency (%). As shown in FIG. 1A, each of the formulations with 0-0.75 mol % of PEG-lipid had an encapsulation efficiency that approached 100%. The LNPs without PEG or having low levels thereof also exhibited favourable PDI values (less than 0.15) and a suitable particle size.

Unexpectedly, similar results were observed after prolonged storage of the particles at 4° C. over 4 days (FIG. 1B). These results are unexpected since PEG is generally thought to prevent particle agglomeration upon storage. It was found that the LNPs having high PC content retained their size and PDI, as well as encapsulation of the pDNA cargo. Yet further, after concentration of the LNPs on day 5 to approximately 0.2 mg/mL, the particles still retained favourable biophysical characteristics (FIG. 1C).

Next, the inventors tested whether similar results would be observed with mRNA LNPs. LNP formulations having PEG-lipid contents of 0-5 mol % and elevated levels of DSPC and cholesterol were prepared encapsulating mRNA encoding for luciferase. The mRNA-containing formulations tested were the same library as examined for the pDNA formulation studies and are set out in Table 1 above.

Figure 2A:
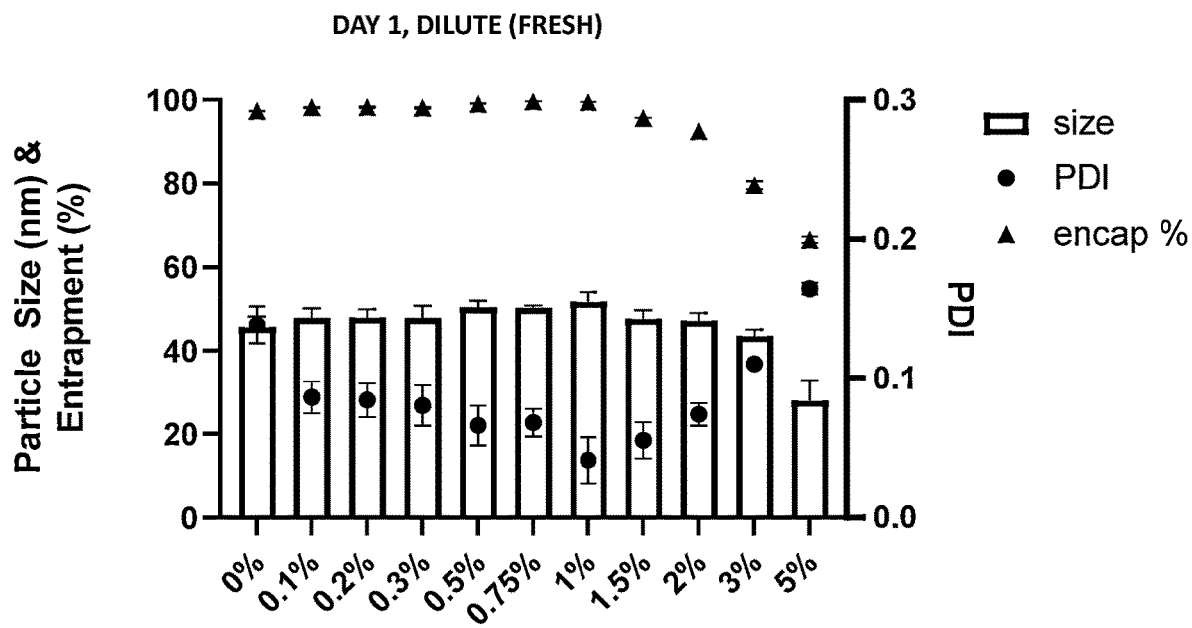
FIG. 2A is a graph showing encapsulation efficiency (%), particle size (nm) and polydispersity index (PDI) of lipid nanoparticle (LNP) formulations of 1 ionizable lipid/DSPC/Chol/PEG$_{2000}$-DMG) at respective mol % ratios of 27.4/50/22.6-X/X encapsulating mRNA encoding for luciferase as a function of decreasing PEG content. The PEG-lipid content (represented by X) was decreased from 5 to 0 mol %. The nitrogen-to-phosphate (N/P) ratio was 9 and the sample was undiluted and measured at day 1 (fresh).
Figure 2B:
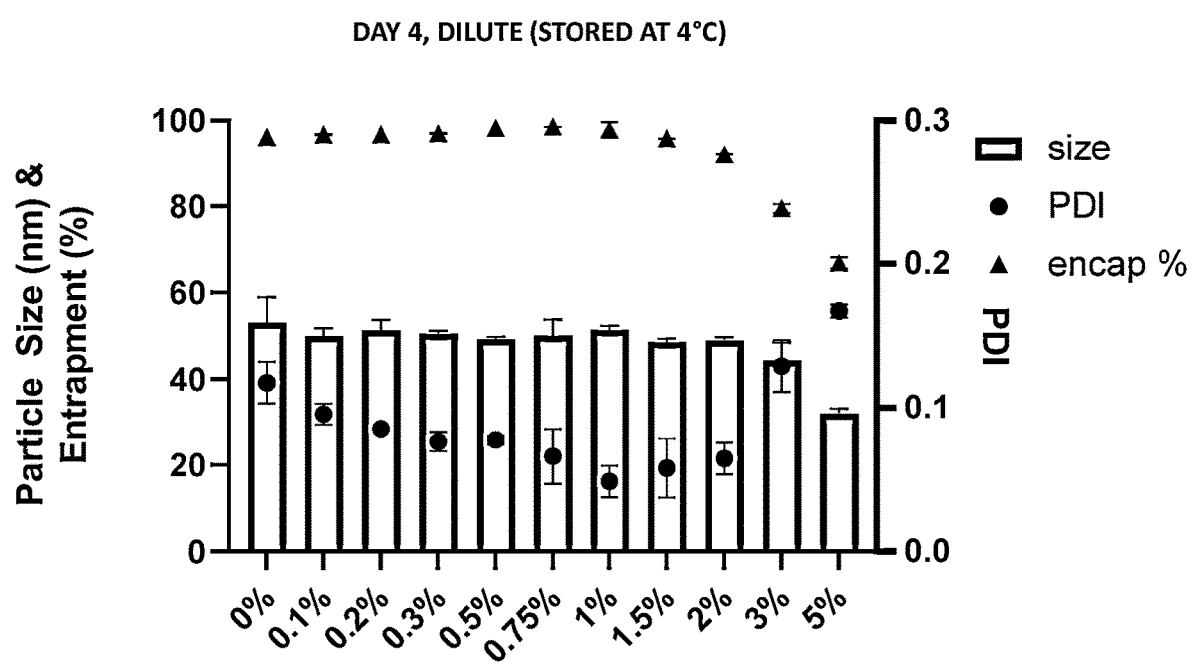
FIG. 2B is a graph showing encapsulation efficiency (%), particle size (nm) and polydispersity index (PDI) of lipid nanoparticle (LNP) formulations of 1 ionizable lipid/DSPC/Chol/PEG$_{2000}$-DMG) at respective mol % ratios of 27.4/50/22.6-X/X encapsulating mRNA encoding for luciferase as a function of decreasing PEG content. The PEG-lipid content (represented by X) was decreased from 5 mol % to 0 mol %. The nitrogen-to-phosphate (N/P) ratio was 9 and the sample was stored at 4° C. and biophysical characteristics measured at day 4.
Figure 2C:
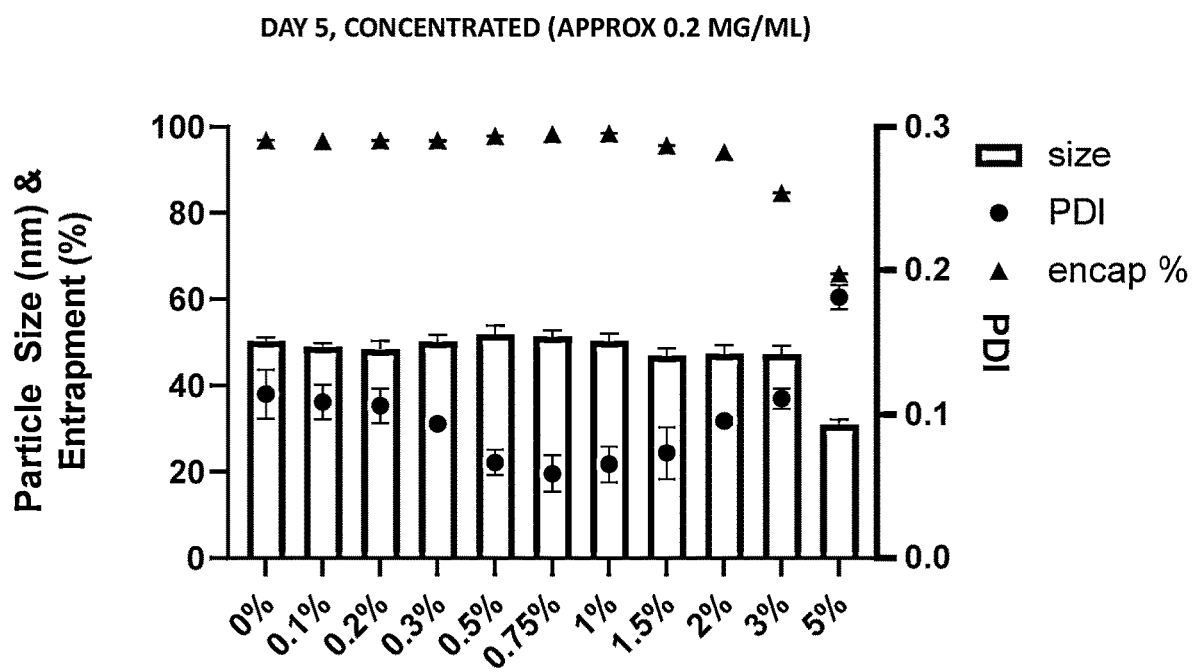
FIG. 2C is a graph showing encapsulation efficiency (%), particle size (nm) and polydispersity index (PDI) of lipid nanoparticle (LNP) formulations of 1 ionizable lipid/DSPC/Chol/PEG$_{2000}$-DMG) at respective mol % ratios of 27.4/50/22.6-X/X encapsulating mRNA encoding for luciferase as a function of decreasing PEG content. The PEG-lipid content (represented by X) was decreased from 5 mol % to 0 mol %. The nitrogen-to-phosphate (N/P) ratio was 9 and the sample was stored at 4° C. and biophysical characteristics measured at day 5 after concentration to 0.2 mg/mL.

Similar favourable formulation characteristics were observed for the LNP formulations encapsulating mRNA as for the pDNA LNPs. As shown in FIG. 2A, the PEG-free LNPs (LNP A) or LNPs encapsulating mRNA and having less than 1.5 mol % PEG (LNPs B-G) all exhibited favourable size, PDI and encapsulation efficiency (%). The size, PDI and encapsulation percentages remained consistent at day 3 stored at 4° C. and day 3 after concentration to 0.2 mg/mL, thereby demonstrating that, similar to the pDNA particles, the mRNA LNPs remained stable after storage and concentration.

Example 2: Unshielded LNPs Containing Elevated Phosphatidylcholine and Reduced Levels of Ionizable Lipid were Found to Exhibit Extrahepatic Delivery of Nucleic Acid Cargo This example demonstrates that a PEG-less LNP with elevated phosphatidylcholine displayed similar or better extrahepatic delivery of nucleic acid cargo to the same LNP stabilized with 1.5 mol % PEG. These results are unexpected as PEG is known to improve the circulation lifetime of nucleic acid LNPs in order to bypass the liver and reach extrahepatic organs and tissues.

The two LNP formulations tested are set forth in Table 2 below. The LNPs were formulated as described in Example 1. The cargo was mRNA encoding for firefly luciferase and the N/P was 9.

TABLE 2

Nucleic acid-LNP formulations tested for extrahepatic delivery

| LNP | Ionizable lipid mol % (see WO 2022/246571A1) | Helper lipid mol % | Chol mol % | PEG mol % |
|---|---|---|---|---|
| A | 27.4 1 | 50 DSPC | 21.1 | 1.5 |
| B | 27.4 1 | 50 DSPC | 22.6 | 0 |

Figure 3:
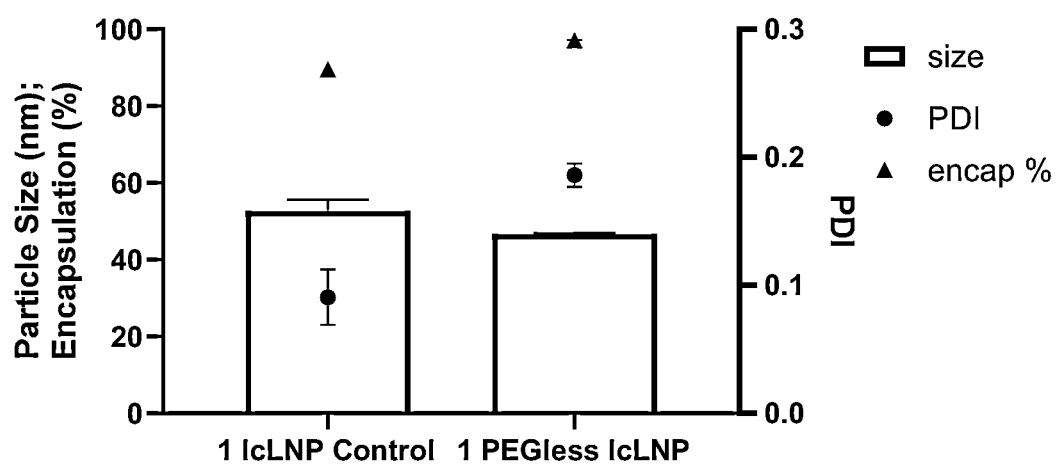
FIG. 3 is a graph comparing entrapment (%), particle size (nm) and PDI of an LNP containing 1.5 mol % PEG (control lcLNP) and an LNP lacking PEG (PEGless lcLNP) encapsulating firefly luciferase mRNA. The PEG-containing formulation was 1/DSPC/cholesterol/PEG$_{2000}$-DMG (27.4/50/21.1/1.5 mol/mol) and the formulation lacking PEG was 1/DSPC/cholesterol/PEG$_{2000}$-DMG (27.4/50/22.6/0 mol/mol). The nitrogen-to-phosphate (N/P) ratio was 9.

Formulation A and B both exhibited favourable size, PDI and encapsulation efficiency (%). The physiochemical characteristics are shown in FIG. 3.

The in vivo results shown in FIG. 4A-G illustrate that luminescence intensity of luciferase expressed from the mRNA was comparable between the PEG-containing and PEG-less formulations A and B (FIG. 4A). Comparable delivery between the two formulations was observed in the spleen, heart and bone marrow. Remarkably, improved delivery for the PEG-less formulation over the PEG-containing formulation was observed in the skin and small intestine.

Example 3: A Range of Different Ionizable Cationic Lipids can be Formulated in Unshielded LNPs (PEG-Less) Containing Elevated Phosphatidylcholine and Reduced Levels of Ionizable Lipid This example demonstrates that a variety of ionizable cationic lipids can be formulated in a PEG-less LNP formulation with elevated phosphatidylcholine using the ethanol rapid mixing method.

LNP formulations having 27.4/50/22.6 (mol/mol) of ionizable lipid/DSPC/chol were prepared as described in the Materials and Methods. The ionizable cationic lipids formulated in the PEG-less LNPs are described in Table 3 below:

TABLE 3
Ionizable lipids formulated in PEG-less LNPs
| Ionizable lipid | Structure |
|---|---|
| 1 | 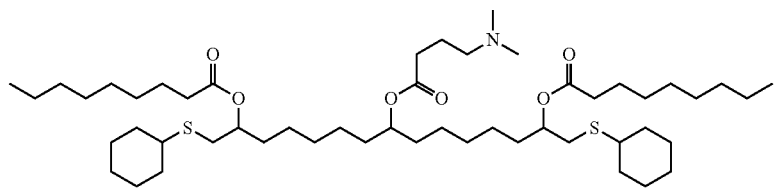 [SMILES: CCCCCCCCC(=O)OC(CCCCCC(CCCCCC(CSC1CCCCC1)OC(=O)CCCCCCCC)OC(=O)CCCN(C)C)CSC1CCCCC1] |
| 2 | 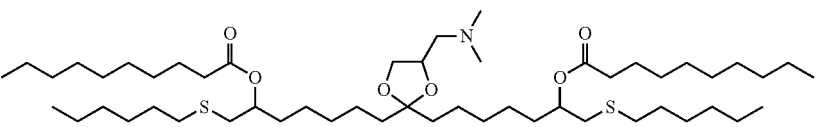 [SMILES: CCCCCCCCCC(=O)OC(CCCCCC1(C(C)CCCCC(C)(CSCCCCCC)OC(=O)CCCCCCCCC)OCC(CN(C)C)O1)CSCCCCCC] |
| 3 | 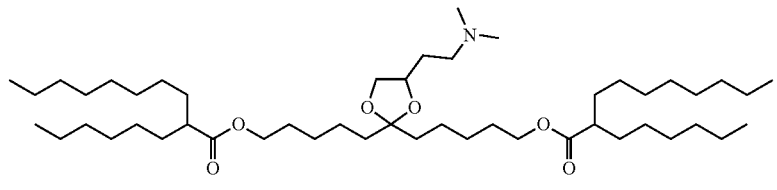 [SMILES: CCCCCCCCC(CCCCCC)C(=O)OCCCCCC1(C(C)CCCCOC(=O)C(CCCCCC)CCCCCCCC)OCC(CCN(C)C)O1] |
| 4 | 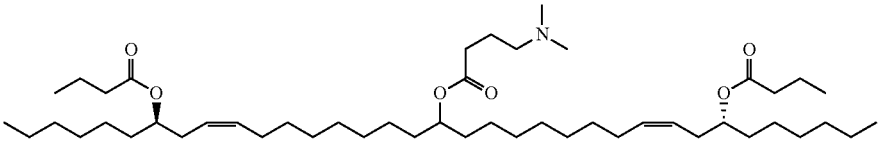 [SMILES: CCCCCC[C@H](C/C=C\CCCCCCCC(CCCCCCC/C=C\C[C@@H](CCCCCC)OC(=O)CCC)OC(=O)CCCN(C)C)OC(=O)CCC] |
| 5 | 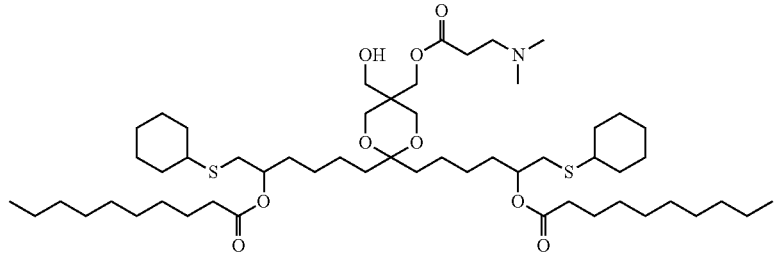 [SMILES: CCCCCCCCCC(=O)OC(CCCCC1(CCCCC(CSC2CCCCC2)OC(=O)CCCCCCCCC)OCC(CO)(COC(=O)CCN(C)C)CO1)CSC1CCCCC1] |
| 6 | 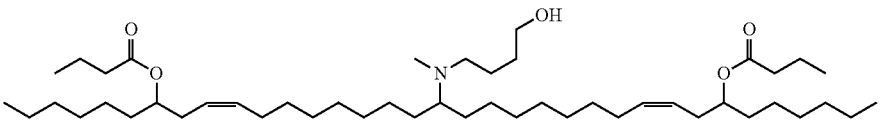 [SMILES: CCCCCCC(C/C=C\CCCCCCCC(CCCCCCC/C=C\CC(CCCCCC)OC(=O)CCC)N(C)CCCCO)OC(=O)CCC] |
| 7 | 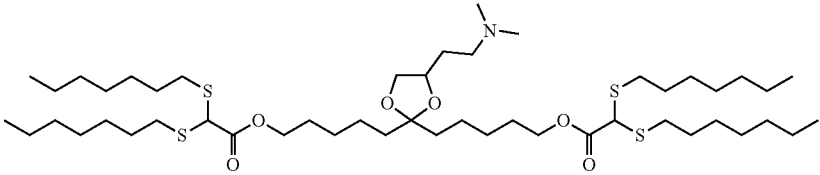 [SMILES: CCCCCCCSC(SCCCCCCC)C(=O)OCCCCCC1(CCCCCOC(=O)C(SCCCCCCC)SCCCCCCC)OCC(CCN(C)C)O1] |
| 8 | 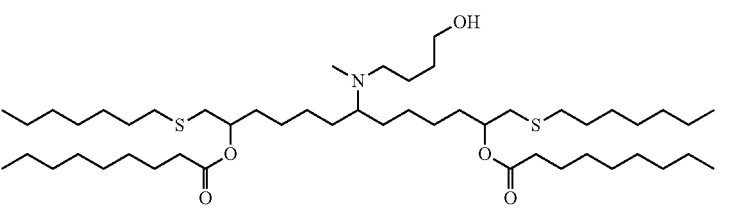 [SMILES: CCCCCCCCC(=O)OC(CCCCC(CCCCC(CSCCCCCCC)OC(=O)CCCCCCCC)N(C)CCCCO)CSCCCCCCC] |

TABLE 3-continued

Ionizable lipids formulated in PEG-less LNPs

| Ionizable lipid | Structure |
|---|---|
| 9 | 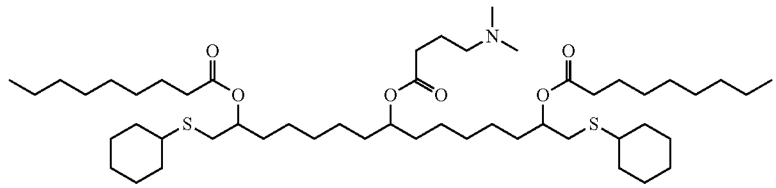 [SMILES: CCCCCCCCC(=O)OC(CCCCCC(CCCCCC(CSC1CCCCC1)OC(=O)CCCCCCCC)OC(=O)CCCN(C)C)CSC1CCCCC1] |
| 10 | 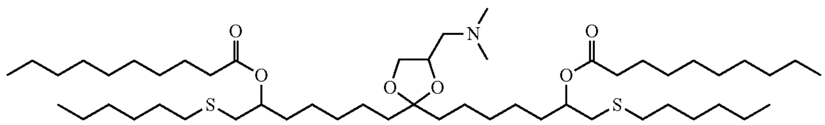 |
| 11 | 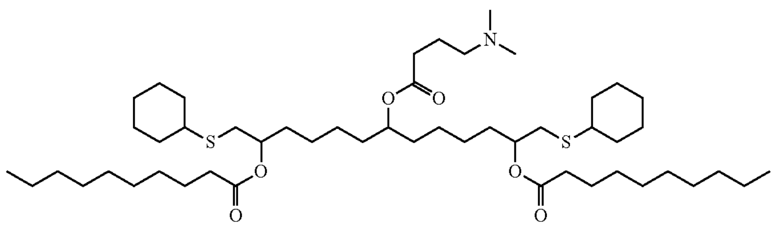 [SMILES: CCCCCCCCCC(=O)OC(CCCCC(CCCCC(CSC1CCCCC1)OC(=O)CCCCCCCCC)OC(=O)CCCN(C)C)CSC1CCCCC1] |
| 12 | 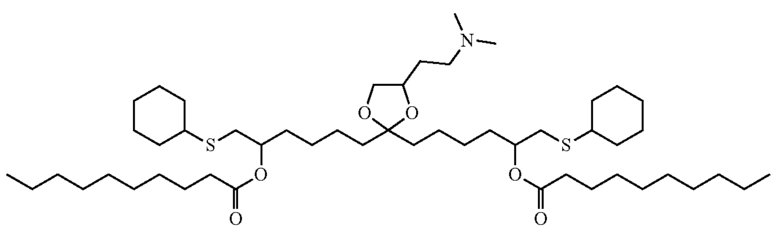 [SMILES: CCCCCCCCCC(=O)OC(CCCCC1(CCCCC(CSC2CCCCC2)OC(=O)CCCCCCCCC)OCC(CCN(C)C)O1)CSC1CCCCC1] |
| 13 | 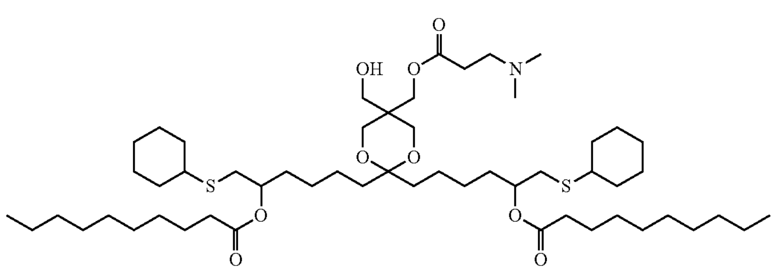 [SMILES: CCCCCCCCCC(=O)OC(CCCCC1(CCCCC(CSC2CCCCC2)OC(=O)CCCCCCCCC)OCC(CO)(COC(=O)CCN(C)C)CO1)CSC1CCCCC1] |
| 14 | 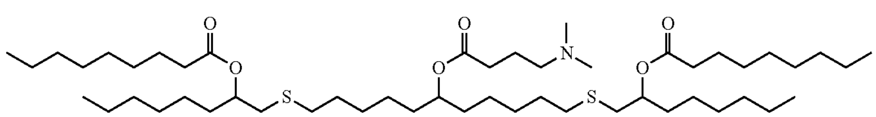 [SMILES: CCCCCCCCC(=O)OC(CCCCCC)CSCCCCCC(CCCCCSCC(CCCCCC)OC(=O)CCCCCCCC)OC(=O)CCCN(C)C] |
| 15 | 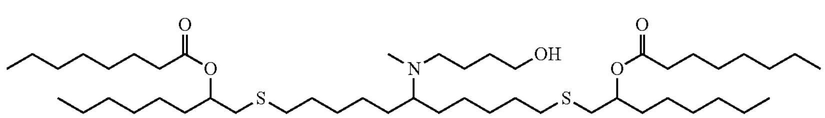 [SMILES: CCCCCCCC(=O)OC(CCCCCC)CSCCCCCC(CCCCCSCC(CCCCCC)OC(=O)CCCCCCC)N(C)CCCCO] |
| 16 | 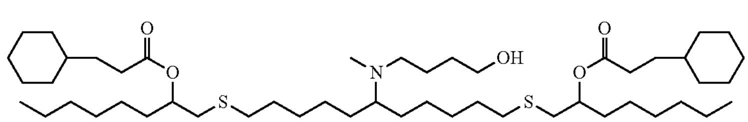 [SMILES: CCCCCCC(CSCCCCCC(CCCCCSCC(CCCCCC)OC(=O)CCC1CCCCC1)N(C)CCCCO)OC(=O)CCC1CCCCC1] |

TABLE 3-continued

Ionizable lipids formulated in PEG-less LNPs

| Ionizable lipid | Structure |
| --- | --- |
| 17 | 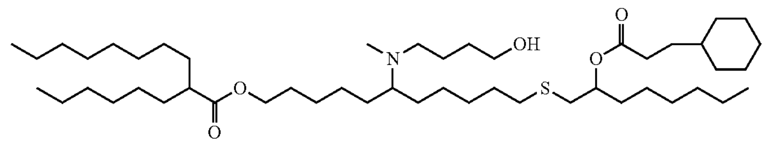 [SMILES: CCCCCCCCC(CCCCCC)C(=O)OCCCCCC(CCCCCSCC(CCCCCC)OC(=O)CCC1CCCCC1)N(C)CCCCO] |
| 18 | 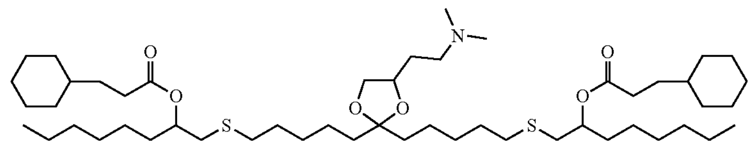 [SMILES: CCCCCCC(CSCCCCCC1(CCCCCSCC(CCCCCC)OC(=O)CCC2CCCCC2)OCC(CCN(C)C)O1)OC(=O)CCC1CCCCC1] |
| 19 | 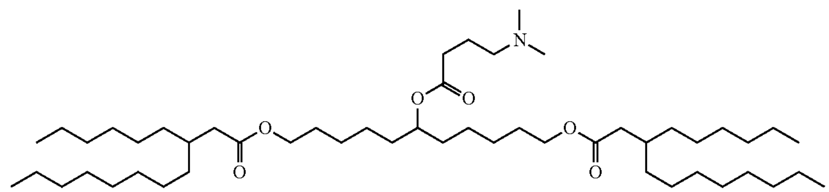 [SMILES: CCCCCCCCC(CCCCCC)CC(=O)OCCCCCC(CCCCCOC(=O)CC(CCCCCC)CCCCCCCC)OC(=O)CCCN(C)C] |
| 20 | 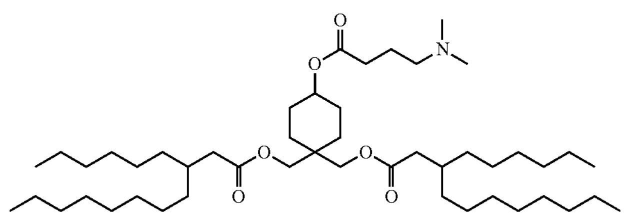 [SMILES: CCCCCCCCC(CCCCCC)CC(=O)OCC1(COC(=O)CC(CCCCCC)CCCCCCCC)CCC(OC(=O)CCCN(C)C)CC1] |
| 21 | 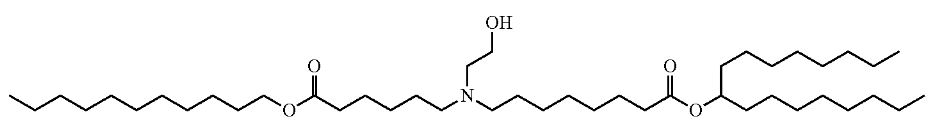 [SMILES: CCCCCCCCCCCOC(=O)CCCCCN(CCO)CCCCCCCC(=O)OC(CCCCCCCC)CCCCCCCC] |

Example 4: Modified Method to Formulate Ionizable Cationic Lipids that Cannot be Formulated in PEG-Less LNPs Using Standard Methods The ability of the ionizable lipids listed in Table 4 below to be formulated in PEG-less LNPs with mRNA encoding luciferase was assessed. The formulation method is a conventional rapid ethanol mixing method described in the Materials and Methods.

TABLE 4

Ionizable lipids tested for ability to be formulated in PEG-less mRNA-LNPs using standard and modified ethanol rapid mixing method

| Ionizable cationic lipid | Citation (incorporated herein by reference) |
| --- | --- |
| 1 | WO 2022/246571A1 |
| 12 | WO 2024/065042 (compound 16) |
| 15 | WO 2024/130421 (compound 24) |
| 16 | WO 2024/130421 (compound 27) |
| 17 | WO 2024/130421 (compound 8) |
| 20 | WO 2017/049245 |

The PEG-less LNPs contained 27.4/50/22.6 of ionizable lipid/DSPC/chol and the method used to prepare the LNPs was the unmodified rapid mixing ethanol method described in the Materials and Methods using mRNA encoding for firefly luciferase. The N/P was 9.

The results of physiochemical characterization are shown in FIG. 6. The 1 and 21 ionizable lipids were capable of being formulated in the PEG-less formulation using the unmodified LNP preparation method. However, the ionizable lipids 12, 15, 16 and 17 (Table 4) had undesirable physiochemical characteristics, namely low encapsulation efficiency and high PDI values, and were observed to agglomerate after dialysis or were not stable after concentration/storage.

The inventors modified the standard LNP preparation method in an attempt to formulate the ionizable lipids (12, 15, 16 and 18) that were not capable of being formulated in the above PEG-less LNPs (with mRNA). After the T-mixing (see Materials and Methods above), 1× phosphate buffered saline (PBS) was added to the formulation mixture in increasing volume ratios of LNP: 1× PBS (as indicated in FIGS. 7A-F) prior to dialysis followed by gentle mixing and transfer of the mixture to a dialysis bag in 1×PBS overnight followed by processing as usual. The PEG-less LNPs contained 27.4/50/22.6 of ionizable lipid/DSPC/chol (mol/mol) and the N/P was 9. Physiochemical characteristics (particle size, PDI and encapsulation %) were measured after dialysis and after dialysis and concentration of the LNPs to >0.25 mg/mL and overnight storage.

The impact of PBS dilution on mRNA-LNP formulation with the various ionizable lipids is shown in FIGS. 7A-F. The LNPs formulated with the ionizable lipid, 1, displayed acceptable physiochemical properties both after dialysis (FIG. 7A) and after concentration to >0.25 mg/mL, followed by overnight storage (FIG. 7B) for all ratios of PBS:LNP tested. The 1× PBS dilution tests were repeated using 12 as the ionizable cationic lipid (with mRNA) and the physiochemical properties are shown in FIG. 7C after dialysis and FIG. 7D after concentration to >0.25 mg/mL post-dialysis and overnight storage. For the 12 ionizable lipid, ratios of at least 1:1 (v:v) addition of 1×PBS post-mixing resulted in mRNA-LNPs that were stable after concentration and overnight storage. Addition of less than 1× volume of 1×PBS (ratios of 1:0.25, 1:0.5, undiluted), on the other hand, resulted in formulations that agglomerated upon dialysis. The 1× PBS dilution tests were repeated with 15, 16, and 18 as the ionizable lipids (formulated with mRNA). The physiochemical properties after dialysis (FIG. 7E) and concentration to >0.25 mg/mL post dialysis and overnight storage (FIG. 7F) were measured. For 16, a 1:2 (v:v) dilution resulted in stable particles which did not agglomerate in dialysis. The 15 formulations agglomerated in dialysis, regardless of dilution with 1×PBS. The dilution tests were repeated using 25 mM sodium acetate (NaOAc) dilution after T-mixing instead of PBS. Sodium acetate is the same buffer used in the aqueous nucleic acid solution introduced to the T-mixer. With 1 as the ionizable cationic lipid, all ratios of LNP:NaOAc (v:v) resulted in viable LNPs. The physiochemical results (size, PDI and encapsulation %) using 1 are shown in FIGS. 8A and 8B.

The 25 mM sodium acetate dilution tests were repeated with 12 as before (encapsulating mRNA). Similar to the results using 1 as the ionizable cationic lipid, all buffer dilution ratios resulted in viable PEG-less LNPs. The 12 PEG-less lcLNPs exhibited viable physiochemical characteristics both after dialysis and after concentration and storage (FIGS. 8B and 8C).

The 25 mM sodium acetate dilution tests were repeated with 15 and 16 with mRNA as the nucleic acid cargo. With the sodium acetate buffer diluent, the use of both ionizable cationic lipids resulted in stable PEG-less lcLNP compositions when the buffer-to-LNP ratio was as low as a 1:1 (v:v), with a 1:2-1:3 volume ratio resulting in ideal physiochemical characteristics for both of the ionizable cationic lipids. The PEG-less LNPs produced were stable after concentration and overnight storage. Dilution ratios below 1:1 (v:v) agglomerated in dialysis (FIGS. 8D and 8E).

The results suggest that both PBS and sodium acetate improve PEG-less LNP stability with ionizable lipids that could not otherwise be formulated using the standard ethanol mixing method. However, without being limiting, dilution with sodium acetate generally seems to result in LNPs that are more stable than dilution with 1×PBS after T-mixing.

Example 5: A Range of Different Buffers can be Used to Prepare Unshielded LNPs (PEG-Less) Containing Elevated Phosphatidylcholine and Reduced Levels of Ionizable Lipid This example demonstrates that additional buffers beyond those examined in Example 4 can produce stable PEG-less LNPs.

The LNP preparation method was the unmodified LNP preparation method set forth in the Materials and Methods but in which 50 mM acetate, formate and succinate replaced the 25 mM acetate buffer formulation buffer used as the solvent for the nucleic acid. Acetate buffer at 25 mM was the control. The PEG-less LNPs were 1/DSPC/Chol at 27.4/50/22.6 mol/mol and the N/P was 9.

The 25 mM sodium acetate buffer resulted in the most viable particles, although 50 mM sodium acetate, sodium formate and sodium succinate also produced LNPs that were stable after concentration and storage. The physiochemical results (size, PDI and encapsulation %) are shown in FIG. 9.

Example 6: Unshielded (PEG-Less) LNP Compositions were Found to be Stable after Vortexing, while a Corresponding PEG-Containing LNP was Unstable This example demonstrates that the PEG-less LNP was found to be stable after vortexing. Unexpectedly, an otherwise identical composition subjected to vortexing but with 1.5 mol % PEG-2000 DMG was unstable.

The LNP preparation method was the unmodified LNP preparation method set forth in the Materials and Methods using 25 mM sodium acetate. The nucleic acid cargo was mRNA encoding for firefly luciferase and the LNP formulations are set forth in Table 5 below:

TABLE 5

LNPs prepared with and without PEG for vortex studies

| LNP | Ionizable lipid mol % | DSPC | Cholesterol | PEG-2000 DMG mol % | N/P |
|---|---|---|---|---|---|
| A | 27.4 1 | 50 | 21.1 | 1.5 | 9 |
| B | 27.4 1 | 50 | 22.6 | 0 | 9 |

Both 1 LNP with PEG (LNP A) and 1 PEG-less lcLNP (LNP B) were subjected to vortexing of increments ranging from 15 sec-4 min, up to a total of 12 mins of total vortex time. The results are shown in FIGS. 10A and 10B. As shown in FIG. 10B, the PEG-less LNP B displayed no sign of change in physiochemical characteristics, while the LNP A formulated with PEG shows a significant increase in PDI and complete loss in payload encapsulation (FIG. 10A).

A subsequent vortex study was carried out to assess additional PEG-less formulations besides LNP B above. The additional PEG-less formulations examined are set out in Table 6 below. Each LNP contained 1 as the ionizable lipid.

TABLE 6

LNPs prepared with and without PEG for stability studies

| LNP | Ionizable lipid mol % | DSPC | Cholesterol | PEG-2000 DMG mol % | N/P |
|---|---|---|---|---|---|
| A | 27.4 | 50 | 21.1 | 1.5 | 9 |
| B | 50 | 10 | 38.5 | 1.5 | 9 |
| C | 27.4 | 50 | 22.6 | 0 | 9 |
| D | 33.05 | 40 | 26.95 | 0 | 9 |
| E | 25 | 40 | 35 | 0 | 9 |
| F | 20 | 40 | 40 | 0 | 9 |
| G | 33.33 | 33.33 | 33.33 | 0 | 9 |

As shown in FIG. 11A, the PEG-containing LNPs A and B exhibited a significant increase in PDI and a complete loss in payload encapsulation subsequent to 5 minutes of vortexing. Unexpectedly, the PEG-less LNPS C to G having varying mol % of ionizable lipid, phospholipid and sterol, all maintained size, PDI and encapsulation % after vortexing.

Example 7: PEG-Less LNP Compositions Exhibit Oxidative Stability, while a Corresponding PEG-Containing LNP was Unstable The introduction of air bubbles into lipid nanoparticle preparations negatively impacts their stability. This oxidative instability can diminish LNP shelf-life and potency (Musakhanian et al., 2022, AAPS PharmSciTech, 23:151).

This example demonstrates that a broad range of PEG-less LNP formulations are stable when exposed to oxidative conditions, while LNP formulations with PEG-lipid were unstable when exposed to the same conditions.

The LNP preparation method was the unmodified LNP preparation method set forth in the Materials and Methods using 25 mM sodium acetate. The nucleic acid cargo was mRNA encoding for firefly luciferase and the LNP formulations are set forth in Table 6 above.

The LNPs were dialyzed against buffer and then either subjected to oxidative conditions or left untreated. Physicochemical properties (size, PDI and encapsulation %) were measured after dialysis for both treated and untreated samples.

To create oxidative conditions, air was introduced to the treated LNP samples by connecting tubing to a compressed air line and adding a syringe/needle apparatus on the end to fit inside a tube containing the LNPs. Air was then introduced to the tubes at a steady stream continuously for 5 minutes.

As shown in FIG. 11B, the PEG-containing LNPs exhibited a significant increase in PDI and reduced payload encapsulation subsequent to 5 minutes of air bubbling (B bar) relative to the same LNP but left untreated (A bar). Unexpectedly, the five PEG-less LNPS (C to G of Table 6) having varying mol % of ionizable lipid, phospholipid and sterol, all had similar size, PDI and encapsulation % for samples subjected to air bubbling vs those left untreated.

Example 8: A PEG-Less LNP with a Phosphatidylcholine Lipid Having a Transition Temperature Above Room Temperature Exhibits Enhanced Stability PEG-less LNPs (encapsulating mRNA) were prepared with various helper lipids (DSPC, DMPC, ESM, POPC, SOPC, DOPE and DOPC) using 1 as the ionizable lipid. The formulations were 27.4 1/structural phospholipid/cholesterol at 27.4/50/22.6 (mol/mol) encapsulating mRNA at an N/P of 9. The LNPs were prepared using the unmodified LNP preparation method of the Materials and Methods.

PEG-less LNPs with DSPC showed no change in physiochemical characteristics after concentration and refrigerated storage. The LNPs prepared with the other helper lipids exhibited changes in physiochemical characteristics after concentration and refrigerated storage. It was found that DOPE and DOPC PEG-less LNPs agglomerated in dialysis. The results are presented in FIGS. 12A and 12B. Similar results were observed using the same structural lipids at 40 mol % (FIGS. 14A and 14B).

Without being limited by theory, the selection of a structural lipid, such as a PC lipid or mixtures thereof, in a PEG-less formulation having a phase transition temperature above room temperature may favour particle stability in PEG-less formulations. In this example, the enhanced stability of DSPC-containing PEG-less LNPs could be due to the high phase transition temperature of DSPC (55.6° C.) relative to the other non-cationic structural lipids tested.

The PEG-less LNP helper lipid screen was repeated using 12 as the ionizable lipid. The LNPs were prepared using the unmodified LNP method of the Materials and Methods (without buffer dilution) and therefore were unstable (see discussion in Example 4) and agglomerated upon dialysis, with the exception of DMPC. Notably, DMPC has a phase transition temperature of 24.1° C., which is above room temperature, and therefore may contribute to this observation. The use of DMPC produced particles with less ideal physiochemical characteristics, which deteriorated after concentration/storage (FIG. 13). However, the use of the buffer dilution method of preparation (modified method of the Materials and Methods) could be used to improve stability of the particles.

Example 9: Incorporation of Anionic Lipids into PEG-Less LNPs

PEG-less LNPs (encapsulating mRNA) were formulated with dioleoylphosphatidylglycerol (DOPG) using 1 as the ionizable lipid. The LNPs were prepared using the unmodified LNP preparation method of the Materials and Methods. The formulations were 27.4 1/DSPC+DOPG/cholesterol, 27.4 1/DSPC/cholesterol or 27.4 1/DOPG/cholesterol at 27.4/50/22.6 (mol/mol) encapsulating pDNA at an N/P of 9 as set out in Table 7 below.

TABLE 7

PEG-less LNP formulations with DOPG

| LNP | Ionizable lipid mol % | Helper Lipid mol % | Chol mol % | $PEG_{2000}$-DMG mol % | N/P |
|---|---|---|---|---|---|
| A | 27.4 | 50 DSPC | 22.6 | 0 | 9 |
| B | 27.4 | 40:10 DSPC:DOPG | 22.6 | 0 | 9 |
| C | 27.4 | 30:20 DSPC:DOPG | 22.6 | 0 | 9 |
| D | 27.4 | 20:30 DSPC:DOPG | 22.6 | 0 | 9 |
| E | 27.4 | 10:40 DSPC:DOPG | 22.6 | 0 | 9 |
| F | 27.4 | 50 DOPG | 22.6 | 0 | 9 |

Formulations with up to 20 mol % DOPG resulted in stable particles after concentration and storage, but 20 mol % DOPG resulted in very large LNPs (>110 nm). Interestingly, these large particles have a very low PDI. It was also observed that formulations having greater than 20 mol % DOPG (i.e., <30 mol % DSPC+>20 mol % DOPG) agglomerated in dialysis. The results are presented in FIG. 15.

PEG-less LNPs (encapsulating mRNA) were formulated with the anionic lipid, A-0001 (structure below) using 1 as the ionizable lipid. The LNPs were prepared using the unmodified LNP preparation method of the Materials and Methods. The formulations were 27.4 1/DSPC+A-0001/cholesterol, 27.4 1/DSPC/cholesterol or 27.4 1/A-0001/cholesterol at 27.4/50/22.6 (mol/mol) encapsulating pDNA at an N/P of 9 as set out in Table 8 below.

The structure of A-0001 is compound 16 of U.S. Provisional Application No. 63/453,766 filed on Mar. 22, 2023 (incorporated herein by reference) and is reproduced below:

Structure of A-0001:

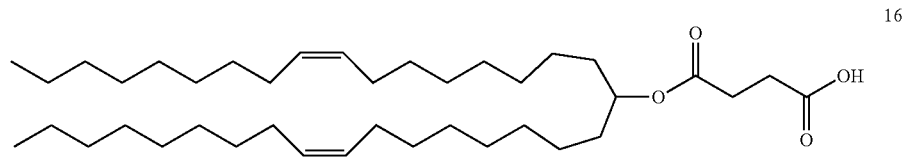 [SMILES: CCCCCCCC/C=C\CCCCCCCC(CCCCCCC/C=C\CCCCCCCC)OC(=O)CCC(=O)O]

TABLE 8

PEG-less LNP formulations with A-0001

| LNP | Ionizable lipid mol % | Helper Lipid mol % | Chol mol % | PEG$_{2000}$-DMG mol % | N/P |
|---|---|---|---|---|---|
| A | 27.4 | 50 DSPC | 22.6 | 0 | 9 |
| B | 27.4 | 40:10 DSPC:A-0001 | 22.6 | 0 | 9 |
| C | 27.4 | 30:20 DSPC:A-0001 | 22.6 | 0 | 9 |
| D | 27.4 | 20:30 DSPC:A-0001 | 22.6 | 0 | 9 |
| E | 27.4 | 10:40 DSPC:A-0001 | 22.6 | 0 | 9 |
| F | 27.4 | 50 A-0001 | 22.6 | 0 | 9 |

Formulations with up to 40 mol % A-0001 resulted in stable particles after concentration and storage, with 40 mol % A-0001 resulting in slightly larger LNPs with a much lower PDI. LNPs containing 50 mol % A-0001 (no DSPC) agglomerated in dialysis. The results are shown in FIG. 16.

The helper lipid ratio screen with DSPC and/or DOPG and A-0001 was repeated with viable compositions from the pDNA screen, now encapsulating mRNA encoding luciferase (instead of pDNA). The formulations are set out in Table 9 below.

TABLE 9

PEG-less LNP formulations with A-0001 and/or DOPG

| LNP | Ionizable lipid mol % | Helper Lipid mol % | Chol mol % | PEG$_{2000}$-DMG mol % | N/P |
|---|---|---|---|---|---|
| A | 27.4 | 50 DSPC | 22.6 | 0 | 9 |
| B | 27.4 | 40:10 DSPC:DOPG | 22.6 | 0 | 9 |
| C | 27.4 | 40:10 DSPC:A-0001 | 22.6 | 0 | 9 |
| D | 27.4 | 30:20 DSPC:A-0001 | 22.6 | 0 | 9 |
| E | 27.4 | 20:30 DSPC:A-0001 | 22.6 | 0 | 9 |

All PEG-less LNP compositions produced viable particles with mRNA, including after concentration and overnight storage. The results are shown in FIG. 17.

Example 10: A PEG-Less LNP was Stable Throughout the Range of 40 to 60 Mol % DSPC Content PEG-less LNPs (encapsulating mRNA) were formulated with 40-70 mol % DSPC using 1 as the ionizable lipid. The LNPs were prepared using the unmodified LNP preparation method of the Materials and Methods. The formulations encapsulated mRNA encoding for luciferase at an N/P of 9 and the formulations are set out in Table 10 below.

TABLE 10

PEG-less LNP formulations with 40-70 mol % DSPC

| LNP | Ionizable lipid mol % | Helper Lipid mol % | Chol mol % | PEG$_{2000}$-DMG mol % | N/P |
|---|---|---|---|---|---|
| A | 27.4 | 50 DSPC | 22.6 | 0 | 9 |
| B | 25 | 50 DSPC | 25 | 0 | 9 |
| C | 33 | 40 DSPC | 27 | 0 | 9 |
| D | 15 | 50 DSPC | 35 | 0 | 9 |
| E | 21 | 60 DSPC | 19 | 0 | 9 |
| F | 15 | 70 DSPC | 15 | 0 | 9 |

Variations in ratios of ionizable lipid:cholesterol and increasing amounts of DSPC were tested as shown in Table 10 above. All compositions resulted in LNPs with suitable physiochemical characteristics, which were maintained through concentration and overnight storage, apart from formulation F containing 70 mol % DSPC, which agglomerated in dialysis. The results for formulations A-E are shown in FIG. 18.

Example 11: Cryo-EM Images of PEG-Less LNPs

The lipid nanoparticles of Table 11 below were imaged using cryogenic electron microscopy (Cryo-EM).

TABLE 11

PEG-less LNP formulations

| LNP | Ionizable lipid No. (Table 3) | Ionizable lipid mol % | Helper Lipid mol % | Chol mol % | PEG$_{2000}$-DMG mol % | N/P |
|---|---|---|---|---|---|---|
| A | 1 | 25 | 50 DSPC | 25 | 0 | 9 |
| B | 1 | 33 | 40 DSPC | 27 | 0 | 9 |
| C | 1 | 15 | 50 DSPC | 35 | 0 | 9 |
| D | 1 | 21 | 60 DSPC | 19 | 0 | 9 |
| E | 12 | 27.4 | 50 DSPC | 22.6 | 0 | 9 |
| F | 16 | 27.4 | 50 DSPC | 22.6 | 0 | 9 |

The images are shown in FIG. 19A-F. As can be seen, the nanoparticle preparation comprises particles with cores having electron dense portions.

Example 12: Unshielded LNPs Exhibit Improved Local Delivery Relative to a PEG-Containing Baseline Formulations LNPs having elevated levels of neutral lipid (e.g., a phosphatidylcholine lipid) and lacking a PEG-lipid were next tested to determine tissue distribution in mice following intramuscular localized injection. The LNPs lacking PEG-lipid were prepared using the modified LNP method described above and encapsulated mRNA coding for luciferase. The ionizable lipid was lipid 15 of Table 3 in Example 3 above.

The baseline LNP and PEGless lcLNP compositions were as set forth in Table 12 below. Mice were injected intramuscularly with the LNPs at a dose of 1 µg and at 4 and 24 hours. and D-luciferin (as listed in Cayman™ chemicals catalog #14681) was administered to all 3 mice at a dose of 150 mg/kg intraperitoneally. A 15 mg/mL stock of D-luciferin was prepared using 1× Dulbecco's Phosphate Buffered Saline (containing no calcium or magnesium) and 10 µL/gram of body weight was administered intraperitoneally to each of the mice.

At 4 and 24 hours after LNP injection, the mice were anesthetized using 2.5-3% isoflurane in a chamber and were subsequently placed on the imaging platform maintained under 2% isoflurane through a nose cone.

All mice were imaged 10 mins post D-luciferin injection at an exposure time of 15 seconds. Bioluminescence imaging was performed using IVIS® Lumina II In Vivo Imaging System (IVIS). An untreated mouse was used as a negative control for background luminescence.

TABLE 12

PEG-less formulations and baseline formulations screened in vivo for tissue distribution after intramuscular injection

| Sample | Percent DSPC | Lipid composition/mol % |
|---|---|---|
| PEG-containing lcLNP ™ | 50 mol % | Ionizable lipid 15:DSPC:Chol:PEG$_{2000}$-DMG (27.4:50:21.1:1.5) |
| PEG-less lcLNP ™ | 50 mol % | Ionizable lipid 15:DSPC:Chol (27.4:50:22.6) |

The IVIS images at 4 and 24 hours are shown in FIG. 20A and FIG. 20B. As shown in FIG. 20A, at 4 hours for the benchmark LNP, the mRNA was present in both the liver (see arrow) and at the site of injection. However, the PEGless lcLNP™ only exhibited mRNA expression at the site of injection. Similar results were observed at 24 hours. These results show that the PEGless lcLNP™ exhibits improved localized delivery relative to the benchmark.

Example 13: Unshielded LNPs Exhibit Increased IgG Levels Against Spike Protein Relative to lcLNP™ PEG-Containing Formulations LNPs having elevated levels of neutral lipid (e.g., a phosphatidylcholine lipid) and lacking a PEG-lipid were next tested to determine IgG responses in mice. The LNPs lacking PEG-lipid were prepared using the modified LNP method described above. Two separate studies were conducted using different ionizable lipids.

Unexpectedly, the unshielded LNPs exhibited a significantly higher IgG response after a boost dose than a PEG-containing counterpart formulation.

The formulations examined in the first study are set forth in Table 13 below. The ionizable lipid was ionizable lipid 15 (compound 24 of WO 2024/130421).

TABLE 13

Unshielded LNPs and baseline formulations screened in vivo for IgG immune response in study 1

| Sample | Percent DSPC | Lipid composition/mol % |
|---|---|---|
| PEG-containing lcLNP ™ | 50 mol % | Ionizable lipid 15:DSPC:Chol:PEG$_{2000}$-DMG (27.4:50:21.1:1.5) |
| Unshielded lcLNP ™ | 50 mol % | Ionizable lipid 15:DSPC:Chol (27.4:50:22.6) |

The physiochemical properties of the lipid nanoparticles were measured as described in the Materials and Methods. The particle size (nm), encapsulation % and polydispersity index (PDI) were all within acceptable ranges.

Mice were injected intramuscularly at Day 0 (prime dose) and at Day 21 (boost dose with 1 µg of lcLNP™ formulations and PEG-less formulations encapsulating SARS CoV-2 spike mRNA.

Blood samples were collected and IgG levels were assayed as set forth in the Materials and Methods.

The observed Electrochemiluminescence (ECL) signal was plotted as the levels of IgG antibodies detected in serum samples for each group.

The results of the first study (conducted in two separate experiments) are shown in FIG. 21A. Unexpectedly, at day 35 after the prime dose, the PEG-less lcLNP™ exhibited higher IgG levels against SARS-CoV2 RBD than the lcLNP™ formulation with 1.5 mol % PEG$_{2000}$-DMG.

The second study examined the IgG response to PEGless lcLNP formulated with ionizable lipid 12, namely compound 16 of WO2024/065042.

The formulations tested are set out in Table 14 below.

TABLE 14

PEG-less formulations and baseline formulations screened in vivo for IgG immune response in study 2

| Sample | Percent DSPC | Lipid composition/ mol % | Cargo | Ionizable lipid citation (incorporated herein by reference) |
|---|---|---|---|---|
| PBS | NA | NA | NA | NA |
| nMC3 PEG-less lcLNP ™ luc | 50 mol % | Ionizable lipid 1 (norMC3): DSPC:Chol (27.4:50:22.6) | luciferase | WO 2022/ 246571 (ionizable lipid, p. 24) |
| Benchmark (ALC 50/10) | 10 mol % | ALC-0315:DSPC: Chol: PEG$_{2000}$-DMG (50:10: 38.5:1.5) | SARS COV-2 spike mRNA | WO 2018/ 081480 |
| PEGless lcLNP ™ | 50 mol % | Ionizable lipid 12:DSPC:Chol (27.4:50:22.6) | SARS COV-2 spike mRNA | WO2024/ 065042 (compound 16) |

Similar to the first study, at day 35 after the prime dose, the PEG-less lcLNP™ unexpectedly exhibited higher IgG levels against SARS-CoV2 RBD than the lcLNP formulation with 1.5 mol % PEG$_{2000}$-DMG (FIGS. 21B and 21C).

Example 14: Unshielded LNPs (PEG-Less lcLNP™) Generate Robust Innate Immune Responses Unshielded LNPs were next tested to determine innate immune responses in mice by ex vivo measurement of interleukin 6 (IL-6), interferon gamma (IFN-γ) and tumour necrosis factor alpha (TNF-α) after LNP injections. The LNPs encapsulated mRNA encoding for SARS CoV-2 spike mRNA. The benchmark LNP contained ALC-0315:DSPC:Chol:PEG$_{2000}$-DMG (50:10:38.5:1.5 mol:mol) with mRNA luciferase (ALC 50/10 luc) or with mRNA encoding SARS CoV-2 spike protein (ALC 50/10 Onpattro™) and the PEG-less formulation contained ionizable lipid 12:DSPC:Chol (27.4:50:22.6). The baseline formulations were prepared using the standard LNP preparation method and the unshielded LNPs (lacking PEG-lipid) were prepared using the modified LNP method described above in the Materials and Methods. The formulations that were tested are set out in Table 15 below. Phosphate buffered saline (PBS) was a negative control.

TABLE 15

PEG-less formulations and baseline formulations screened ex vivo for immune responses

| Sample | Percent DSPC | Lipid composition/mol % | Cargo | Ionizable lipid citation (incorporated herein by reference) |
|---|---|---|---|---|
| PBS | NA | NA | NA | NA |
| ALC 50/10 luc | 10 mol % | ALC-0315:DSPC:Chol:PEG$_{2000}$-DMG (50:10:38.5:1.5) | mRNA luciferase | WO 2018/081480 |
| ALC 50/10 | 10 mol % | ALC-0315:DSPC:Chol:PEG$_{2000}$-DMG (27.4:50:21.1:1.5) | SARS-COV2 RBD | WO 2018/081480 |
| PEGless lcLNP ™ | 50 mol % | Ionizable lipid 12:DSPC:Chol (27.4:50:22.6) | SARS-COV2 RBD | WO2024/065042 (compound 16) |

Mice were injected with the formulations at day 0 and with a booster at day 21 at a dose of 1 μg and MSD was used to measure the IL-6, IFN-γ and TNF-α levels ex vivo as per the Materials and Methods.

As can be seen in FIG. 22A, unexpectedly, the PEGless lcLNP formulation (PEGless lcLNP™) exhibited increased IL-6 relative to the benchmarks (ALC 50/10 luc and ALC 50/10). The IFN-γ and TNF-α levels were robust as well for the PEGless lcLNP as the respective levels were increased or comparable to the PEG-containing benchmarks (FIGS. 22B and 22C).

Example 15: Unshielded LNPs (PEG-Less lcLNP™) Generate Robust T Cell Responses

Unshielded LNPs were next tested to determine interferon gamma (IF Y) and interleukin-4 (IL-4) responses in mice relative to the PEG-containing benchmark LNPs. The LNPs encapsulated mRNA coding for SARS CoV-2 spike mRNA and the formulations tested are set forth in Table 15 above.

Mice were injected with the formulations at day 0 and with a booster at day 21 at a dose of 1 μg and Elispot™ was used to measure IFN γ and IL-4 responses from stimulated splenocytes. Splenocytes were extracted from the mice at day 35 and stimulated ex vivo with the spike peptide pool to examine the T cell response ex vivo as described in the Materials and Methods.

As can be seen in FIG. 23A, unexpectedly, the unshielded lcLNP formulation (PEGless lcLNP™) exhibited increased IFN γ relative to the PEG-containing benchmarks (ALC 50/10 luc and ALC 50/10). The IL-4 level of the PEGless formulation was robust as well (comparable to the benchmark; FIG. 23B).

Example 16: Unshielded LNPs (PEG-Less lcLNP™) Generate Robust Cellular Responses LNPs lacking a PEG-lipid were next tested to determine CD4$^+$ cellular immune responses in mice. The LNPs tested included the benchmark and PEGless lcLNP™ set forth in Table 15 above. Mice were injected with 1 μg of the formulations at day 0 and day 21 and Intracellular Cytokine Staining (flow experiment) was used to measure the percentage of activated CD4+ T cells with cytokine levels ex vivo as indicated in the Materials and Methods.

The percentage of activated CD4$^+$ or CD8+ T cells positive for interferon gamma (IFNg$^+$), tumour necrosis factor α (TNFa$^+$), IFN γ and TNF-α cytokines (IFNg$^+$/TNFa$^+$cytokines), interleukin-2 (IL-2$^+$) and interleukin-4 (IL-4$^+$) levels were measured ex vivo.

The results presented in FIG. 24A show that the PEGless LNP formulation caused a robust T-helper Type 1 (TH-type 1) IFNg$^+$, IFNg$^+$/+TNFa$^+$ and IL-2$^+$ cellular response in CD4$^+$ T cells. Likewise, in CD8+ T cells, the results in FIG. 24B show that the PEGless LNP formulation caused a robust type 1 IFNg$^+$/+TNFa$^+$, IL-2$^+$immune response.

Example 17: Unshielded LNPs (PEG-Less lcLNP™) Generate Functional Antibodies Responses Unshielded LNPs were next tested to determine the functional antibody mounted against ACE2 binding to SARS CoV-2 receptor binding domain (RBD) in mice. The LNPs tested included PEGless LNP and the benchmark and PEGless lcLNP™ set forth in Table 15 above. Mice were injected with the formulations at a dose of 1 μg with prime and boost doses as per the procedure set forth in the Materials and Methods. The percentage inhibition of ACE2 binding to SARS CoV-2 RBD due to antibody was measured at dilutions of 1/300 and 1/1000.

The results in FIGS. 25A and 25B show that the PEGless lcLNP™ generate equivalent functional antibodies against the RBD as the benchmark LNP as measured by percentage inhibition.

Example 18: mRNA Gene Expression in T Cells Increases Significantly Using Unshielded LNPs Relative to a Baseline Formulation LNPs with and without PEG$_{2000}$-DMG and containing enhanced green fluorescent protein mRNA ("eGFP mRNA") cargo were evaluated in primary human CD8$^+$ T-cells ex vivo.

In particular, the following eGFP mRNA formulations (reported in mol %) comprising ionizable lipid (as indicated), DSPC and cholesterol (with or without PEG) were compared in this example.

TABLE 16

Formulations examined ex vivo containing eGFP mRNA

| Sample | Percent DSPC | Lipid composition/mol % | Ionizable lipid citation (incorporated by reference) |
|---|---|---|---|
| baseline | 10 mol % | Ionizable lipid 1:DSPC:Chol:PEG$_{2000}$-DMG (50:10:38.5:1.5) | WO 2022/246571; nor-MC3 |
| lcLNP ™ (PEG-less) | 50 mol % | Ionizable lipid 15:DSPC:Chol (28.15:50:21.85) | Ionizable lipid 15 WO 2024/130421 (compound 24) |

The baseline formulation and the unshielded lcLNP™ formulations in Table 16 above had favourable physio-chemical characteristics. The results are summarized below in Table 17.

TABLE 17 characteristics of the baseline and lcLNP ™ of Table 16

| Group | N/P | Encapsulation % | Size Z-Average (nm) | Size number-average (nm) | PDI |
|---|---|---|---|---|---|
| baseline | 6 | 97 | 71.7 | 55.6 | 0.163 |
| lcLNP ™ (PEG-less) | 9 | 97 | 106.3 | 76.9 | 0.193 |

Live/dead staining and measurement of eGFP using flow cytometry was assessed for the CD8+ T cells. The eGFP was measured at 48 hours following dose titration (1, 2, 4, 6 and 8 µg) of the baseline and the lcLNP™.

The results for the live/dead staining and mRNA expression of CD8+ T cells are presented in FIGS. 26A and 26B.

The results in FIGS. 26A and 26B show that at 48 hours post-addition of the LNPs at the indicated doses, the T cell samples treated with the GFP mRNA-containing lcLNP™ without PEG had significantly more cells positive for GFP over the baseline formulation containing PEG (FIG. 26B; see peak shift of lcLNP™ group).

In addition, as shown in FIG. 26B, at the 8 µg dose for GFP expression, the baseline LNP containing PEG exhibited a left shift relative to the other doses tested, whereas the PEG-less lcLNP™ at the same dose exhibited no such shift in expression. This result may suggest that the baseline LNP containing PEG is more toxic at this dose relative to the PEG-less LNP.

Example 19: Gene Editing Efficacy Targeting the TRAC Locus Using High DSPC LNPs Relative to a Baseline Formulation T cell receptor a constant (TRAC) gene editing knock-out (KO) efficiency using Cas9/CRISPR was next investigated comparing the baseline LNP and unshielded lcLNP™ (with no PEG) in primary CD8+ T cells. Gene knock-out of the TRAC gene locus encoding for the T cell receptor was of interest since it can be targeted for integration of CAR transgenes or to produce allogeneic T cells.

The following LNP formulations (reported in mol %) encapsulating mRNA encoding Cas9 and TRAC gRNA or scrambled gRNA were compared in this example for TRAC gene knock-out efficiency. Baseline LNPs with norMC3 (ionizable lipid 1) and ionizable lipid 15 (baseline LNPs A and B) were compared to unshielded lcLNP™ (PEGless) formulations with 50 mol % DSPC with ionizable lipid 15 (LNP C and D). The baseline LNP contained Cas9/TRAC gRNA (LNPs A and B) and the unshielded lcLNP™ formulations contained Cas9/TRAC gRNA (LNP C) or scrambled gRNA (LNP D).

TABLE 18

LNP formulations analyzed for TRAC gene editing knock-out efficiency

| LNP | Sample | Percent DSPC | Lipid composition/mol % | Ionizable lipid (IL) citation (incorporated by reference) | Cargo |
|---|---|---|---|---|---|
| A | baseline 1 | 10 mol % | Ionizable lipid 1:DSPC:Chol:PEG$_{2000}$-DMG (50:10:38.5:1.5) | Ionizable lipid 1, WO 2022/246571; nor-MC3 | Cas9/TRAC gRNA |
| B | baseline 2 | 10 mol % | Ionizable lipid 15:DSPC:Chol:PEG$_{2000}$-DMG (50:10:38.5:1.5) | Ionizable lipid 15, WO 2024/130421 (compound 24) | Cas9/TRAC gRNA |
| C | lcLNP ™ (PEG-less) | 50 mol % | Ionizable lipid 15:DSPC:Chol (28.15:50:21.85) | Ionizable lipid 15, WO 2024/130421 (compound 24) | Cas9/TRAC gRNA |
| D | lcLNP ™ (PEG-less) scramble | 50 mol % | Ionizable lipid 15:DSPC:Chol (28.15:50:21.85) | Ionizable lipid 15, WO 2024/130421 (compound 24) | Cas9/SCR gRNA (scrambled) |

The Onpattro™-type formulation (baseline) and the PEG-less lcLNP™ formulations in Table 18 above had favourable physiochemical characteristics. The results are summarized below in Table 19 below.

TABLE 19

Physiochemical characteristics of the baseline and lcLNP ™

| LNP | Sample | N/P | Encapsulation % | Size Z-Average (nm) | Size number-average (nm) | IPDI |
|---|---|---|---|---|---|---|
| A | baseline 1 | 6 | 98 | 74.6 | 58.4 | 0.035 |
| B | baseline 2 | 6 | 94 | 87.0 | 66.0 | 0.069 |
| C | lcLNP ™ (PEG-less) | 9 | 99 | 94.3 | 68.5 | 0.141 |
| D | lcLNP ™ (PEG-less) scramble | 9 | 99 | 91.7 | 68.5 | 0.136 |

Primary human CD8+ T-cells were treated with the LNPs of Table 18. A T7 endonuclease detection assay (see Materials and Methods) was used to assess genome editing of the TRAC locus of the T-cells and the results are presented in the gel depicted in FIG. 28A. The gel provides a measure of the cleaved heteroduplexes, which in turn corresponds to the level of indel (editing) activity. As can be seen, after the addition of the T7 endonuclease (T7EI), genomic DNA treated with the LNPs was digested and appears as three distinct bands (FIG. 28A, baseline LNP and unshielded lcLNP™ (PEG-less)), indicative of editing of the locus, while the control and lcLNP™ with scrambled gRNA remained undigested.

FIG. 28B is a graph showing gene editing efficiency (%) for baseline 1; baseline 2; lcLNP™ PEG-less (LNP C); and lcLNP™ PEG-less scramble (LNP D). Unexpectedly, only the unshielded lcLNP™ (PEG-less; LNP C) showed any significant gene editing measured as INDEL % and knock-out score. Both baseline LNP and lcLNP™ PEG-less scramble formulations had zero INDEL % and knockout scores.

FIG. 28C shows flow cytometry results measuring T cell receptor (TCR) 8 days post-LNP treatment comparing LNPs A-D of Table 18 above. Unexpectedly, only the unshielded lcLNP™ (PEG-less) sample with intact TRAC gRNA exhibited a shift in the peak indicative of cells with lower T cell receptor count. The un-transfected sample, baseline LNP samples with PEG and unshielded lcLNP™ (PEG-less) with scrambled TRAC gRNA did not show any shift in the peaks indicative of lower TCR count.

FIG. 28D shows percentage knock-out for each LNP sample of Table 18 normalized to the untreated sample. Only the lcLNP™ unshielded (PEG-less) sample with intact TRAC gRNA exhibited significant knock-out of TCR and CD3 expression (>60%). The remaining PEG-containing baseline LNPs had knock-out percentages of around 20% or less relative to the untreated sample.

Example 20: Characteristics and Efficacy of Unshielded lcLNP™ (PEG-Less) in Primary Human CD4+ and CD8+ T Cells The PEG-less lcLNP™ sample C of Table 18 of Example 19 having ionizable lipid 15:DSPC:Chol (28.15:50:21.85) was analyzed for T cell receptor (TCR) expression by flow cytometry 8 days post LNP treatment with CD4+ and CD8+ cells at a dose of 2.5 µg.

As can be seen in FIG. 29A, the unshielded lcLNP™ (PEG-less) with Cas9 and TRAC gRNA showed reductions in TCR signal for both CD4+ and CD8+ human T cells. The percentage knock-out (KO) of TCR and CD3 relative to the untreated cells was around 90% for CD4+ cells and around 70% for CD8+ cells (FIG. 29B).

Example 21: Ex Vivo LNP-Mediated Knock-In of Primary T Cells

Given the successful knock-out of the TRAC locus achieved in the previous examples, the inventors next investigated LNP-mediated knock-in of eGFP in the TRAC locus of CD4+ T cells. The LNP formulations examined were as follows: lcLNP™ PEG-less:ionizable lipid 15:DSPC:Chol (28.15:50:21.85) The LNP cargo was Cas9 mRNA:TCR gRNA (1:1 wt:wt) for knock-out only (control) or Cas9 mRNA:TCR gRNA:GFP homology directed repair (HDR) DNA (1:1:3 wt:wt) for the knock-out/knock-in studies. The cut site in the TRAC exon 1 is depicted in FIG. 30A, as well as the HDR template comprising a sequence encoding GFP flanked by left homology arm (LHA) and right homology arm (RHA) sequences. The knock-out and knock-out/knock-in studies were carried out as set forth in the Materials and Methods.

The results are shown in FIGS. 30B-E. Un-transfected T cells were primarily of the wild-type phenotype as measured by flow cytometry (FIG. 30B). The T cells treated with LNPs having only knock-out cargo, Cas9 mRNA:TCR gRNA, exhibited 91% knock out (FIG. 30C). The knock-out/knock-in sample (KO+KI) treated with LNPs having Cas9 mRNA: TCR gRNA:GFP HDR DNA exhibited 75% knock-out and 7% knock-in (FIG. 30D), while the same knock-out/knock-in sample treated with NHEJ inhibitor M3814 exhibited 75% knock-out and 11% knock-in (FIG. 30E).

Example 22: Expression of mRNA in HSPC Bone Marrow Cell Subsets Using Unshielded High DSPC LNPs The effect of eliminating $PEG_{2000}$-DMG on eGFP expression in LNPs was evaluated in bone marrow haematopoietic stem and progenitor cells (HSPCs) in vivo. Unexpectedly, such unshielded lcLNP™ formulations exhibited improved eGFP relative to a baseline formulation comprising PEG-lipid.

In particular, the following luciferase control and eGFP mRNA LNP formulations comprising ionizable lipid (as indicated), DSPC and cholesterol were compared in this example (Table 20, LNPs 1, 3 and 4) to the PEG-containing control, which was Onpattro™ baseline (LNP 2). The luciferase and uLNP™ formulations lacking PEG were prepared by a modified method in which, after T-mixing, buffer was added to the formulation mixture in increasing ratios of LNP: 1× buffer prior to dialysis and gently mixed, followed by transfer to dialysis in 1× PBS followed by processing as usual.

TABLE 20

Unshielded formulations (uLNP) examined in vivo containing eGFP mRNA

| Group | Sample | Percent DSPC | Lipid composition/mol % | Ionizable lipid citation (incorporated by reference) |
|---|---|---|---|---|
| 1 | Luc control | 40 mol % | Ionizable lipid 1:DSPC:Chol: (20:40:40) | WO 2022/246571 (norMC3) |
| 2 | Benchmark (Onpattro ™) | 10 mol % | Ionizable lipid 1:DSPC:Chol:PEG$_{2000}$-DMG (50:10:38.5:1.5) | WO 2022/246571 (norMC3) |
| 3 | uLNP | 40 mol % | Ionizable lipid 16:DSPC:Chol: (20:40:40) | WO 2024/130421 compound 27 |
| 4 | uLNP | 40 mol % | Ionizable lipid 22:DSPC:Chol: (20:40:40) | WO 2024/130421, compound 27 modified to include an additional methylene (CH$_2$) in both inner alkyl chains |

The luciferase control, Onpattro™ benchmark and the lcLNP™ formulations in Table 20 above had favourable physiochemical characteristics (FIG. 31A).

Flow cytometry was used to investigate the expression of eGFP mRNA in haematopoietic stem and progenitor cell subsets of bone marrow of C57Bl/6 mice at various time points post-injection. The flow cytometry gating scheme of the bone marrow HSPCs is shown in Table 21 below.

TABLE 21

Gating scheme on live haematopoietic stem and progenitor (HSPC) cells for uLNP studies

| HSPC Population in Bone Marrow | Gating Scheme | Figure |
|---|---|---|
| LK | Lineage$^-$c-Kit$^+$ | 31B |
| LSK | Lineage$^-$ c-Kit$^+$ Sca1$^+$ | 31B |
| Multipotent progenitor (MPP) | Lineage$^-$ c-Kit$^+$ Sca1$^+$CD34$^+$ | 31C |
| Short-term HSC (ST-HSC) | Lineage$^-$c-Kit$^+$Sca1$^+$CD34$^+$CD135$^+$ | 31C |
| Long-term HSC (LT-HSC) | Lineage$^-$ cKit$^+$ Sca1$^+$ CD34$^-$CD135$^-$ | 31C |

The results in FIGS. 31B and 31C show that at 24 hours post-administration, the haematopoietic stem or progenitor cell sub-populations in the bone marrow of mice treated with the GFP mRNA-unshielded LNPs containing 40 mol % DSPC (uLNPs 3 and 4 in Table 20) exhibited an increase of cells positive for GFP over the Onpattro™ benchmark (LNP 2 in Table 20). This was observed for all sub-populations of bone marrow HSPC analyzed.

The examples are intended to illustrate the preparation of specific lipid nanoparticle nucleic acid preparations and properties thereof but are in no way intended to limit the scope of the invention.

The article "a" or "an" as used herein is meant to include both singular and plural, unless otherwise indicated.

The invention claimed is:

1. A pharmaceutical composition comprising a lipid nanoparticle, the lipid nanoparticle comprising:
   an effective amount of a nucleic acid cargo molecule;
   a sterol present at greater than 12 mol %;
   a neutral lipid present at a content of between 22 mol % and 65 mol %; and
   an ionizable cationic amino lipid present at a content of between 15 mol % and 45 mol %;
   wherein the lipid nanoparticle is unshielded or is non-sterically stabilized with a hydrophilic polymer-lipid conjugate, and
   wherein each content in mol % is relative to a total lipid content present in the lipid nanoparticle.

2. The pharmaceutical composition of claim 1, wherein the content of the sterol is between 15 mol % and 40 mol %.

3. The pharmaceutical composition of claim 1, wherein the ionizable cationic amino lipid content is less than 40 mol %.

4. The pharmaceutical composition of claim 1, wherein the neutral lipid is a phospholipid having a choline head group.

5. The pharmaceutical composition of claim 4, wherein the content of the phospholipid having a choline head group is between 25 mol % and 60 mol %.

6. The pharmaceutical composition of claim 1, wherein the content of the hydrophilic-polymer lipid conjugate is less than 0.40 mol %.

7. The pharmaceutical composition of claim 4, wherein the phospholipid having the choline head group is a phosphatidylcholine or a sphingolipid and wherein the phosphatidylcholine:sterol or sphingolipid:sterol molar ratio is between 0.5:1 and 3:1.

8. The pharmaceutical composition of claim 1, wherein the nucleic acid cargo molecule is siRNA, mRNA, vector nucleic acid, an antisense oligonucleotide or is a nucleic acid-protein or peptide complex.

9. The pharmaceutical composition of claim 1, wherein the ionizable lipid is a non-cyclopentane ring-containing ionizable lipid; a non-furan ring-containing ionizable lipid; or comprises one or more biodegradable groups in a lipophilic chain or chains.

10. The pharmaceutical composition of claim 1, wherein the sterol is a cholesterol.

11. The pharmaceutical composition of claim 4, wherein the phospholipid having a choline head group is a phosphatidylcholine selected from DOPC, DPPC and DSPC.

12. The pharmaceutical composition of claim 11, wherein a content of the phosphatidylcholine comprises at least the DSPC.

13. The pharmaceutical composition of claim 1, wherein the effective amount of the nucleic acid in the lipid nanoparticle encodes for a protein, peptide or polypeptide that is non-antigenic for infectious disease caused by a virus.

14. The pharmaceutical composition of claim 1, wherein the effective amount of the nucleic acid in the lipid nanoparticle is mRNA or vector DNA is for in vivo production of protein or peptide in an extrahepatic tissue or organ.

* * * * *